US011529166B2

(12) United States Patent
Esarey et al.

(10) Patent No.: US 11,529,166 B2
(45) Date of Patent: *Dec. 20, 2022

(54) POWER OPERATED ROTARY EXCISION TOOL

(71) Applicant: EXSURCO MEDICAL, INC., Wakeman, OH (US)

(72) Inventors: Bernard J. Esarey, Lorain, OH (US); Jason A. Sukey, Elyria, OH (US); Jeffrey A. Whited, Richfield, OH (US)

(73) Assignee: Exsurco Medical, Inc., Wakeman, OH (US)

( * ) Notice: Subject to any disclaimer, the term of this patent is extended or adjusted under 35 U.S.C. 154(b) by 397 days.

This patent is subject to a terminal disclaimer.

(21) Appl. No.: 16/742,483

(22) Filed: Jan. 14, 2020

(65) Prior Publication Data

US 2020/0155186 A1 May 21, 2020

Related U.S. Application Data

(63) Continuation of application No. 15/823,528, filed on Nov. 27, 2017, now Pat. No. 10,537,356, which is a
(Continued)

(51) Int. Cl.
*A61B 17/322* (2006.01)
*B23P 15/40* (2006.01)
(Continued)

(52) U.S. Cl.
CPC .......... *A61B 17/322* (2013.01); *B23P 15/406* (2013.01); *A61B 2017/00526* (2013.01);
(Continued)

(58) Field of Classification Search
CPC ........ A61B 17/322; A61B 2017/00761; A61B 2090/033; A61B 2017/00526;
(Continued)

(56) References Cited

U.S. PATENT DOCUMENTS 324,435 A   8/1885  Underwood
941,829 A   11/1909 Walder et al.
(Continued)

FOREIGN PATENT DOCUMENTS

EP   0190827   8/1986
FR   1216947   4/1960
(Continued)

OTHER PUBLICATIONS

Oct. 3, 2011 Decision and Opinion of the United States Court of Appeals for the Federal Circuit (Appeal No. 2011-1038-1046) regarding the case styled *Bettcher Industries, Inc. v. Bunzl USA, Inc. and Bunzl Processor Distribution, LLC*, Case No. 3:08 CV 2423, U.S. District Court for the Northern District of Ohio, Judge Zouhary. The Decision and Opinion relates to U.S. Pat. No. 7,00,325, owned by a related company of the assignee of the present application. (47 pages).

(Continued)

*Primary Examiner* — Julian W Woo
(74) *Attorney, Agent, or Firm* — Tarolli, Sundheim, Covell & Tummino LLP

(57) ABSTRACT

An exemplary hand-held, power operated rotary knife dermatome comprises a blade housing assembly and a depth gauge assembly. The blade housing assembly includes an annular blade housing and a blade lock ring for rotatably supporting an annular rotary knife blade. The annular blade housing includes a shield extending radially inwardly from a blade receiving body and including an inner wall defining a tissue directing surface, the tissue directing surface including a first tissue guide surface extending upwardly from a lower end of the shield, the first tissue guide surface extending substantially parallel to the blade housing axially extending center line. The blade receiving body includes an annular blade channel extending axially upwardly from a lower
(Continued)

surface of the blade receiving body, a bearing surface axially spaced from a lower surface of the blade receiving body, and a threaded portion formed on the outer surface of the annular blade housing.

21 Claims, 35 Drawing Sheets

Related U.S. Application Data continuation-in-part of application No. 14/741,012, filed on Jun. 16, 2015, now abandoned, and a continuation-in-part of application No. 14/725,303, filed on May 29, 2015, now Pat. No. 10,022,146.

(60) Provisional application No. 62/427,148, filed on Nov. 28, 2016, provisional application No. 62/012,707, filed on Jun. 16, 2014.

(51) Int. Cl.
A61B 90/00 (2016.01)
A61B 17/00 (2006.01)

(52) U.S. Cl.
CPC .............. A61B 2017/00544 (2013.01); A61B 2017/00761 (2013.01); A61B 2090/033 (2016.02); A61B 2090/061 (2016.02); B23B 2200/202 (2013.01); B23B 2220/12 (2013.01)

(58) Field of Classification Search
CPC ..... A61B 2090/061; A61B 2017/00544; B23P 15/406; B23B 2220/12; B23B 2200/202
See application file for complete search history.

(56) References Cited

U.S. PATENT DOCUMENTS

| | | |
|---|---|---|
| 1,220,345 A | 3/1917 | Koster |
| 1,374,988 A | 4/1921 | Cooper |
| 1,379,153 A | 5/1921 | Young |
| 1,476,345 A | 12/1923 | McGee |
| 2,123,712 A | 7/1938 | Clark |
| 2,263,431 A | 11/1941 | White |
| 2,266,888 A | 12/1941 | McCurdy et al. |
| 2,540,462 A | 2/1951 | Smith |
| 2,582,511 A | 1/1952 | Stryker |
| 2,730,100 A | 1/1956 | Hood |
| 2,730,102 A | 1/1956 | Hood |
| 2,827,657 A | 3/1958 | Bettcher |
| 3,126,889 A | 3/1964 | Blumenfeld |
| 3,197,808 A | 8/1965 | Mears |
| RE25,947 E | 12/1965 | Bettcher |
| 3,269,010 A | 8/1966 | Bettcher |
| 3,461,557 A | 8/1969 | Behring |
| 3,670,734 A | 6/1972 | Hardy, Jr. |
| 3,688,403 A | 9/1972 | Bettcher |
| 4,082,232 A | 4/1978 | Brewer |
| 4,142,291 A | 3/1979 | Bettcher |
| 4,166,317 A | 9/1979 | Bettcher |
| 4,170,063 A | 10/1979 | Bettcher |
| 4,178,683 A | 12/1979 | Bettcher |
| 4,198,750 A | 4/1980 | Bettcher |
| 4,211,232 A | 7/1980 | Mormann et al. |
| 4,236,531 A | 12/1980 | McCullough |
| 4,267,759 A | 5/1981 | Sullivan et al. |
| 4,326,361 A | 4/1982 | McGill |
| 4,363,170 A | 12/1982 | McCullough |
| 4,439,924 A | 4/1984 | Bettcher |
| 4,448,101 A | 5/1984 | Templeton |
| 4,492,027 A | 1/1985 | Bettcher |
| 4,494,311 A | 1/1985 | McCullough |
| 4,509,261 A | 4/1985 | Bettcher |
| 4,516,323 A | 5/1985 | Bettcher et al. |
| 4,575,937 A | 3/1986 | McCullough |
| 4,575,938 A | 3/1986 | McCullough |
| 4,590,676 A | 5/1986 | Bettcher |
| 4,609,227 A | 9/1986 | Wild et al. |
| 4,637,140 A | 1/1987 | Bettcher |
| 4,829,860 A | 5/1989 | VanderPol |
| 4,854,046 A | 8/1989 | Decker |
| 4,858,321 A | 8/1989 | McCullough |
| 4,909,640 A | 3/1990 | Nakanishi |
| 5,099,721 A | 3/1992 | Decker et al. |
| 5,163,288 A | 11/1992 | Doley |
| 5,230,154 A | 7/1993 | Decker et al. |
| 5,331,877 A | 7/1994 | Ishii |
| 5,419,619 A | 5/1995 | Lew |
| 5,522,142 A | 6/1996 | Whited |
| 5,529,532 A | 6/1996 | Desrosiers |
| 5,632,090 A | 5/1997 | Smith |
| 5,664,332 A | 9/1997 | Whited et al. |
| 5,692,307 A | 12/1997 | Whited et al. |
| 5,761,817 A | 6/1998 | Whited et al. |
| 5,940,972 A | 8/1999 | Baris et al. |
| 5,971,413 A | 10/1999 | Kassouf |
| 6,070,945 A | 6/2000 | Ritchey et al. |
| 6,327,783 B1 | 12/2001 | Ming |
| 6,354,949 B1 | 3/2002 | Baris et al. |
| 6,460,254 B1 | 10/2002 | Mori et al. |
| 6,604,288 B2 | 8/2003 | Whited et al. |
| 6,615,494 B2 | 9/2003 | Long et al. |
| 6,665,943 B1 | 12/2003 | Sloane et al. |
| 6,694,649 B2 | 2/2004 | Whited et al. |
| 6,751,872 B1 | 6/2004 | Whited et al. |
| 6,769,184 B1 | 8/2004 | Whited |
| 6,857,191 B2 | 2/2005 | Whited |
| 6,880,249 B2 | 4/2005 | Long et al. |
| 6,978,548 B2 | 12/2005 | Whited et al. |
| 7,000,325 B2 | 2/2006 | Whited |
| 8,002,779 B2 | 8/2011 | Barker et al. |
| 8,037,611 B2 | 10/2011 | Levsen |
| 8,608,755 B2 | 12/2013 | Mahaffey et al. |
| 8,661,692 B2 | 3/2014 | Whited et al. |
| 8,739,416 B2 | 6/2014 | Mascari et al. |
| 8,752,299 B2 | 6/2014 | Rosu et al. |
| 8,756,819 B2 | 6/2014 | Whited et al. |
| 8,806,761 B2 | 8/2014 | Whited et al. |
| 8,814,881 B2 | 8/2014 | Boles et al. |
| 8,926,632 B2 | 1/2015 | Mahaffey et al. |
| 9,186,171 B2 | 11/2015 | Esarey et al. |
| 9,592,076 B2 | 3/2017 | Esarey et al. |
| 9,623,577 B2 * | 4/2017 | Whited .................. A22C 17/12 |
| 10,022,146 B2 | 7/2018 | Esarey et al. |
| 10,039,567 B2 | 8/2018 | Esarey et al. |
| 10,537,356 B2 | 1/2020 | Esarey et al. |
| 2002/0096027 A1 | 7/2002 | Whited et al. |
| 2003/0070301 A1 | 4/2003 | Hermann et al. |
| 2003/0084576 A1 | 5/2003 | Whited |
| 2003/0131482 A1 | 7/2003 | Long et al. |
| 2003/0196333 A1 | 10/2003 | Whited |
| 2004/0187316 A1 | 9/2004 | Whited et al. |
| 2004/0211067 A1 | 10/2004 | Whited et al. |
| 2005/0126015 A1 | 6/2005 | Whited |
| 2005/0178009 A1 | 8/2005 | Whited |
| 2005/0217119 A1 | 10/2005 | Rapp |
| 2006/0037200 A1 | 2/2006 | Rosu et al. |
| 2006/0137193 A1 | 6/2006 | Whited |
| 2007/0283573 A1 | 12/2007 | Levsen |
| 2007/0283574 A1 | 12/2007 | Levsen |
| 2008/0022537 A1 | 1/2008 | Clarke et al. |
| 2008/0098605 A1 | 5/2008 | Whited et al. |
| 2008/0168667 A1 | 7/2008 | Spinato |
| 2008/0183109 A1 | 7/2008 | Babaev |
| 2009/0138027 A1 | 5/2009 | Lucas et al. |
| 2009/0157095 A1 | 6/2009 | Barker et al. |
| 2009/0227192 A1 | 9/2009 | Luthi et al. |
| 2010/0101097 A1 | 4/2010 | Thien |
| 2011/0185580 A1 | 8/2011 | Whited |
| 2011/0247220 A1 | 10/2011 | Mascari et al. |
| 2012/0138125 A1 | 6/2012 | Hammermann et al. |
| 2012/0191121 A1 | 7/2012 | Chen et al. |
| 2013/0025134 A1 | 1/2013 | Mascari et al. |

(56) References Cited

U.S. PATENT DOCUMENTS

| | | |
|---|---|---|
| 2013/0025139 A1 | 1/2013 | Whited et al. |
| 2013/0174424 A1 | 7/2013 | Whited et al. |
| 2014/0074118 A1 | 3/2014 | Esarey et al. |
| 2014/0074119 A1 | 3/2014 | Esarey et al. |
| 2014/0074120 A1 | 3/2014 | Esarey et al. |
| 2014/0236180 A1 | 8/2014 | Shalfirstein |
| 2016/0106451 A1 | 4/2016 | Esarey |
| 2016/0345996 A1 | 12/2016 | Esarey et al. |
| 2018/0078275 A1 | 3/2018 | Esarey et al. |

FOREIGN PATENT DOCUMENTS

| | | |
|---|---|---|
| WO | WO 1991/17715 | 11/1991 |
| WO | WO 2004/022290 | 3/2004 |
| WO | WO 2007/034438 | 3/2007 |
| WO | WO 2015/195666 | 12/2015 |
| WO | WO 2016/196206 | 12/2016 |

OTHER PUBLICATIONS

Ameer, et al., "Evolution of Instruments for Harvest of the Skin Grafts," Indian Journal of Plastic Surgery Jan.-Apr. 2013; 46(1); pp. 28-35.

PCT International Search Report and Written Opinion dated Jul. 29, 2016 for PCT/US2016/034370, International Filing Date May 26, 2016. PCT International Application No. PCT/US2016/034370 corresponds to U.S. Appl. No. 14/725,303, filed May 29, 2015, now U.S. Pat. No. 10,022,146 on Jul. 17, 2018. The present application claims priority from U.S. Appl. No. 14/725,303. (10 pages).

PCT International Search Report and Written Opinion dated Feb. 22, 2018 for PCT International Application No. PCT/US2017/063418, International filing date Nov. 28, 2017. PCT/US2017/063418 corresponds to U.S. Appl. No. 15/823,528, filed Nov. 27, 2017, now U.S. Pat. No. 10,537,356 on Jan. 21, 2020. The present application claims priority from U.S. Appl. No. 15/823,528. (12 pages).

PCT International Search Report and Written Opinion dated Jul. 24, 2015 for PCT/US2015/036034, International Filing Date Jun. 16, 2015. PCT International Application No. PCT/US2015/036034 corresponds to U.S. Appl. No. 14/741,021, filed Jun. 16, 2015. The present application claims priority from U.S. Appl. No. 14/741,021. (13 pages).

Catalog entitled "Ball Bearing Cages", Publication No. WLK 100 E, Publication Date—Sep. 2004, Published by International Customized Bearings. (34 pages).

Operators Manual for Integra Model C Air Dermatome Manufactured by Integra LifeSciences Corporation, Copyright 2009, Cincinnati, OH (82 pages).

Instruction Manual for Zimmer™ Air Dermatome, Manufactured by Zimmer Surgical, Inc., Dover, OH, Copyright 1992 (127 pages).

Operators Manual, Integra TM, Model SB Dermatome, Manufactured by Integra LifeSciences Corporation, Plainsboro, New Jersey, Copyright 2005 (6 pages).

Informational Brochure for Humeca Dermatome Blades, Manufactured by Humeca BV, Enschede, The Netherlands, publication date Oct. 2008 (1 page).

Image of Super Gyros Knife-Metal, manufactured by Optimal Automatics, Inc., Chicago, IL. Advertisement [online]. Retrieved from the Internet: URL:http://www.autodoner.com/autodoner/products/gyro-knife/super-gyros-knife-metal.aspx. The Super Gyros Knife depicted in the Internet printout is prior art to the present application. (3 pages).

14 Photographs of Super Gyros Knife, Model P, Manufactured by Optimal Automatics, Inc., Chicago, IL. The Super Gyros Knife depicted in the 6 photos is prior art to the present application (6 pages).

3 Photographs of Power Operated Gyros Knife, Manufacturer, Unknown. The Power Operated Gyros Knife depicted in the 3 photographs is prior art to present application (3 pages).

Image of Super Gyros Knife-Plastic, manufactured by Optimal Automatics, Inc., Chicago, IL. Advertisement [online]. Retrieved from the Internet: URL:http://www.autodoner.com/autodoner/products/gyro-knife/super-gyros-knife-plastic.aspx. The Super Gyros Knife depicted in the Internet printout is prior art to the present application. (4 pages).

* cited by examiner

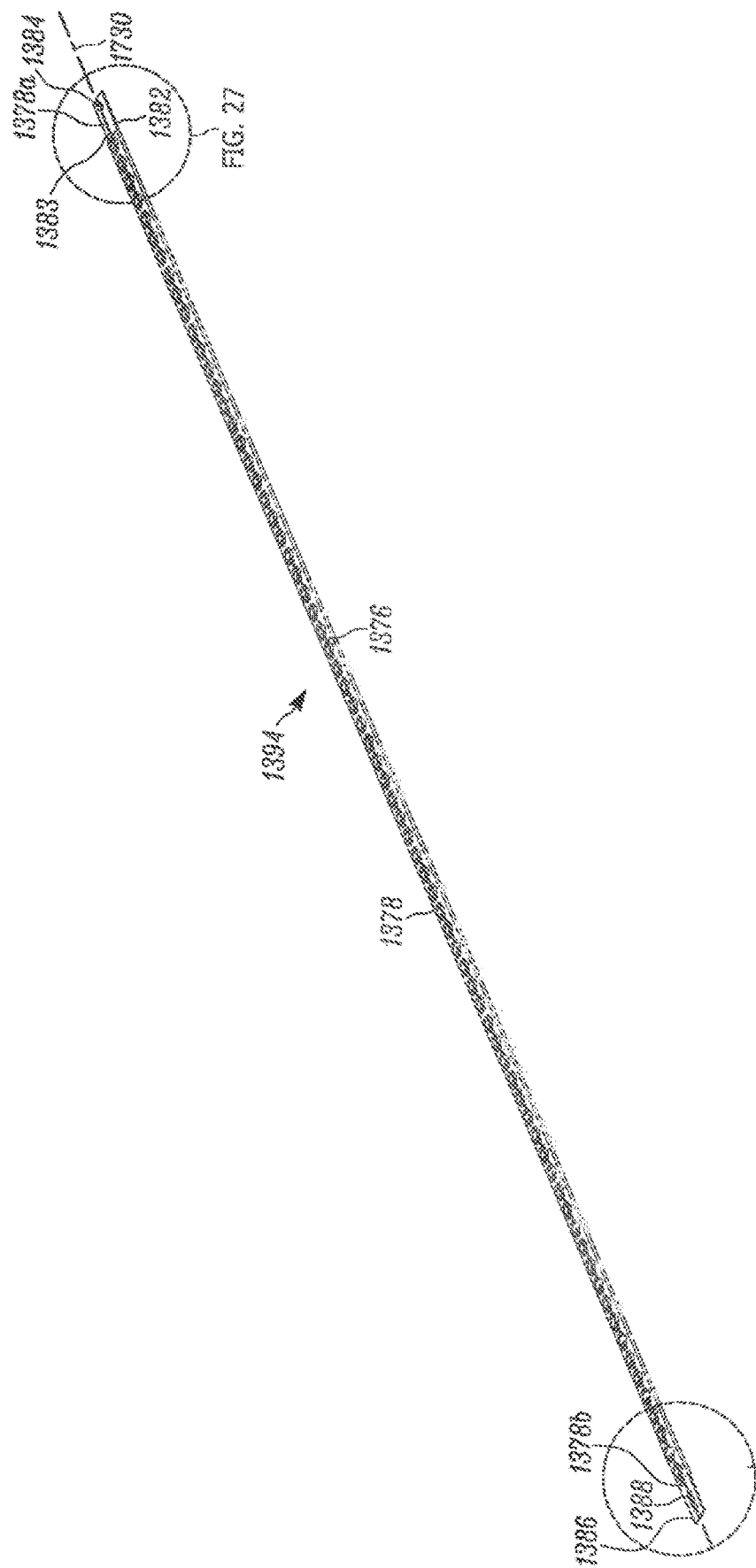

POWER OPERATED ROTARY EXCISION TOOL

CROSS-REFERENCE TO RELATED APPLICATIONS

This application claims priority under 35 USC 120 as a continuation application of parent U.S. application Ser. No. 15/823,528, filed Nov. 27, 2017, published as U.S. Pub. No. US-2018-0078275-A1 on Mar. 22, 2018, to be issued as U.S. Pat. No. 10,537,356 on Jan. 21, 2020, which claims priority under 35 USC 119(e) to U.S. Provisional Patent Application Ser. No. 62/427,148, filed Nov. 28, 2016. Parent U.S. application Ser. No. 15/823,528, filed Nov. 27, 2017 is a continuation-in-part of U.S. application Ser. No. 14/725,303, filed May 29, 2015, issued as U.S. Pat. No. 10,022,146 on Jul. 17, 2018. Parent U.S. application Ser. No. 15/823,528, filed Nov. 27, 2017 is also a continuation-in-part of U.S. application Ser. No. 14/741,012, filed Jun. 16, 2015, now abandoned, which claims priority under 35 USC 119(e) to U.S. Provisional Patent Application Ser. No. 62/012,707, filed Jun. 16, 2014. The respective entire contents of the above-identified U.S. application Ser. Nos. 15/823,528, 14/725,303, 14/741,012, 62/427,148, and 62/012,707, U.S. Publication No. US-2018-0078275-A12, and U.S. Pat. Nos. 10,022,146 and 10,537,356 are incorporated herein in their respective entireties by reference for any and all purposes.

TECHNICAL FIELD

The present invention relates generally to power operated rotary excision tools, such as power operated rotary knife dermatomes and power operated rotary disc dermatomes.

BACKGROUND OF THE INVENTION

Power operated rotary excision tools, such as power operated rotary knife dermatomes, are hand-held surgical instruments used by a physician or medical professional to cut thin layers or sections of skin tissue. Power operated rotary excision tools, such as power operated rotary knife dermatomes are used in hospitals and other medical facilities for excising or removal of skin tissue from patients in connection with various medical procedures including split-thickness and full-thickness skin grafting, skin debriding (e.g., removal of burned skin tissue), tumor/lesion removal, and breast reduction, among other procedures. Power operated rotary excision tools, such as power operated rotary knife dermatomes are also used to remove skin tissue from deceased human or animal donors for skin grafting purposes.

Prior power operated dermatomes typically included a reciprocating cutting blade disposed at a front or leading edge of the dermatome with a guard or depth gauge to allow the operator to set a depth of cut to remove a desired thickness of skin tissue. The handle of prior dermatomes was disposed rearward of the cutting direction of the blade. Such dermatome configurations required the operator to move the dermatome away from the his body while cutting, resulting in reduced visibility of the area of skin to be removed, and less precise control of the dermatome.

SUMMARY

In one aspect, the present disclosure relates to a blade housing assembly for rotatably supporting an annular rotary, knife blade for rotation about a central axis of rotation in a power operated dermatome, the blade housing assembly comprising: an annular blade housing including an upper end and an axially spaced apart lower end and an inner wall and a radially spaced apart outer wall and including a shield extending radially inwardly from a blade receiving body, the annular blade housing centered about an axially extending center line, the blade receiving body including a blade channel extending axially upwardly from a lower surface of the blade receiving body, the blade channel including a first wall, a radially spaced apart second wall closer to the axially extending center line, and a bridging portion between the first and second walls, a bearing surface formed on the first wall, the blade receiving body further includes a threaded portion formed on the outer surface of the annular blade housing, the shield including an inner wall defining a tissue directing surface, the tissue directing surface including a first tissue guide surface extending upwardly from a lower end of the shield, the first tissue guide surface extending substantially parallel to the axially extending center line of the annular blade housing; and an annular blade lock ring including an upper end and an axially spaced apart lower end and an inner wall and a radially spaced apart outer wall, the inner wall including a threaded portion threadedly engaged with the threaded portion of the blade receiving body of the annular blade housing to releasably secure the annular blade lock ring to the annular blade housing, the inner wall further including a bearing surface.

In another aspect, the present disclosure relates to a blade housing assembly for rotatably supporting an annular rotary knife blade for rotation about a central axis of rotation in a power operated rotary excision tool, the blade housing assembly comprising: an annular blade housing including an upper end and an axially spaced apart lower end and an inner wall and a radially spaced apart outer wall, the annular blade housing centered about an axially extending center line, the blade housing including a circumferentially extending skin deflector portion including a blade receiving body and a shield extending radially inwardly from the blade receiving body, the blade receiving body including a blade receiving channel extending axially upwardly from a lower surface of the blade receiving body and radially spaced from the inner and outer walls of the annular blade housing, the blade receiving channel includes a first wall, a radially spaced apart second wall closer to the axially extending center line of the blade housing, and a bridging surface between the first and second walls, the first wall includes a first generally planar portion extending substantially parallel to the axially extending center line of the blade housing and a second offset portion, the second offset portion defining a bearing surface extending transverse to the axially extending center line of the blade housing, the shield including an inner wall defining a tissue directing surface, the tissue directing surface including a first tissue guide surface extending upwardly from a lower end of the shield, the first tissue guide surface extending substantially parallel to the axially extending center line of the annular blade housing; and an annular blade lock ring releasably secured to the annular blade housing.

In another aspect, the present disclosure relates to a power operated dermatome comprising: an annular rotary knife blade supported for rotation about a central axis of rotation by a blade housing assembly, the annular rotary knife blade including: an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade; and a continuous rolling bearing structure received within the bearing race of the outer wall of the rotary knife blade, the continuous rolling bearing structure forming a convex outer surface of the rotary knife blade projecting radially outwardly from the outer wall of rotary knife blade; and the blade housing assembly including: an annular blade housing including an upper end and an axially spaced apart lower end and an inner wall and a radially spaced apart outer wall, the annular blade housing centered about an axially extending center line, the blade housing including a circumferentially extending skin deflector portion including a blade receiving body and a shield extending radially inwardly from the blade receiving body, the blade receiving body including a blade receiving channel extending axially upwardly from a lower surface of the blade receiving body and radially spaced from the inner and outer walls of the annular blade housing, the blade receiving channel includes a first wall, a radially spaced apart second wall closer to the axially extending center line of the blade housing, and a bridging surface between the first and second walls, the first wall includes a first generally planar portion extending substantially parallel to the axially extending center line of the blade housing and a second offset portion, the second offset portion defining a bearing surface extending transverse to the axially extending center line of the blade housing, the shield including an inner wall defining a tissue directing surface, the tissue directing surface including a first tissue guide surface extending upwardly from a lower end of the shield, the first tissue guide surface extending substantially parallel to the axially extending center line of the annular blade housing.

BRIEF DESCRIPTION OF THE DRAWINGS

These and other features and advantages of the present invention will become better understood with regard to the following description and accompanying drawings in which:

FIG. 25 is a schematic perspective view of a rolling bearing strip of the head assembly of the power operated dermatome of FIG. 8 in a linear segment condition prior to having interlocking ends of a separator cage of the rolling bearing strip being fused together;

DETAILED DESCRIPTION

Figure 1:
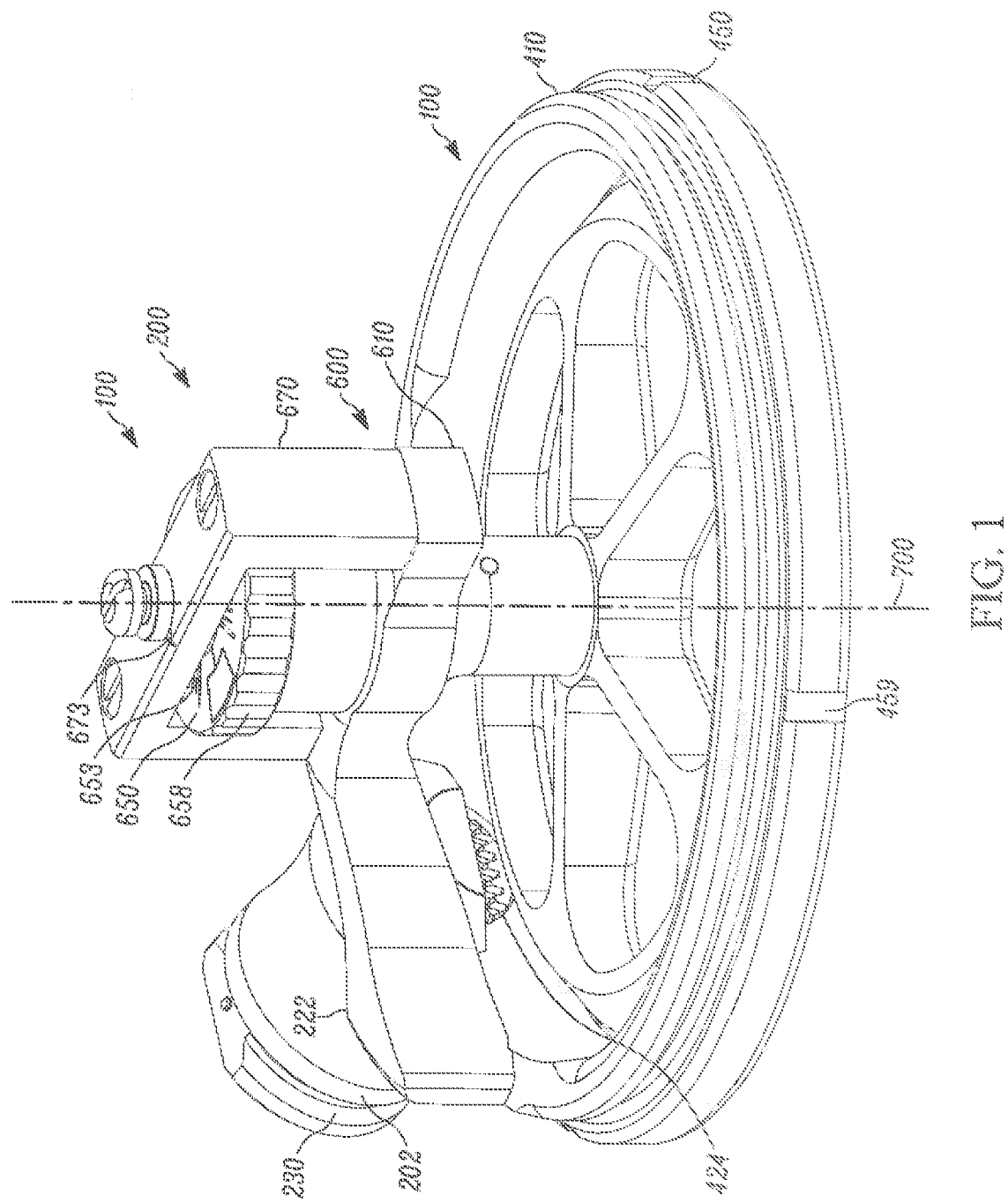
FIG. 1 is a schematic perspective view of an exemplary hand held, power operated rotary excision tool, namely, a hand held, power operated rotary knife dermatome.
Figure 2:
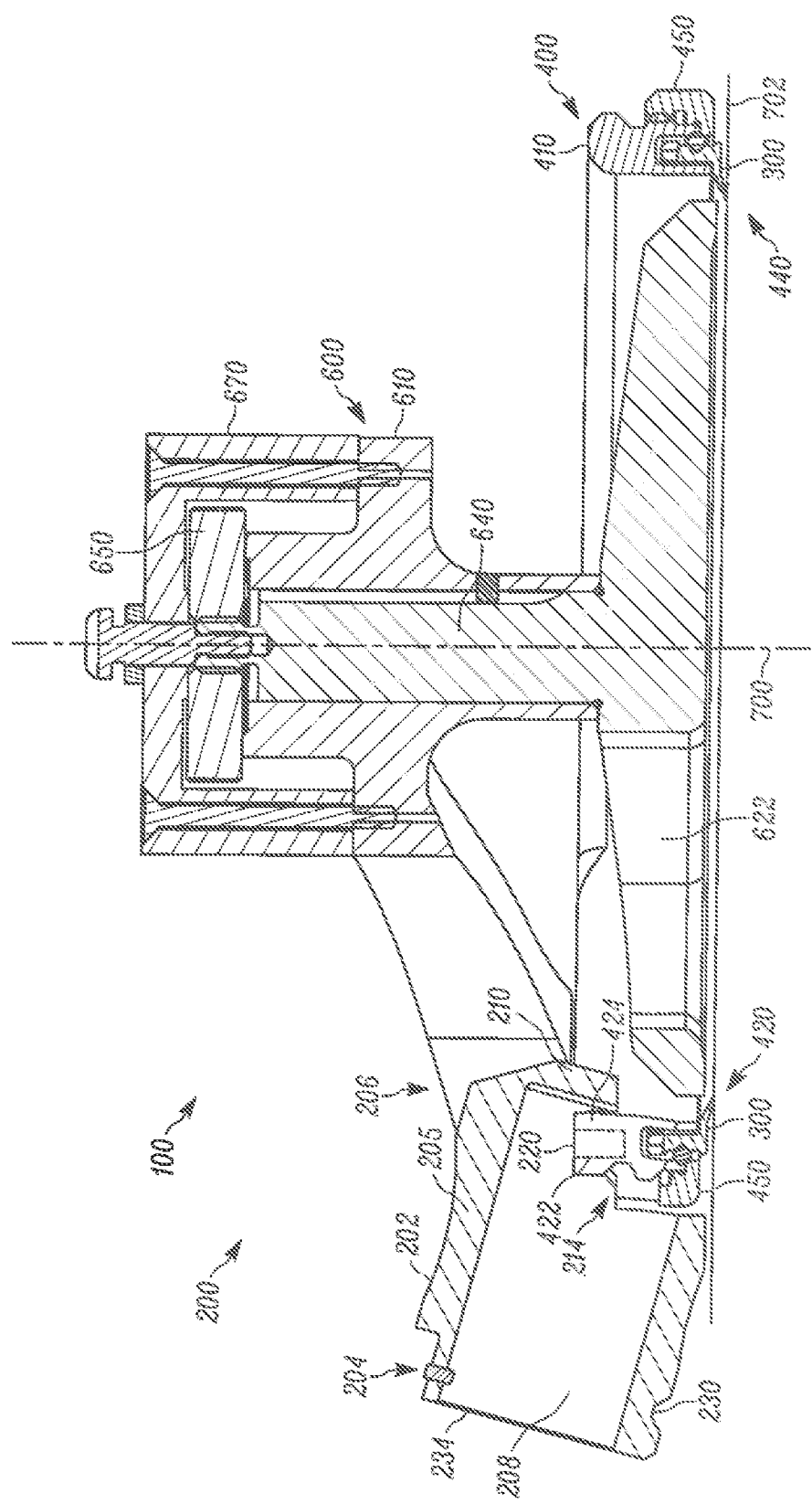
FIG. 2 is a schematic cross-section of the exemplary dermatome of FIG. 1.
Figure 3:
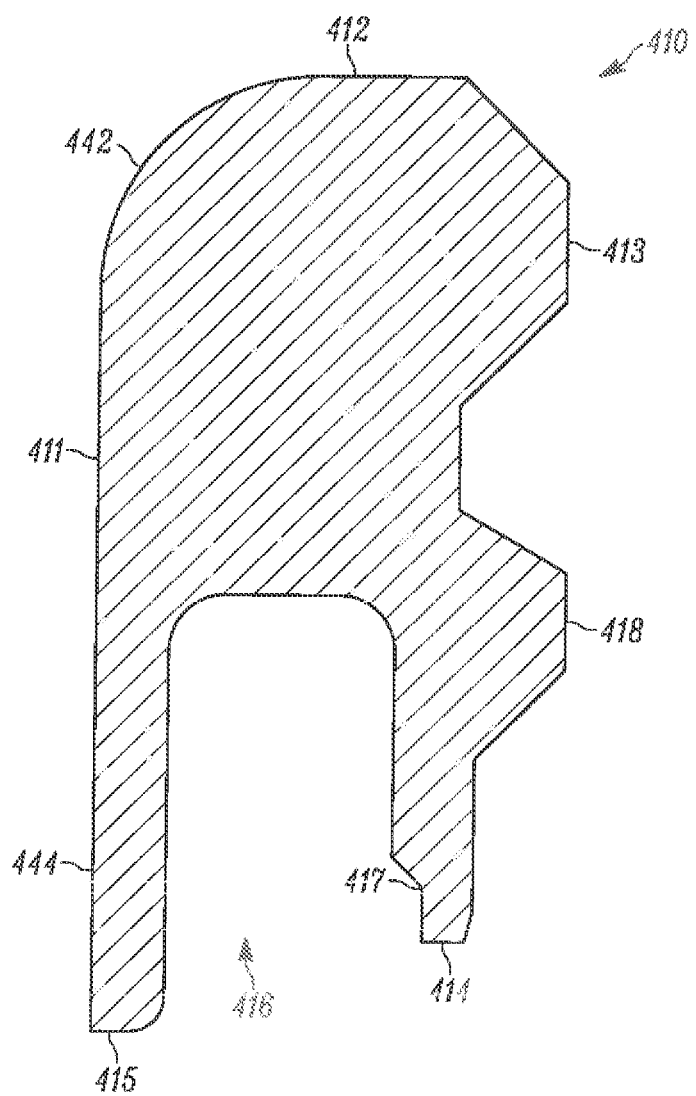
FIG. 3 is a schematic enlarged view of a cross-section of annular blade housing 410.
Figure 4:
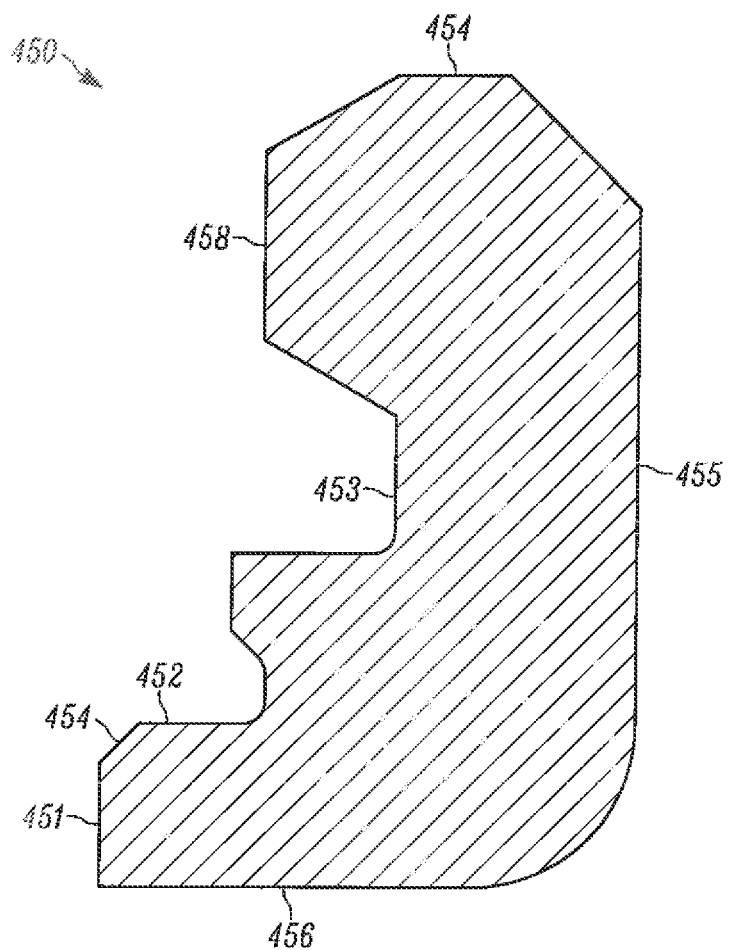
FIG. 4 is a schematic enlarged view of a cross-section of lock ring 450.

FIGS. 1 through 7 illustrate an exemplary embodiment of a head assembly 200 of a hand-held, power operated rotary excision tool, such as a hand-held, power operated rotary knife dermatome, alternately referred to as a hand-held, power operated dermatome 100. The power operated dermatome 100 comprises a handle assembly (not shown), a drive assembly (not shown), and a head assembly 200. The head assembly 200 includes a frame body 202, an annular rotary knife blade 300, a blade housing assembly 400, and a depth gauge 600. The cross-section of FIG. 2 is taken through the above components to more clearly indicate their relative position inside of the head assembly 200 of the dermatome 100.

Figure 6:
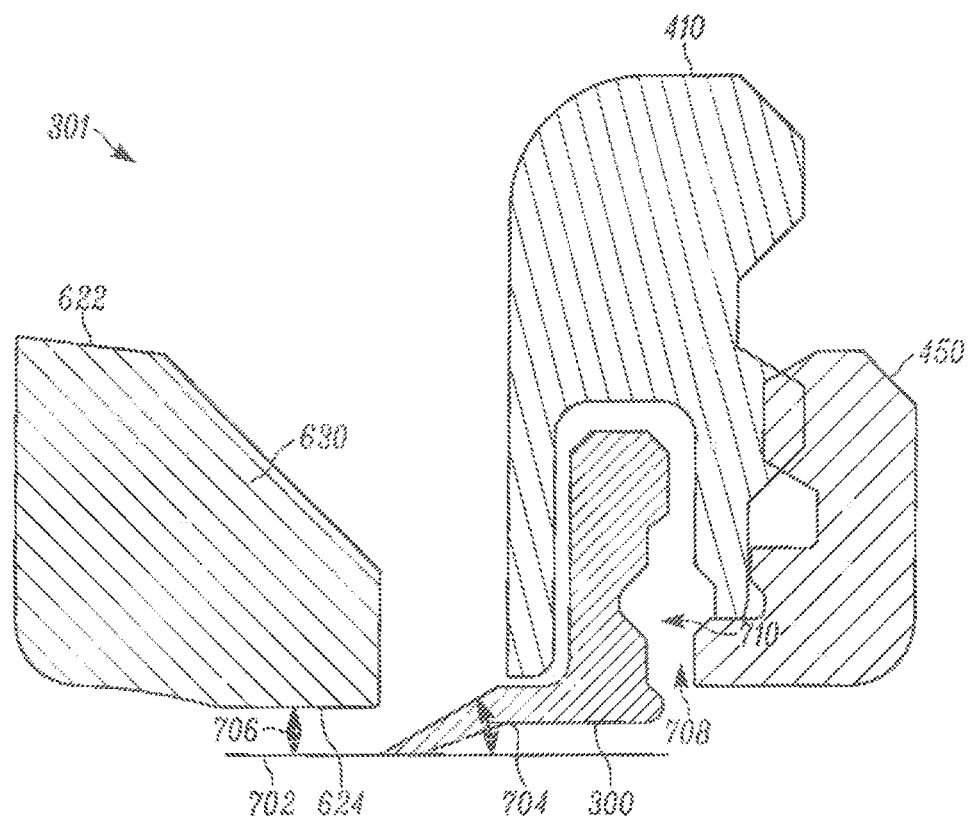
FIG. 6 is a schematic enlarged view of a cross-section of blade housing assembly 400.
Figure 7:
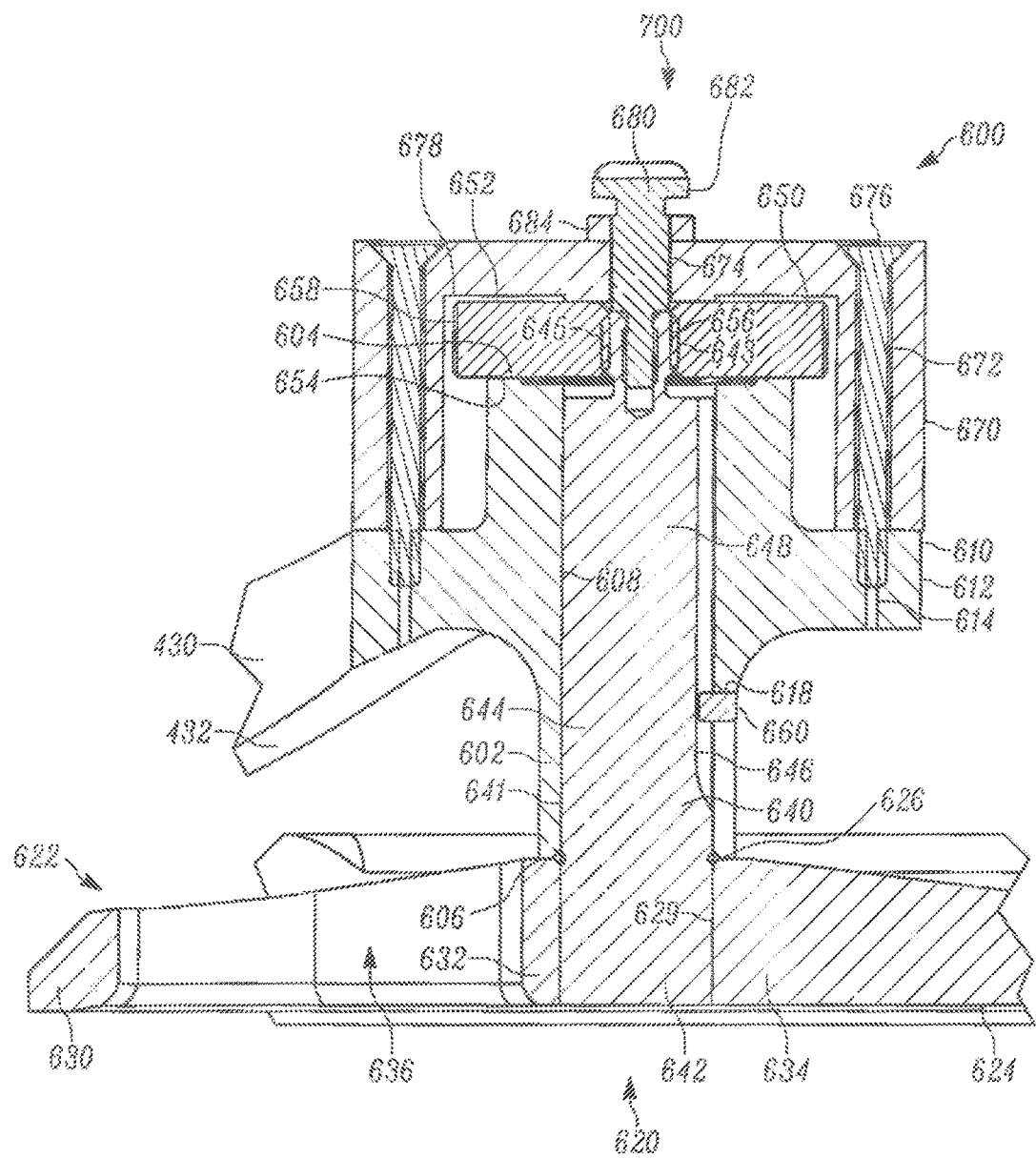
FIG. 7 is a schematic enlarged view of a cross-section of depth gauge assembly 600.
Figure 8:
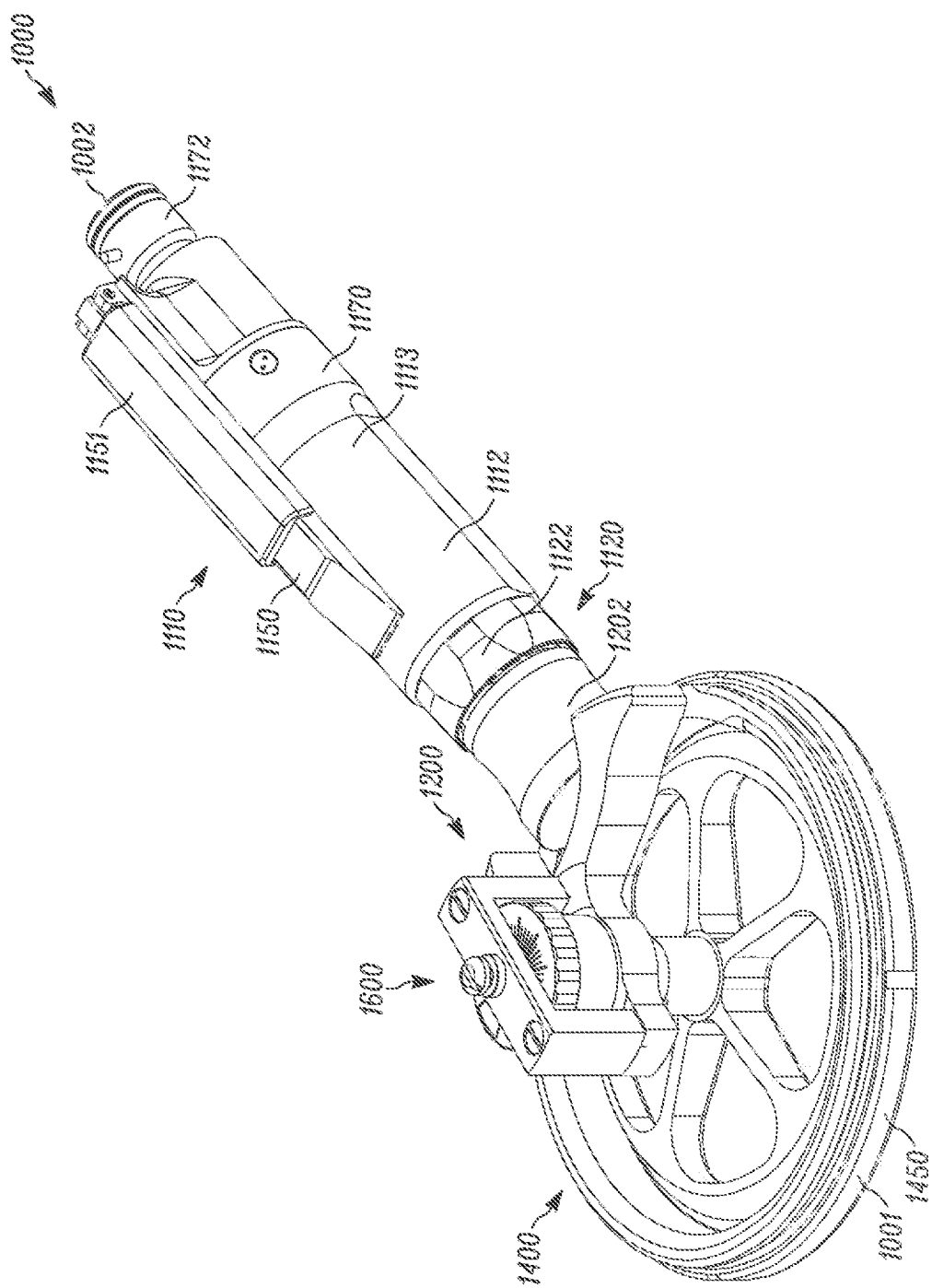
FIG. 8 is a schematic front perspective view of a second exemplary embodiment of a hand-held, power operated rotary excision tool, namely, hand-held, power operated rotary knife dermatome constructed in accordance with another example embodiment of the present disclosure including a head assembly releasably affixed to an elongated handle assembly, the head assembly including an annular rotary knife blade, a blade housing assembly supporting the annular rotary knife blade for rotation about a central axis of rotation, the blade housing assembly including an annular blade housing and an annular lock ring, and a depth gauge assembly for adjustably setting a depth of cut of the power operated dermatome.
Figure 9:
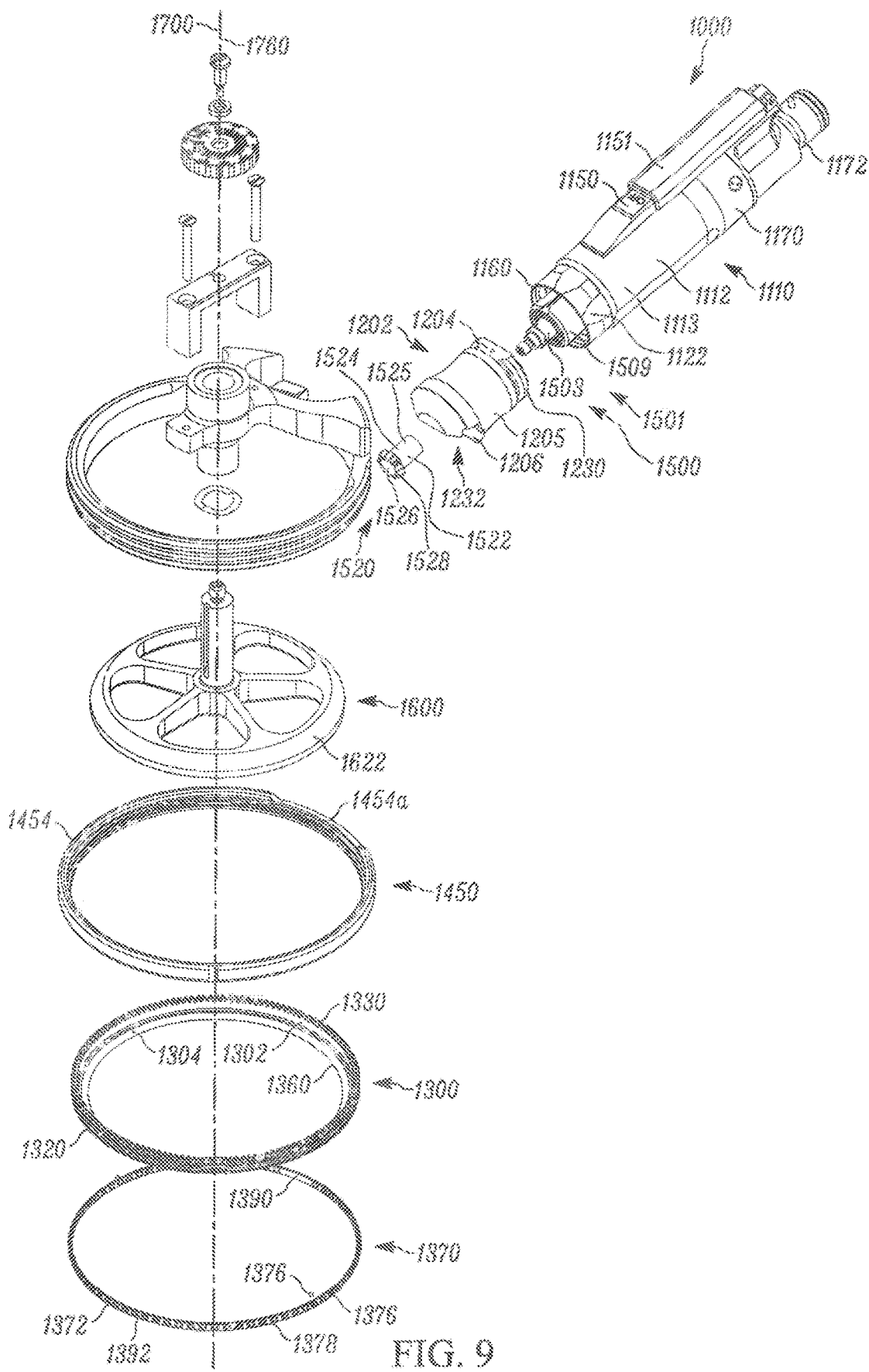
FIG. 9 is a schematic exploded front perspective view of the power operated dermatome of FIG. 8.

During operation of the dermatome 100, the rotary knife blade 300 is driven around an axis of rotation 700 at high rotational speed (on the order of about 500-1,500 RPM) by the drive assembly. As shown in FIG. 6, the cutting edge 360 of the rotary knife blade 300 forms a cutting plane 702 that is substantially orthogonal to axis of rotation 700. A lower blade portion 304 of the rotary knife blade 300 is generally frustoconical in shape, defining a cutting angle 704 with the cutting plane 702. During operation of the dermatome 100, the cutting edge 360 cuts into the skin of a patient at the cutting angle 704 until a bottom surface 624 of the depth gauge plate 622 of the depth gauge assembly 600 contacts the patient's body. An axial distance between the bottom surface 624 and the cutting plane 702 defines a depth of cut 706 that corresponds to a maximum thickness skin excised during use of the dermatome 100. An adjustment knob 650 of the depth gauge assembly 600 allows the user to quickly and precisely set and adjust the axial position of the bottom surface 624, thereby adjusting the depth of cut 706. The depth of cut 706 can be adjusted during a cutting operation to vary the thickness of the portion of skin excised from the patient.

The dermatome 100 operates in a manner similar to that of the power operated dermatome disclosed in U.S. patent application Ser. No. 13/842,224 (hereinafter "the '224 application") filed on Mar. 15, 2013 and entitled Power Operated Dermatome With Shielded Rotary Knife Blade, which is incorporated herein by reference in its entirety.

The frame body 202 connects a handle assembly (not shown) to the blade housing assembly 400 of the head assembly 200. The frame body 202 comprises a generally cylindrical body 205 and includes a rearward handle attachment portion 204 and a forward interface portion 206. The interface portion 206 of the frame body 202 includes an end portion 210. The end portion 210 and the body 205 include an opening 214 configured to receive the interface portion 420 of the annular blade housing 410. The rearward attachment portion 204 includes a threaded outer surface 230 located in the handle attachment portion 204 to attach the frame body 202 to the handle assembly. The head assembly 200 can be attached to the handle assembly by any releasable means, such as with a flange and fasteners, a quarter-turn collar, latches, a compression fit, or the like.

The frame body 202 also includes a gear box housing 208 that houses a gear train (not shown) of the drive assembly. The drive assembly is disposed within the handle assembly and gear box housing 208. The rear opening 234 in the frame body 202 allows the drive assembly to be inserted into the gear box housing 208 of the frame body 202 when the handle assembly is attached to the frame body 202. Exemplary handle and drive assemblies are disclosed in the '224 application.

The blade housing assembly 400 includes an annular blade housing 410 and a lock ring 450. The annular blade housing 410 is generally cylindrical in shape and includes a rear interface portion 420 and a forward skin deflector portion 440. The housing 410 has an inner wall 411 radially spaced apart from an outer wall 413. An outer lower end 414 is axially spaced apart from an upper end 412 and intersects with the outer wall 413. An inner lower end 415 is axially spaced apart from the upper end 412 and intersects with the inner wall 411. An annular blade channel 416 is disposed between the outer and inner lower ends 414, 415. An arcuate bearing surface 417 is located where the outer lower end 414 meets the annular blade channel 416. The outer wall 413 includes a threaded portion 418 for assembly with the lock ring 450.

The interface portion 420 of the annular blade housing 410 includes a gear interface opening 424 that intersects the upper end 412, inner wall 411, and outer wall 413 to expose the driven gear 330 of the rotary knife blade 300 disposed within the annular channel 416. The forward interface portion 206 of the frame body 202 attaches to the interface portion 420 of the housing 410 in the location of the openings 424, 214. The gear interface opening 424 in the blade housing 410 and the opening 214 in the frame body 202 allow the drive train (not shown) within the frame body 202 to interface with the driven gear 330 of the rotary knife blade 300. The interface slot 220 in the forward interface portion 206 of the frame body 202 receives the upper end 412 of the interface portion 420 of the blade housing 410. In one particular embodiment, the frame body 202 is secured to the annular housing 410 with fasteners 222 threaded into threaded openings 422 in the interface portion 420 of the housing 410. The frame body 202 may be attached to the housing 410 by any releasable means, such as with pins, clamps, or the like.

The skin deflector portion 440 of the annular blade housing 410 includes: a blade shield 444 comprising an inner wall 411 and an inner lower end 415; and a rounded guide surface 442 comprising an inner wall 411 and an upper end 412. The blade shield 444 covers the body portion 302 of the rotary knife blade 300 so that the driven gear 330 disposed within the blade channel 416 is not exposed during operation of the dermatome 100. The rounded guide surface 442 is formed at the intersection of the inner wall 411 and upper end 412 and prevents excised skin from tearing as it is removed from the dermatome 100 during operation.

The blade housing assembly 400 farther includes a depth gauge support portion 430. The depth gauge support 430 includes one or more ribs 432 that connect the depth gauge assembly 600 and the blade housing assembly 400 to align the center of the depth gauge assembly 600 with the axis of rotation 700. The gauge support portion 430 is integrally part of the blade housing 410, but the gauge support 430 may comprise separate components attached to the blade housing 410 by any means, such as with threaded fasteners, clamps, pins, a welded connection, or the like. The gauge support 430 may also attach to the blade housing 410 in one or more locations, provided that room is left between the ribs 432 in the skin deflector portion 440 of the annular housing 410 for excised skin to be extracted from the dermatome 100 during operation, and provided that the depth gauge assembly 600 is adequately supported during operation of the dermatome 100.

The lock ring 450 is generally cylindrical in shape and includes an upper end 454, an axially spaced apart lower end 456, a lower inner surface 451, an upper inner surface 453, and an outer surface 455. The upper and lower inner surfaces 453, 451 are radially spaced apart from the outer surface 455. The lower inner surface 451 is disposed inward of the upper inner surface 453, forming a shoulder 452. An arcuate bearing surface 457 is formed at the intersection of the lower inner surface 451 and the shoulder 452. The upper inner surface 453 includes a threaded portion 458 to assemble the lock ring 450 to the threaded portion 418 of the annular blade housing 410. The outer surface 455 includes peripherally spaced cavities 459 so that the lock ring 450 can be held securely during assembly with the blade housing 410. Though the lock ring 450 is attached to the blade housing 410 with a threaded connection, the lock ring 450 may be attached to the blade housing 410 by any releasable means, such as with threaded fasteners, pins, clamps, or the like.

The rotary knife blade 300 includes an upper body portion 302 and a lower blade portion 304. The upper body portion 302 extends between an upper end 306 and a lower end 308, and includes an inner wall 310 and an outer wall 312. The outer wall 310 includes a bearing race 320 and an arcuate bearing surface 322 that extend radially inward into the outer wall 312 to receive a continuous rolling bearing structure 370. When assembled within the bearing race 320, the bearing structure 370 defines a convex outer surface 380 of the rotary knife blade 300 that projects radially outward from the outer wall 312. The continuous rolling bearing structure 370 supports the rotary knife blade 300 within the blade housing assembly 400. Specific details concerning the structure and configuration of the continuous rolling bearing structure 370 are disclosed in the '224 application and U.S. Pat. No. 8,806,761 (hereinafter "the '761 patent") filed on Jul. 25, 2011 and entitled Power Operated Rotary Knife, which is incorporated herein by reference in its entirety.

The bearing structure 370 is disposed in an annular gap 708 defined between opposing faces of the rotary knife blade 300, blade housing 410, and blade lock ring 450 of the blade housing assembly 400, in the region of the rotary knife blade bearing race 320. Specifically, the plurality of ball bearings (not shown) of the bearing structure 370 are disposed within an annular passageway 710, which is generally circular in cross section and defined by the opposing arcuate bearing surfaces 322, 417, and 457 of the rotary knife blade 300, blade housing 410, and lock ring 450, respectively.

The lower blade portion 304 of the rotary knife blade 300 extends from an upper end 350 to a lower end 352, and includes an inner wall 354 and a radially spaced apart outer wall 356. The inner and outer walls 354, 356 are generally frustoconical, converging in a direction proceeding downwardly toward the cutting edge 360 of the rotary knife blade 300. The inner wall 310 of the body portion 302 and the inner wall 354 of the blade portion 304 are connected by a shoulder surface 314 and combine to define an inner region 301 of the rotary knife blade 300. A bottom surface 362 defines the lower end 352 of the blade portion 304, connecting the inner and outer walls 354, 356. The cutting edge 360 is defined by the intersection of the bottom surface 362 and the inner wall 354 and is generally circular in nature. A plane aligned with the cutting edge 360 of the rotary knife blade 300 defines the cutting plane 702 of blade 300. The cutting angle 704 is defined as the acute angle between the inner wall 354 of the blade portion 304 and the cutting plane 702.

Figure 5:
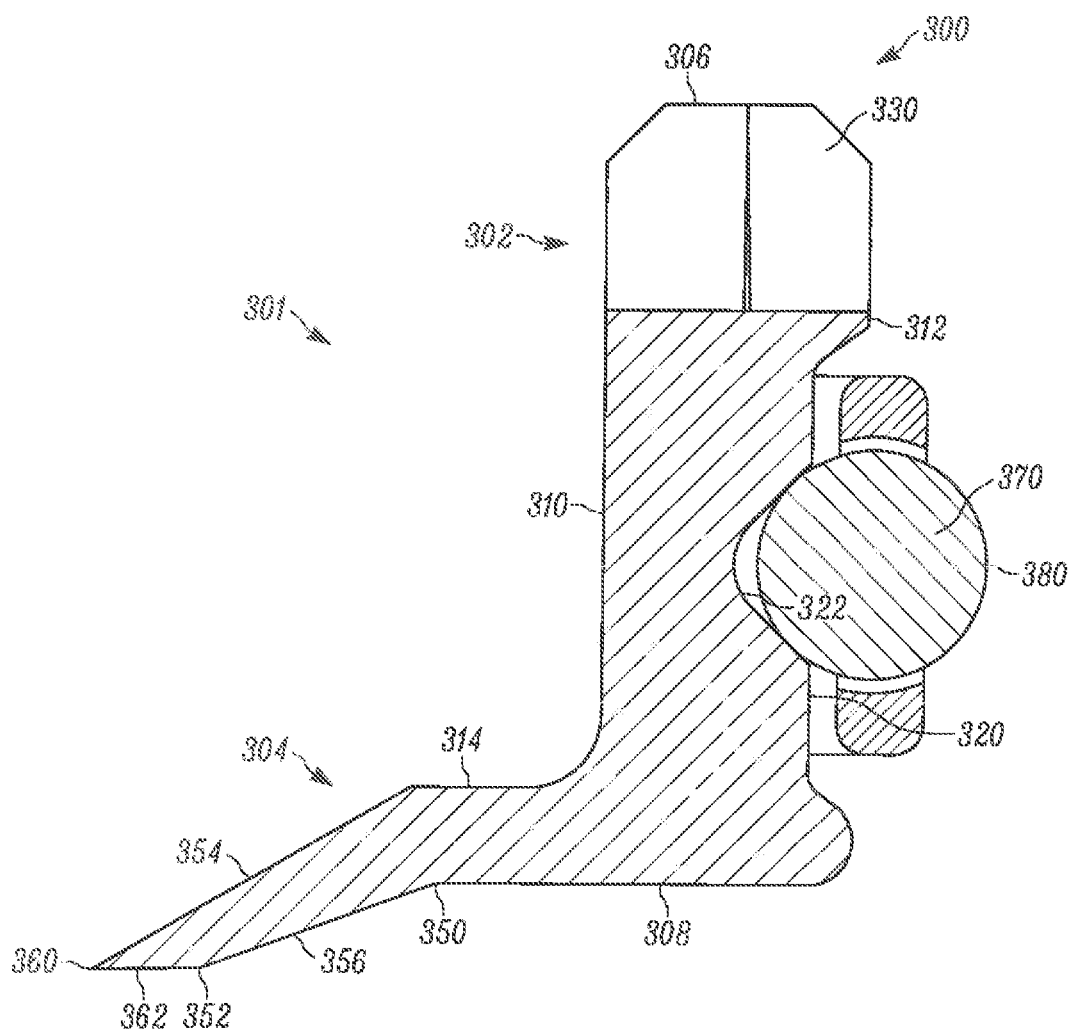
FIG. 5 is a schematic enlarged view of a cross-section of rotary knife blade 300.
Figure 5A:
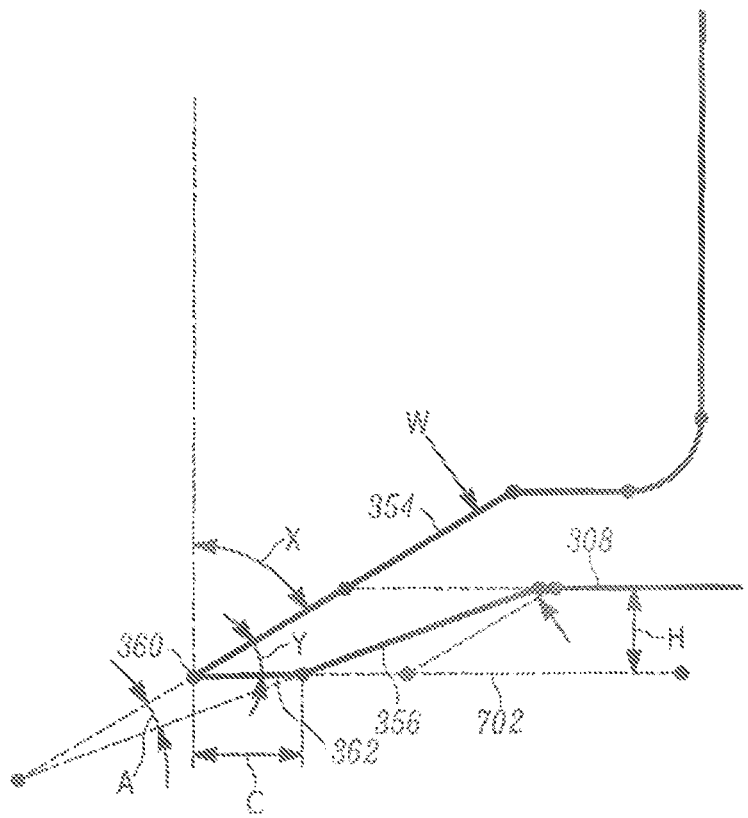
FIG. 5A is a schematic diagram of a portion of the cross-section of rotary knife blade 300 of FIG. 5.

The relationship between the various surfaces of the lower blade portion 304 is illustrated in FIG. 5A. Before the lower blade portion 304 of the rotary knife blade 300 is formed by a grinding operation, the thickness of the material W may range from about 0.005" to about 0.1". In one particular embodiment, the thickness of the material W is about 0.034". A height distance H from the cutting plane 702 to the lower end 308 of the upper body portion 302 of the rotary knife blade 300 may range from about 0.01" to about 1". In one particular embodiment, the height distance H is about 0.03".

A blade angle X between the inner wall 354 of the lower blade portion 304 and a vertical line extending from the cutting edge 360 may range from about 20 degrees to an angle approaching 90 degrees. In one particular embodiment, the blade angle X is about 60 degrees. The lower blade portion 304 is ground to bring the bottom surface 362 within a desirable range for a chisel grind width C, which may be up to about 0.106". In one particular embodiment, the chisel grind width C is about 0.037". In some other embodiments, the inner and outer walls 354, 356 are joined at the cutting edge 360 so that there is no bottom surface 362. To the extent that a bottom surface 362 exists in these other embodiments, the chisel grind width C is at most 0.001".

After these grinding operations, a taper angle A between the inner and outer walls 354, 356 is an acute angle, that is, it is greater than 0 and less than 90 degrees. In one particular embodiment, the taper angle A is about 10 degrees. The bottom surface 362 is then ground to a sharpened edge angle Y to create the cutting edge 360 and provide a bottom surface 362 that is more suitable for sliding over the skin of a patient during a cutting operation. The sharpened edge angle Y between the bottom surface 362 and the inner wall 354 is greater than 0 degrees and up to about 70 degrees. In one particular embodiment, the sharpened edge angle Y is about 29 degrees.

Figure 5B:
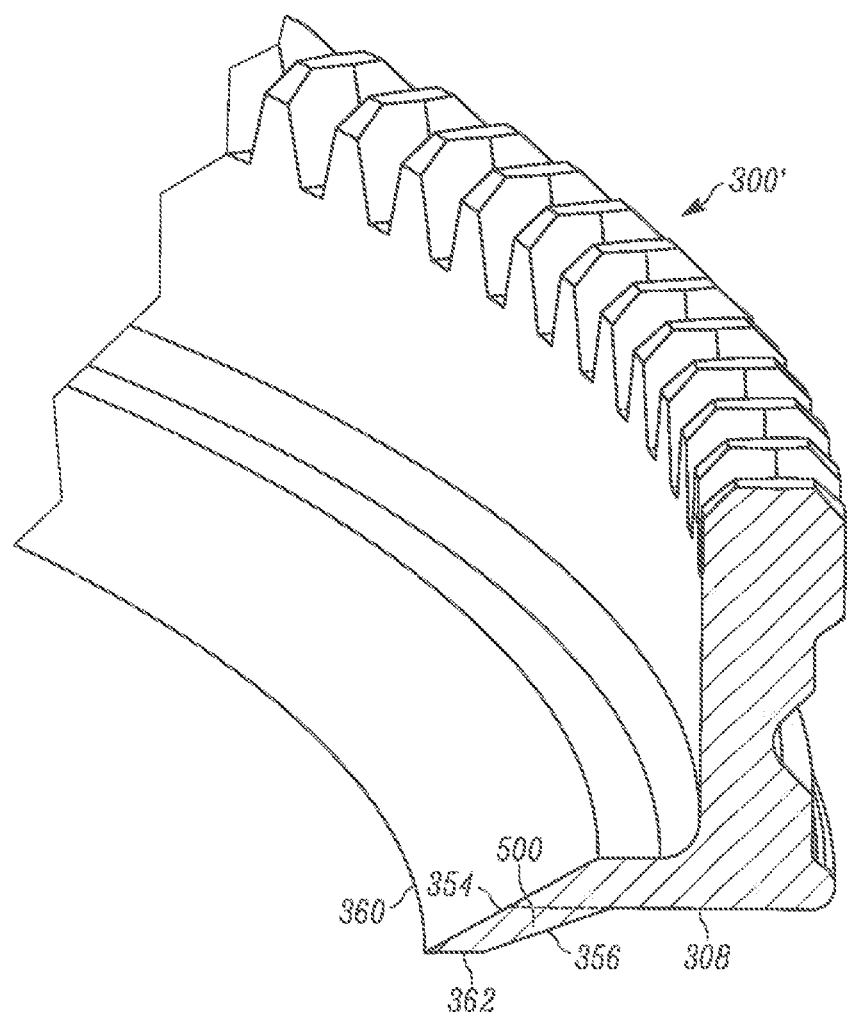
FIG. 5B is a schematic perspective view of the cross-section of rotary knife blade 300 of FIG. 5.

As can be seen from FIG. 5A, the surfaces of the lower blade portion 304 form a quadrilateral shape 500 without any parallel sides that is bounded by the inner and outer walls 354, 356 of the lower blade portion 304, the bottom surface 362, and a line extending from the lower end 308 of the upper body portion 302. This shape is swept through a full revolution around the axis of rotation 700 to create the rotary knife blade 300. A partially swept shape is shown in FIG. 5B to illustrate how the surfaces of FIG. 5B form the blade 300. The dimensions noted above are maintained throughout the blade to ensure that all portions of the blade 300 are consistent in their cutting performance.

The depth gauge assembly 600 includes a cylindrical depth gauge support 610 and the depth gauge 620. The depth gauge support 610 further includes a flange 612, a cylindrical support 602, and a stop plate 670. The depth gauge 620 includes a depth gauge plate 622, a shaft 640, and an adjustment knob 650. The depth gauge plate 622 is disposed within an inner region 301 of the blade 300. A depth of cut 706 is defined by the axial distance between the cutting plane 702 and the bottom surface 624 of the depth gauge plate 622. The depth of cut 706 determines the thickness of the skin excised by the dermatome 100 during use. As with the depth gauge of the '224 application, the depth gauge assembly 600 allows the operator to quickly and accurately change the depth of cut 706 during operation of the dermatome 100 by rotating the adjustment knob 650.

The depth gauge flange 612 extends from and is supported by the one or more ribs 432 of the blade housing support portion 430 and is generally rectangular, though it may be any shape. The cylindrical support 602 extends below the flange 612 to the lower end 606. The central bore 608 extends from the upper surface 604 of the flange 612 through the flange 612 and the cylindrical support 602 to the lower end 606. The depth gauge 620 includes the depth gauge plate 622 and the depth gauge shaft 640. The shaft 640 is slideably disposed within the central bore 608 and includes an outer surface 641, a lower end 642, a middle portion 644, and an upper end 648. The outer surface 641 of the shaft 640 includes a threaded adjustment portion 643 at the upper end 648 and an axially oriented slot 646. The upper end 648 includes a threaded opening 645 to receive a stop screw 680.

The stop plate 670 is generally rectangular and assembles to the depth gauge flange 612. The stop plate 670 includes an adjustment knob opening 678 that is configured to receive an adjustment knob 650 and limit vertical movement of the adjustment knob 650 when the depth of cut 706 is adjusted by an operator. The stop plate 670 further includes two openings 672 that are aligned with the threaded openings 614 in the depth gauge flange 612. Threaded fasteners 676 are inserted through the openings 672 and into the threaded openings 614 to secure the stop plate 670 to the flange 612. The stop plate 670 may be attached to the depth gauge flange 612 in any way, such as with clamps, pins, a welded connection, or the like.

The adjustment knob 650 is generally cylindrical and extends from the top surface 652 to the bottom surface 654. Upward movement of the adjustment knob 650 is limited by contact of the top surface 652 with the opening 678 in the stop plate 670, and downward movement of the adjustment knob 650 is limited by contact of the bottom surface 654 with the upper surface 604 of the flange 612. The knob 650 includes a threaded opening 656 for receiving a threaded adjustment portion 643 of the shaft 640. A peripheral surface 658 of the knob 650 includes a plurality of indentations to provide the operator with a better grip of the knob 650 when making adjustments to the depth of cut 706. An opening 618 in the cylindrical support 602 receives a dowel pin 660 that slideably engages the slot 646 of the shaft 640, preventing the shaft 640 from rotating as the adjustment knob 650 is rotated during adjustment of the depth of cut 706. As a result, rotational motion of the adjustment knob 650 is translated to linear vertical motion of the shaft 640 within the bore 608. The rotation of shaft 640 may be prevented by any means, such as with a keyed slot, using a non-circular shaft and bore, or the like. The top surface 652 of the knob 650 and the stop plate 670 include markings or indicia 653, 673 that indicate the current setting of the depth of cut 706, similar to those disclosed in the '224 application.

The stop plate 670 also includes a central opening 674 that is aligned with a stop screw opening 645 of the shaft 640. The stop screw 680 is inserted through the opening 674 and threaded into the threaded opening 645. The stop screw 680 includes a screw head 682 that engages a washer 684 placed on top of the stop plate 670. The position of the stop screw 680 sets the lower limit of the vertical movement of the depth gauge 620, and also prevents the threaded adjustment portion 643 of the shaft 640 from unthreading from the threaded portion 656 of the knob 650 during adjustment of the depth of cut 706. Compression of the washer 684 during downward adjustment of the knob 650 reduces backlash in the threaded connection between the knob 650 and the shaft 640. Alternatively, a biasing spring (not shown) like that shown in the '224 application may be used to limit thread backlash during adjustment of the depth of cut 706.

The depth gauge 620 includes a depth gauge plate 622 attached to the lower end 642 of the shaft 640. The gauge plate 622 includes a generally cylindrical center portion 632 and an annular ring portion 630 connected to the center portion 632 by one or more ribs 634. Openings 636 between the one or more ribs 634 allow an operator to view the skin below the dermatome 100 during a cutting operation. The center portion 632 includes a bore 628 that receives the lower end 642 of the shaft 640. The center portion 632 of the depth gauge plate 622 may be connected to the shaft 640 by any means, such as a threaded connection, a welded connection, a pinned connection, or the like. The bottom surface 624 of the annular ring portion 630 rests on the cutting surface during operation of the dermatome 100 to help an operator maintain the set depth of cut 706. Upward movement, and therefore maximum depth of cut, is limited by contact between the upper end 626 of the center portion 632 of the gauge plate 622 and the lower end 606 of the cylindrical support 602. Further details of the cutting operation of the dermatome 100 are disclosed in the '224 application.

Successful skin excising operations depend on precision equipment and operator skill. These variables are inversely related: the less precise the dermatome, the more skill and training an operator must have to perform the operation successfully. Skin removed from the patient for a typical skin grafting operation can be as thin as about 0.005 inches and as thick as about 0.043 inches. Dermatome 100 allows the operator to accurately excise skin at a desired thickness in a way that is less dependent on the operator's skill than prior dermatomes, resulting in more reliable results from operation to operation.

The position and size of the depth gauge relative to the cutting edge and depth of cut improves the precision and consistency of the depth of the cut. The relationship of the surfaces of the cutting portion of the blade also improve consistency and ease of cutting. For example, the sharpened edge angle between the bottom surface of the blade and the inner wall of the lower blade portion provides relief behind the cutting edge of the blade, thereby reducing friction between the blade and the skin of the patient, helping to separate the excised skin from uncut skin. The angle of the bottom surface improves movement of the dermatome during a cutting operation so that the dermatome can be moved at a consistent and predictable speed across the body of the patient while removing an excised portion of skin with substantially uniform thickness at a given setting. The movement of the cutting edge is countered by the depth gauge pressing against the body of the patient, resulting in a precise and repeatable cutting of the skin during an excision operation. That is, the same setting of the adjustment knob will result in the same thickness of excised skin between operations.

Additionally, features of dermatome 100 critical to precision cutting can be machined during a single manufacturing operation, improving alignment of critical features and components. This is accomplished by the generally cylindrical shape of key components of dermatome 100.

Components of the power operated dermatome disclosed in the '224 application that are similar to the upper body portion 302 of the rotary knife blade 300, blade housing 410, and lock ring 450 are generally frustoconical in shape. In the power operated dermatome 100, however, these components have a generally cylindrical shape. Consequently, manufacturability of the blade 300, blade housing 410, and lock ring 450 is improved compared to similar components of the dermatome of the '224 application. For example, the generally cylindrical shape of the blade housing 410 allows features critical to the operation of the dermatome 100, such as the annular blade channel 416 and arcuate bearing surface 417, to be machined in a single operation resulting in more precise positioning of these features relative to each other. A skin deflector 444 can also be integrally formed into the blade housing 410 because of the blade housing's 410 generally cylindrical shape. Forming the skin deflector 444 during the same operation as the blade channel 416 results in improved alignment of the rotary knife blade 300 and the skin deflector 444, allowing excised skin to more smoothly transition from the surface of the blade 300 to the skin deflector 444.

The generally cylindrical shape of these components also increases their stiffness relative to generally frustoconical components. This increased stiffness provides blade 300 with greater resistance to warping during heat treatment of cutting edge 360, thereby improving the quality of the component and manufacturing yield.

Manufacturing advantages of generally cylindrical parts extend to the time and cost of manufacturing the components as well. For example, blade 300 can be machined from a blank formed with a stamping process that is closer to the final dimensions of the part and does not require a special chuck during machining. As a result, blade 300 is produced in less time and for lower cost than the generally frustoconical blade of the dermatome of the '224 application. Integrally forming skin deflector 444 as part of blade housing 410 also reduces manufacturing time and cost by reducing the number of components of dermatome 100.

The generally cylindrical shape of blade 300, blade housing 410, and lock ring 450 also improves handling and performance of power operated dermatome 100. The cylindrical shape of these components allows head assembly 200 to be smaller than the head assembly of the dermatome disclosed in the '224 application without reducing the diameter of cutting edge 360 of blade 300. The smaller overall size of dermatome 100 as compared to the dermatome of the '224 application provides many benefits. For example, head assembly 200 of dermatome 100 weighs less than that disclosed in the '224 application, allowing for improved maneuverability during operation. Also, the radial distance between cutting edge 360 and outer surface 455 of lock ring 450 allows an operator to excise skin closer to joints or transitions in the body than the dermatome of the '224 application.

Second Exemplary Embodiment

Power Operated Dermatome 1000

A second exemplary embodiment of a hand-held, power operated rotary excision tool, such as a hand-held, power operated rotary knife dermatome, alternately referred to herein as a power operated dermatome of the present invention is shown generally at 1000 in FIGS. 8-17. The power operated dermatome 1000 extends between a forward or distal end 1001 and a rearward or proximal end 1002. The power operated dermatome 1000 includes an elongated handle assembly 1110 and a detachable head assembly 1200 extending from a forward or distal end 1160 of the handle assembly 1110. The handle assembly 1100 extends along a longitudinal axis 1720. An attachment assembly 1120, which is part of the handle assembly 1110, releasably affixes the head assembly 1200 to the handle assembly 1110. The decoupling of the head assembly 1200 from the handle assembly 1110 is necessary so that the rotary knife blade 1300 can be changed after an excision procedure and so that the head assembly 1200 and the handle assembly 1110 may be separately and properly sterilized between excision procedures. Additionally and advantageously, the detachability of the head assembly 1200 from the handle assembly 1110 permits the use of different head assemblies with a given handle assembly 1110. For example, a single handle assembly 1110 could be used in connection with two or more head assemblies, wherein each head assembly has a rotary knife blade with a different rotary knife blade diameter and/or blade configuration, e.g., a two inch diameter blade, a four inch diameter blade and a six inch diameter blade. The operator will select the appropriate head assembly to attach to the handle assembly 1110 depending on a particular excision or tissue cutting procedure to be undertaken and the particular blade diameter/blade configuration requirements of that procedure. This provides flexibility to the operator when performing differing excision procedures utilizing a single handle assembly 1110 and a selection of multiple differing size/differing configuration head assemblies.

As is best seen in FIGS. 8-12 and 17, the head assembly 1200 includes a frame body or frame housing 1202, a rotary knife blade 1300, a blade housing assembly 1400 including an annular blade housing 1410 and a blade lock ring 1450, and a continuous, annular rolling bearing structure 1370 which is interposed between the annular rotary knife blade 1300 and the annular blade housing 1410 to rotatably supports the rotary knife blade 1300 for rotation about a central axis of rotation 1700. The head assembly 1200 further includes a depth gauge assembly 1600, which allows an operator of the power operated dermatome 1000 to quickly and accurately set a depth of cut of skin tissue or the like to be excised/cut/trimmed by the dermatome 1000.

The rotary knife blade 1300 includes an upper body section or portion 1300 and a lower blade section or portion 1304. The body portion 1302 includes a driven gear 1330 at an upper end 1367 of the blade 1300 that is operatively engaged by a drive mechanism or drive assembly 1500 to rotate the blade 1300 about its central axis of rotation 1700. The body portion 1304 of the rotary knife blade 1300 further includes a bearing race 1320 extending radially inwardly into an outer wall 1312 of the body portion 1302. In one exemplary embodiment, the concave bearing race 1320 of the bearing race 1320 defines a frustoconical bearing surface 1322 that includes frustoconical upper bearing surface or face 1322a and a frustoconical lower bearing surface or face 1322b, the frustoconical bearing faces 1322a, 1322b converging proceeding one toward the other. In one exemplary embodiment, the annular continuous rolling bearing structure 1370 comprises an annular continuous rolling bearing strip 1372 which is received in the concave bearing race 1320 and the frustoconical upper and lower bearing faces 1322a, 1322b provide bearing regions for a plurality of ball bearings 1376 of the continuous rolling bearing strip 1372. Advantageously, as explained below a permanent, fused, mechanical connection 1390 is formed between opposite end portions 1378a, 1378b of a flexible elongated separator cage 1378 of the rolling bearing strip 1372 after placement of the separator cage 1372 in the concave bearing race 1320 such that the rolling bearing strip 1378 attains a continuous, annular shape or configuration and so that the rolling bearing strip 1372 is permanently and rotatably affixed to the outer wall 1312 of the body portion 1302 of the rotary knife blade 1300. In essence, the rolling bearing strip 1378 may be viewed as a part of the rotary knife blade 1300 for purposes of further assembly of the blade 1300 to the blade housing 1410. The blade section 1304 of the rotary knife blade 1300 includes a cutting edge 1360 at a lower end 1352 of the blade section 1304. As the blade 1300 is annular, the cutting edge 1360 is circular centered about or concentric with the blade central axis of rotation 1700 defining a circular cutting opening CO of the blade 1300.

The blade housing assembly 1400 includes the annular blade housing 1410 and a blade lock ring or lock ring 1450. The rotary knife blade 1300 (which includes the rolling bearing strip 1372) is supported for rotation about a central axis of rotation 1700 by the annular blade housing 1410. The plurality of ball bearings 1376 of the rolling bearing strip 1372 bearing against a frustoconical bearing race or bearing surface 1470 formed by an upper frustoconical bearing surface or face 1417 of the blade housing 1410 and a lower frustoconical bearing surface or face 1457 of the lock ring 1450 to thereby support the rotary knife blade 1300 for rotation about its central axis of rotation 1700. The frustoconical bearing surfaces 1417, 1322b converge proceeding one toward the other. The frame body 1202, in one exemplary embodiment is welded to and extends from the blade housing 1410 in a direction of the handle assembly 1100. A forward or distal portion 1116 of the handle assembly 1110 includes the attachment assembly 1120 for releasably securing the head assembly 1200 to the handle assembly 1110.

The depth gauge assembly 1600 of the head assembly 1200 extends from and is supported by a rearward interface or mounting portion 1420 of the blade housing 1410. The depth gauge assembly 1600 is generally similar in structure and function to the depth gauge assembly 600, as described with respect to the head assembly 200 of the first exemplary embodiment and includes an axially adjustable depth gauge plate 1622. An axial position of a bottom surface 1624 of the depth gauge plate 1622 with respect to an axial position of the blade cutting edge 1360 determines a depth of cut 1706 of the dermatome 1000, that is, a thickness of excised material, for example, an excised layer of skin tissue.

Handle Assembly 1110

The elongated handle assembly 1110 extends between a forward or distal end 1160 and a rearward or proximal end 1162 and includes an elongated handle 1112 and a proximal or rear handle cover 1170. The handle assembly 1110 establishes and extends along a longitudinal axis 1220. The longitudinal axis 1220 of the handle assembly 1110 is angled with respect to a cutting plane 1702 defined by a cutting edge 1360 of the rotary knife blade 1300 and intersects the central horizontal axis P. The cover 1170 at the proximal end 1162 of the handle assembly 1110 includes a twist and lock or quick connect type air hose coupling 1172. The coupling 1172 receives a mating coupling (not shown) of an air hose (not shown) which provides a supply of pressurized air and thereby provides motive power to the drive assembly 1500.

The handle assembly 1110 establishes and extends along the longitudinal axis 1720. The longitudinal axis 1720 intersects the head assembly central horizontal axis 1740 and angles upwardly with respect to the central horizontal axis 1740 at the acute handle angle 1725. That is, a proximal end 1162 of the handle assembly 1110 is spaced higher in an upward direction UP above the central horizontal axis 1740 of the head assembly 1200 than is the distal end 1160 of the handle assembly 1110. In one exemplary embodiment of the dermatome 1000, the handle angle 1725 with respect to the central horizontal axis 1740 is in a range of 10°-20° and, more particularly, in one exemplary embodiment, the handle angle 1725 may be approximately 15°. The handle angle 1725 advantageously provides for ease of operation and clearance for the fingers of the operator.

An outer surface 1113 of the handle 1112 is contoured for easy gripping by the operator. The handle 1112 includes the generally cylindrical, longitudinal throughbore 1114 which supports the drive motor assembly 1501 of the drive assembly 1500, including the bearing assembly 1509. In one exemplary embodiment, the drive motor assembly 1501 is actuated by a combination of an actuation lever 1150 which is pivotally mounted with respect to the handle 1112 and a two position slide switch 1151 slideably mounted on the actuation lever 1150. When the slide switch 1151 is moved to the "on" position and actuation lever 1150 is pivoted to an "on" position, generally parallel to an outer surface 1113 of the handle 1112, an actuation switch 1152 is located on the cover 1170 at the proximal end 1162 of the handle assembly 1110 is triggered. When the slide switch 1151 is in the "on" position, the actuation lever 1150 is pivoted to the "on" position and the actuation switch 1152 is triggered by pivoting movement of the lever 1150, the drive assembly 1500 is actuated to rotate the rotary knife blade 1300 about its central axis of rotation 1700. The rear handle cover 1170 of the handle assembly 1110 overlies a proximal end of the handle 1112 and is coupled to an air line or air hose (not shown) which provides a source of high pressure air to provide motive power to the drive motor assembly 1501.

The attachment assembly 1120 includes a coupling collar 1122. In one exemplary embodiment, the forward end 1160 of the handle assembly 1116 includes a coupling connector 1122 of the attachment assembly 1120. The coupling connector 1122, which is rotatable with respect to the handle 1112 about the handle assembly longitudinal axis 1720, includes interior threads 1126 which engage and thread onto a threaded outer surface 1230 of the frame body 1202 to releasably secure the head assembly 1200 to the handle assembly 1110. Advantageously, the attachment assembly 1120 allows for easy coupling and decoupling of the head assembly 1200 from the handle assembly 1110 to facilitate disassembly and sterilization or replacement of the head assembly 1200 upon completion of a skin grafting or other medical procedure performed with the dermatome 1000. In one exemplary embodiment, in use of the dermatome 1000, the rotary knife blade 1300 is replaced after each medical procedure and the head assembly 1200 and the handle assembly 1110 are disassembled from each other prior to sterilization of the decoupled assemblies 1200, 1110. Thus, it is necessary and advantageous to have a quick and easy attachment assembly 1120 for coupling and decoupling the assemblies 1200, 1110.

Drive Assembly 1500

The rotary knife blade 1300 is rotated with respect to the blade housing assembly 1400 about the central axis of rotation R by a drive assembly 1500 which includes a drive motor assembly 1501 and a gear train or drive train 1520. In one exemplary embodiment of the drive assembly 1500, the drive motor assembly 1501 includes a vane-type air or pneumatic drive motor 1502, while the drive train 1520 includes a pinion gear 1522. In one exemplary embodiment, the drive motor assembly 1501 is supported by the handle assembly 1110, while the drive train 1520 extends through a throughbore 1209 of the frame body 1202 to interface with and rotatably drive a driven gear 1330 of the rotary knife blade 1300.

In one exemplary embodiment, the drive motor assembly 1501 includes the pneumatic motor 1502 disposed within the longitudinal throughbore 1114 of the handle 1112. High pressure air is communicated via an air hose to drive the motor 1502. Specifically, high pressure air is routed through the air hose through a quick connect fitting or coupling (not shown) at the end of the air hose. The air hose quick connect fitting engages a mating quick connect fitting coupling or fitting 1172 extending from a cover 1170 of the handle assembly 1110 at the proximal end 1162 of the handle assembly 1110. Thereby, high pressure air is communicated to the motor 1502 wherein the air is routed through a body of the motor 1502 and directed against a plurality of vanes to rotate a rotor of the motor 1502. The motor 1502 includes an output shaft and coupling 1503 which is operatively coupled to an input shaft 1524 of the pinion gear 1522. The output shaft and coupling 1503 are supported for rotation by a bearing assembly 1509 disposed within a longitudinally extending throughbore 1114 of a cylindrical handle 1112 of the handle assembly 1110.

When driven by the motor drive coupling 1503, the pinion gear 1522 rotates about a pinion gear axis of rotation 1750 which, in one exemplary embodiment, is coincident with the handle assembly longitudinal axis 1720. A gear head 1526 of the pinion gear 1522 engages and drives a driven gear 1330 of the rotary knife blade 1300 to rotate the blade 1300 about its central axis of rotation 1700. As the handle assembly 1110 is angled or canted with respect to a horizontal extent of the head assembly and, specifically, the horizontal extent of a In one exemplary embodiment, the pinion gear 1522 extends in the forward direction FW beyond a front or forward end 1160 of the handle assembly 1110. When the handle assembly 1110 is assembled to the frame body 1202 of the head assembly 1200, the pinion gear 1522 extends through a central throughbore 1209 of the frame body 1202 and engages the driven gear 1330 of the rotary knife blade 1300 to drive the blade 1300 about its central axis of rotation 1700. Advantageously, an outer surface 1525 of the input shaft 1524 of the pinion gear 1522 includes an annular groove 1530. The annular groove 1530 provides for clearance with respect to an upper end 1454 of the lock ring 1450 in the event that an operator were to attempt to unthread and remove the lock ring 1450 from the blade housing 1410, with the handle assembly 1110 still affixed to the head assembly frame body 1202. In one exemplary embodiment, the pinion gear 1526 is a bevel gear 1528 designed accommodate handle angle 1725 which results in a non-orthogonal line of action between driven gear 1330 which rotates about the blade central axis of rotation 1700 and an axis of rotation 1750 of the pinion gear 1522.

The upper end 1454 of the lock ring 1450 advantageously includes an axially recessed region 1454a that provides for clearance for insertion and removal of the pinion gear 1522 and, specifically, provides clearance such that the gear head 1526 of the pinion gear 1522 does not hit against the upper end 1454 of the lock ring 1450 when head assembly 1200 is removed or uncoupled from the handle assembly 1110 by decoupling the attachment assembly 1120 from a threaded outer surface 1230 of a rearward handle attachment portion 1204 of the frame body 1202. It is recommended that the operator first decouple the head assembly 1200 from the handle assembly 1110 prior to removal of the lock ring 1450 for purposes of changing the rotary knife blade 1300 after an excision procedure. However, as a failsafe provision, if the operator proceeds to remove the lock ring 1450 from the blade housing 1410 by rotating the lock ring 1450 to decouple the threaded engagement of a threaded portion 1458 of the lock ring 1450 from the corresponding threaded portion 1418 of the blade housing 1410 with the head assembly 1200 still assembled to the handle assembly 1110, the annular groove 1530 in the outer surface 1525 of the input shaft 1524 of the pinion gear 1522 is configured and positioned to prevent interference between the upper end 1454 of the lock ring 1450 and the input shaft 1524 even if the lock ring 1450 is rotated through a full turn such that the lock ring 1450 is completely unthreaded from the blade housing threaded portion 1418. Stated another way, if the head assembly 1200 is affixed to the handle assembly 1110 and the lock ring 1450 is rotated to a position where the recessed region 1454a of the upper surface 1454 of the lock ring 1450 is no longer aligned with or overlaps a region of the pinion gear input shaft 1524, the annular groove 1530 in the outer surface 1525 of the pinion gear input shaft 1524 prevents undesired contact between the lock ring 1450 and the input shaft 1524 of the pinion gear 1522. In one exemplary embodiment, a depth of the annular groove 1530 is approximately 0.020 in.

Head Assembly 1200

Figure 12:
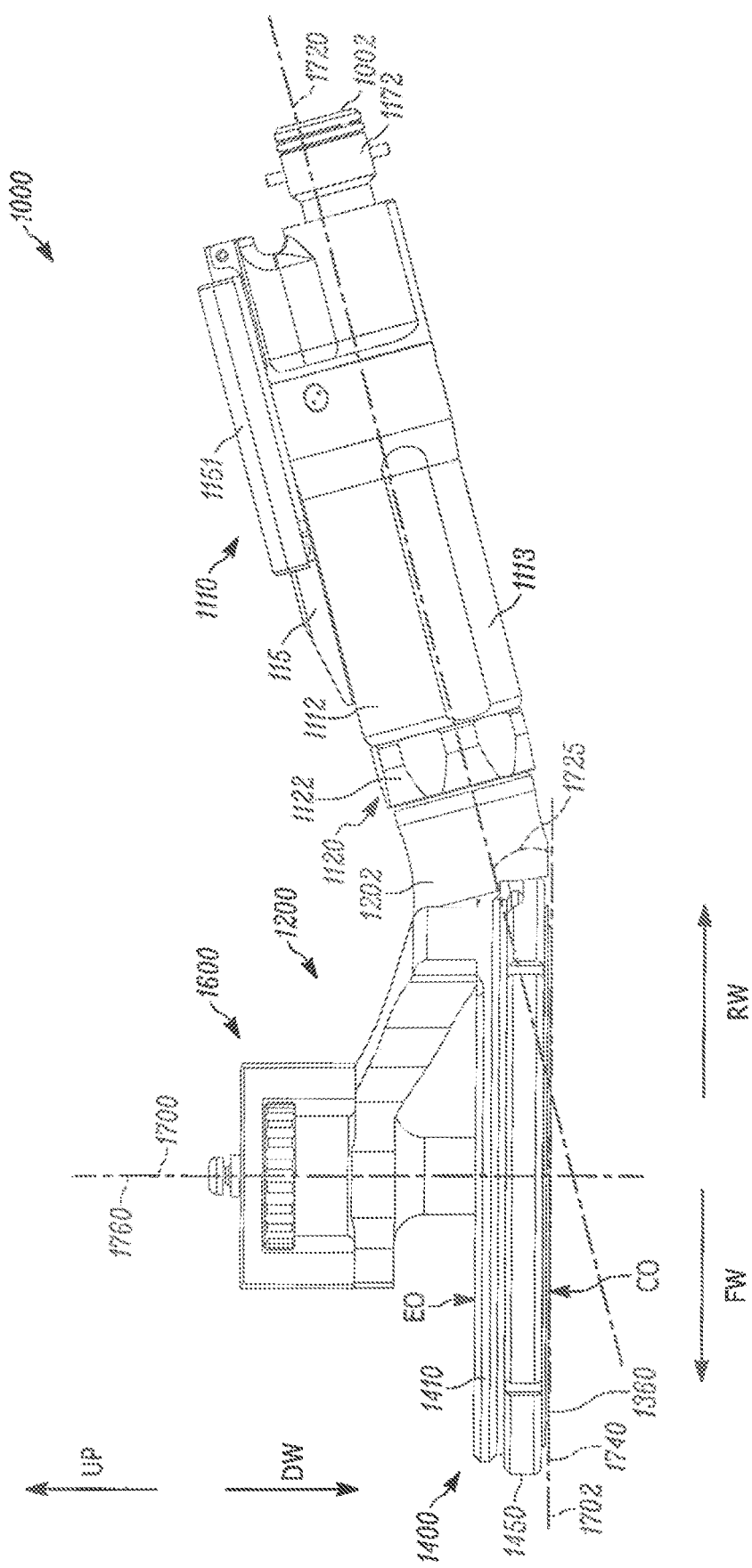
FIG. 12 is a schematic side elevation view of the power operated dermatome of FIG. 8.

The head assembly 1200 includes the rotary knife blade 1300, the blade housing assembly 1400 and the depth gauge assembly 1600. The head assembly 1200 is generally similar in structure and function to the head assembly 200 of the first exemplary embodiment of the power operated dermatome 100, as described above, and such description of the head assembly 200, including the corresponding drawing Figures is incorporated herein by reference. The rotary knife blade 1300 includes an upper end 1367 and an axially spaced apart lower end 1368 and a body section or portion 1302 adjacent the upper end 1367 and a blade section or portion 1304 extending from a lower end 1308 of the body portion 1302. A lower end 1352 of the blade section 1304 includes a cutting edge 1360 of the blade 1300 which establishes the lower end 1368 of the blade 1300. The circular cutting edge 1360 of the blade 1300 defines the cutting plane 1702 of the blade 1300. The circular cutting edge 1360 of the blade 1300 is concentric with or centered about the blade central axis of rotation 1700 and the blade cutting plane 1702 is orthogonal to the central axis of rotation 1700. A head assembly central horizontal axis 1740 extends horizontally along or coincident with the blade cutting plane 1702 and intersects the blade central axis of rotation 1700. As can be seen in the top plan and bottom plan views of FIGS. 13 and 14, the head assembly central horizontal axis 1740 is in axial alignment with the handle assembly longitudinal axis 1720, hence, it is referred to as the central horizontal axis 1740 since it represents a direction through the cutting plane 1702 (and the cutting edge 1360) of the rotary knife blade 1300 that is in axial alignment with the handle assembly longitudinal axis 1720 and which intersects the handle assembly longitudinal axis 1720. As can be seen from the side elevation and section views of FIGS. 12 and 17, the handle assembly longitudinal axis 1720 is canted or angled upwardly with respect to the head assembly central horizontal axis 1740 at an acute handle assembly angle 1725 (FIG. 12). The head assembly central horizontal axis 1740 establishes a forward direction FW for the power operated dermatome 1000, that is, a direction that is along or parallel to the head assembly central horizontal axis 1740 in a direction from the proximal end 1002 to the distal end 1001 of the dermatome 1000 and a rearward direction RW for the power operated dermatome 1000, that is a direction that is along or parallel to the head assembly central horizontal axis 1740 in a direction from the distal end 1001 to the proximal end 1002 of the dermatome 1000. An upward direction UP and a downward direction DW are directions as shown in, for example FIG. 12, that are along or parallel to the blade central axis of rotation 1700.

Frame Body 1202

Figure 10:
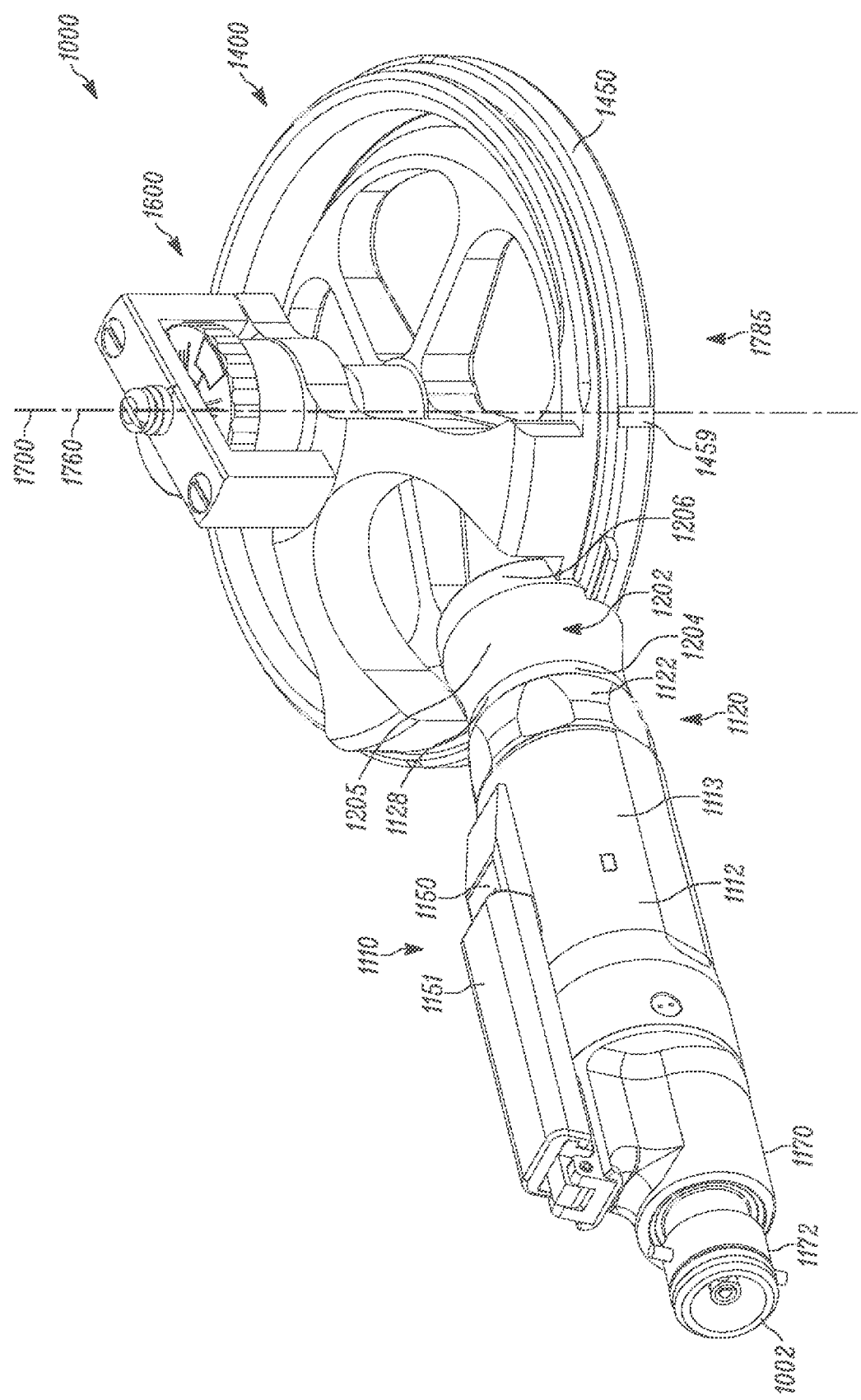
FIG. 10 is a schematic rear perspective view of the power operated dermatome of FIG. 8.
Figure 11:
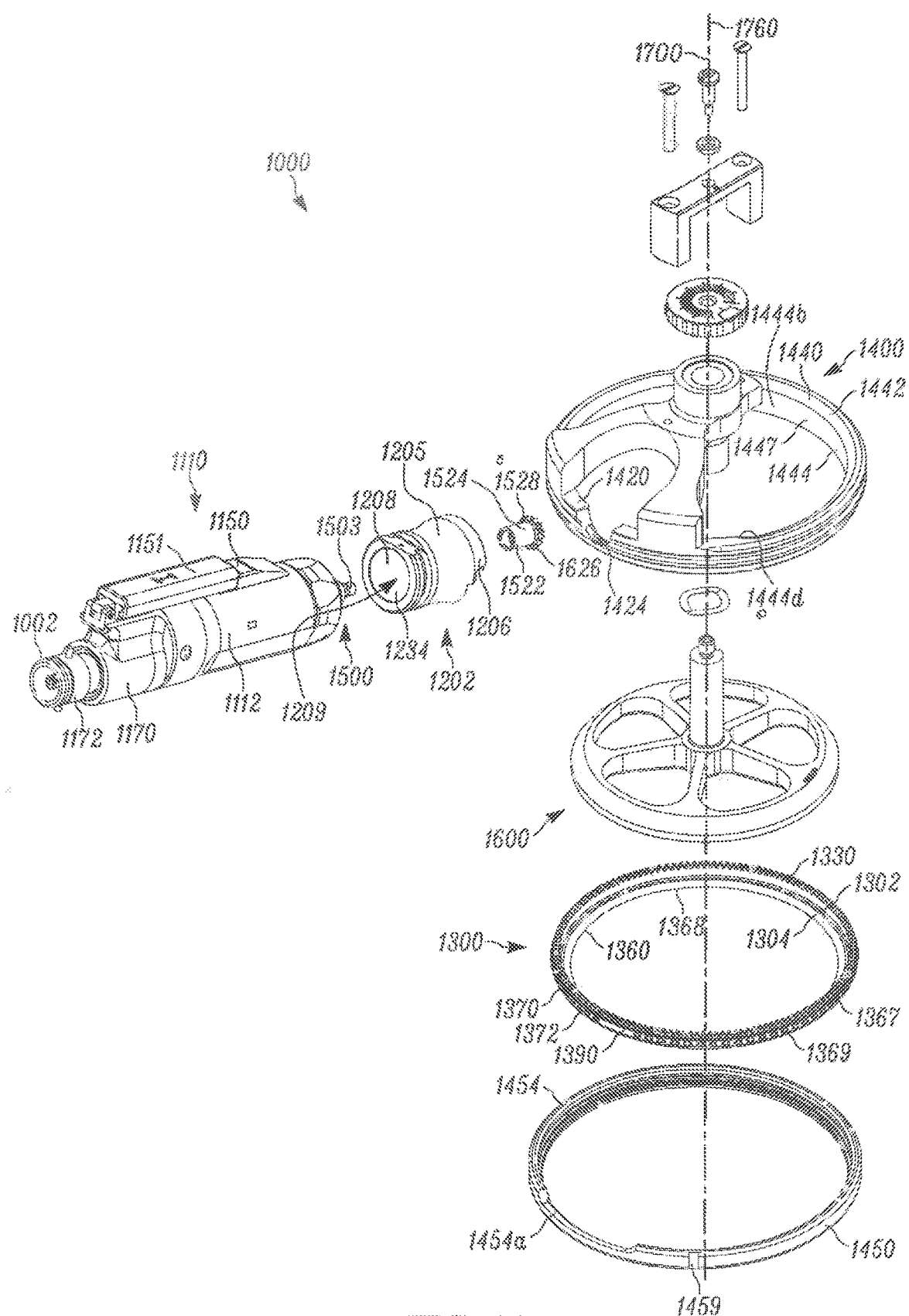
FIG. 11 is a schematic rear exploded view of the power operated dermatome of FIG. 8.

As best seen in FIGS. 10 and 11, the frame body 1202 comprises a generally cylindrical body 1205 that includes a rearward handle attachment portion 1204 and a forward interface portion 1206. The rearward handle attachment portion 1204 includes the threaded outer surface 1230 of the frame body 1202. The threaded outer surface 1230 of the rearward handle attachment portion 1204 is engaged by the coupling collar 1122 of the attachment assembly 1120 to releasably affix the head assembly 1200 to the handle assembly 1110. The forward interface portion 1206 is configured to be received by and engage the rearward interface or mounting portion 1420 of the blade housing 1410. In one exemplary embodiment, the forward interface portion 1206 of the frame body 1202 is welded to the rearward interface portion 1420 of the blade housing to permanently affix the frame body 1202 to the blade housing 1410. It should be appreciated, however, that the interface portion 1206 of the frame body 1202 could be affixed to the interface portion 1420 of the blade housing 1410 by means other than welding, as known to those of skill in the art. Additionally, the instead of separate components, the frame body 1202 and the blade housing 1410 could be fabricated as a single component, for example by casting, as would be appreciated by those of skill in the art.

The frame body 1202 includes a central throughbore 1209 (FIG. 11) extending along the handle assembly longitudinal axis 1710. The bearing assembly 1509 and the pinion gear 1522 extend into the central throughbore 1209. The gear head 1526 of the pinion gear 1522 extends through a front opening 1232 to mesh with the driven gear 1330 of the rotary knife blade 1300. A rear opening 1234 of the throughbore 1209 allows entry of the bearing assembly 1509 for proper support of the motor shaft and coupling 1503.

Blade Housing Assembly 1400

As best seen in FIGS. 17, 17A, 17B, 22-24 and 33, the blade housing assembly 1400 includes an annular blade housing 1410 and a blade lock ring or lock ring 1450 which, in one exemplary embodiment, engages the blade housing 1410 via a threaded connection 1480 to trap and secure the rotary knife blade 1300 for rotation with respect to the blade housing assembly 1400. The blade housing 1410 includes a first upper end 1412 and an axially spaced apart second lower end 1419. The blade housing 1410 further includes the inner wall 1411 and the radially spaced apart outer wall 1413. The upper end 1412 of the blade housing 1410 defines an upper exit opening EO (FIG. 17) of the dermatome 1000, that is an opening through which a layer of excised material, such as an excised tissue layer ETL, shown schematically in FIG. 33, exits a generally cylindrical interior region 1780 defined by an assembled combination 1785 of the rotary knife blade 1300, the blade housing 1410 and the lock ring 1450. The opposite or lower end of the cylindrical interior region 1780 is defined by the blade cutting opening CO. Both the cutting opening CO and the exit opening EO are centered about the blade central axis of rotation 1700 and a vertically extending blade housing center axis or vertical blade housing center line 1760 and have similar diameters, the exit opening EO having a slightly larger diameter.

As mentioned above, the blade housing 1410 is centered about the vertically extending blade housing center axis or vertical blade housing center line 1760 which is substantially coincident with the blade central axis of rotation 1700. In a forward, circumferentially extending skin deflector portion 1440 of the blade housing 1410, the annular body 1410a includes a blade receiving portion or blade receiving body 1449 and a blade shield 1444, extending radially inwardly from the blade receiving body 1449. In the forward skin deflector portion 1440 of the blade housing 1410, an inverted, generally u-shaped annular blade receiving channel 1416 of the blade housing 1410 is part of the blade receiving body 1449 and is radially spaced from the blade housing inner wall 1411 and the blade housing outer wall 1413. The blade receiving channel 1416, in the circumferentially extending skin deflector portion 1440 of the blade housing 1410, is defined by a first generally vertical inner wall 1416a and a radially spaced apart second generally vertical inner wall 1416a, which is radially closer to the vertical blade housing center line 1760. That is, the first vertical inner wall 1416a is radially closer to the blade housing outer wall 1413, while the second vertical inner wall 1416b is radially closer to the blade housing inner wall 1411. The annular blade channel 1416 also includes a generally horizontal bridging surface 1416c bridging the first and second vertical inner walls 1416a, 1416b. The first vertical wall 1416a includes a first, upper generally planar surface or portion 1416d that extends substantially parallel to the blade housing center line 1760 and defines a general extent of the first vertical wall 1416a. A second, lower offset surface or portion 1416e of the first vertical wall 1416a is radially offset from the first, upper portion 1416d, that is, the second, lower offset portion 1416e extends radially into the general extent of the first vertical wall 1416a and defines: a) a planar, frustoconical bearing surface or face 1417 that extends in a direction transverse to the blade housing center line 1760; and b) a planar, vertically extending relief surface 1417a that defines a vertex of a total bearing race 1470 defined by the blade housing 1410 and the blade lock ring 1450 and is substantially parallel to the blade housing center line 1760. The frustoconical bearing surface 1417 extends between the first, upper portion 1416d and the vertically extending relief surface 1417a extends between the frustoconical bearing surface 1417 and the outer lower end 1414 of the lower end 1419 of the blade housing 1410. Depending on the size or diameter of the plurality of ball bearings 1376 of the annular rolling bearing strip 1372, the dimensions of the second, lower offset portion 1416e of the first vertical wall 1416a, and the requirements of operating or running clearance of the assembled combination 1785 of the rotary knife blade 1300, blade housing 1410 and blade lock ring 1450, the planar, vertically extending relief surface 1417a may serve as a vertical bearing surface which has intermittent bearing contact with the plurality of ball bearings 1376 of the annular rolling bearing strip 1372. As would be recognized by one of skill in the art, running or operating clearance between the respective bearing surfaces rotary knife blade 1300, the blade housing 1410 and the blade lock ring 1450 must be provided to allow the rotary knife blade 1300 to rotate relatively freely within the confines of the assembled combination of the blade housing 1410 and the blade lock ring 1450. Actual running clearance will depend on a number of factors including the cutting or trimming application, the amount of time of use and the degree of wear of various components of the power operated rotary dermatome 1000 including the rotary knife blade 6300 and the blade housing 6800, the extent and type of lubrication provided, etc. However, running clearance typically is on the order of a 0.001-0.005 in radial clearance or gap between opposing or facing bearing surfaces of the rotary knife blade 1300 and the blade housing assembly 1400.

The blade channel 1416 receives the driven gear 1330 of the rotary knife blade 1300. The blade housing 1410 is centered about a vertically extending blade center axis or vertical blade center line 1760 which is substantially coincident with the blade central axis of rotation 1700. Viewed in three dimensions, the frustoconical bearing surface 1417 is annular and is a frustum of a right angled cone and converges in the upward direction UP, that is, in a direction proceeding toward the upper end 1412 of the blade housing 1410. In one exemplary embodiment the bearing surface 1417 is angled at approximately a 45° angle with respect to the blade housing axial center line 1760. The total bearing race 1470 defined by the blade housing assembly 1400 results from a combination of the frustoconical bearing surfaces 1417, 1457 of the blade housing 1410 and the blade lock ring 1450, which provide bearing contact surfaces for the plurality of ball bearings 1376 of the annular rolling bearing strip 1372. Additionally, as noted above, depending on the operating or running clearance between the respective bearing surfaces rotary knife blade 1300, the blade housing 1410 and the blade lock ring 1450 and the specific dimensional size and configuration of mating bearing components of the annular rotary knife blade 1300, the annular blade housing 1410 and the annular blade lock ring 1450, the planar, vertically extending relief surface 1417a of the second, lower offset portion 1416e of the first vertical wall 1416a, that is, the vertex of the v-shaped bearing surface 1470a, may also serve as a vertical bearing surface of the total bearing race 1470 having intermittent bearing contact with the plurality of ball bearings 1376 of the annular rolling bearing strip 1372. The total bearing race 1470 serves as a sideways oriented generally v-shaped bearing surface 1470a for the annular rolling bearing strip 1372 of the rotary knife blade 1300 when the blade lock ring 1450 is secured to the blade housing 1410 and the rotary knife blade 1300 is captured or sandwiched therebetween. The planar, frustoconical bearing surface 1417 of the blade housing 1410 is axially spaced from the lower surface of the outer lower end 1414 by the vertically extending relief surface 1417a that functions as the vertex of the v-shaped bearing surface 1470a of the total bearing race 1470 and, as noted above, may function as a vertical bearing surface for the assembled blade housing assembly 1400.

Figure 13:
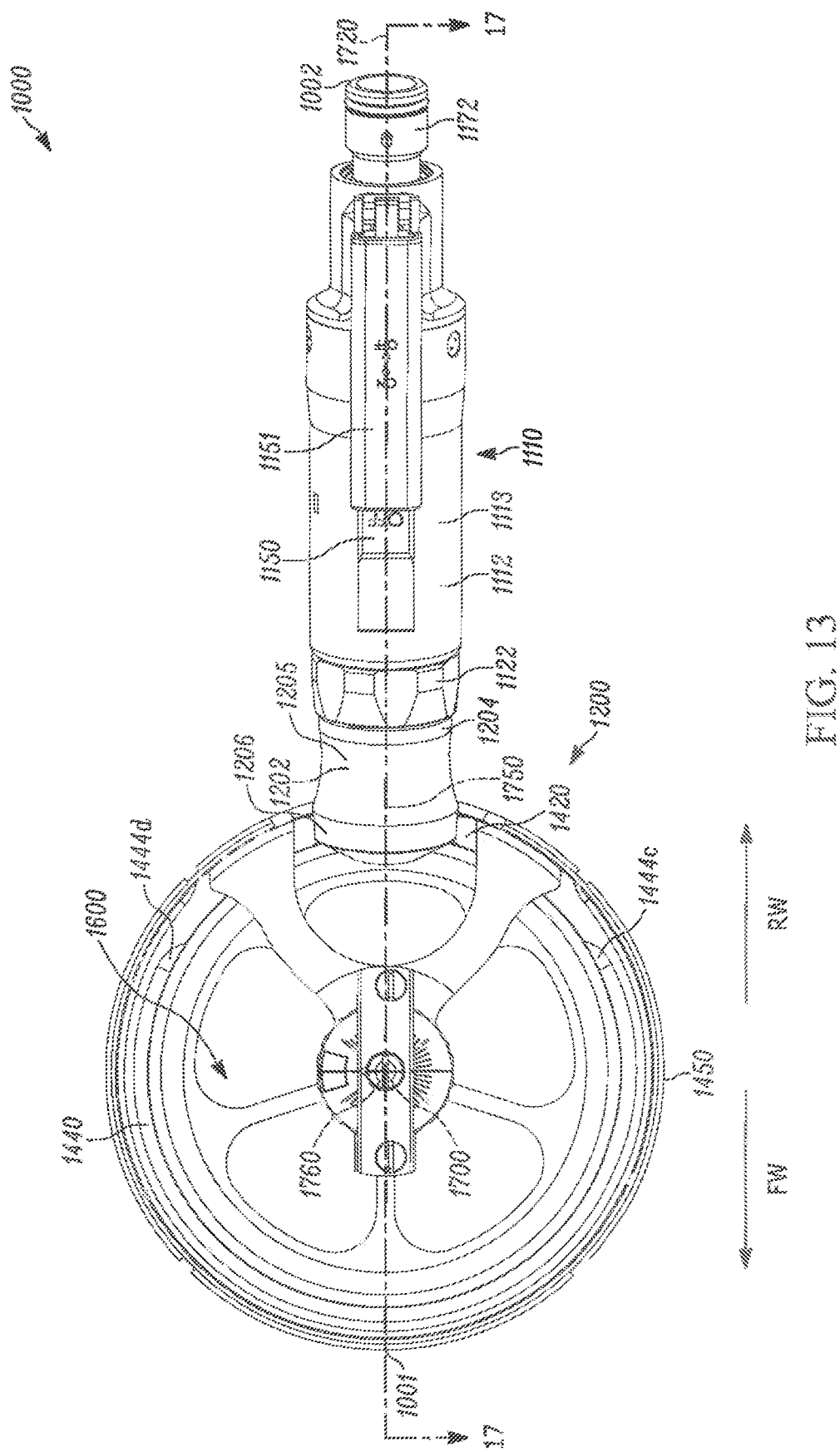
FIG. 13 is a schematic top plan view of the power operated dermatome of FIG. 8.
Figure 14:
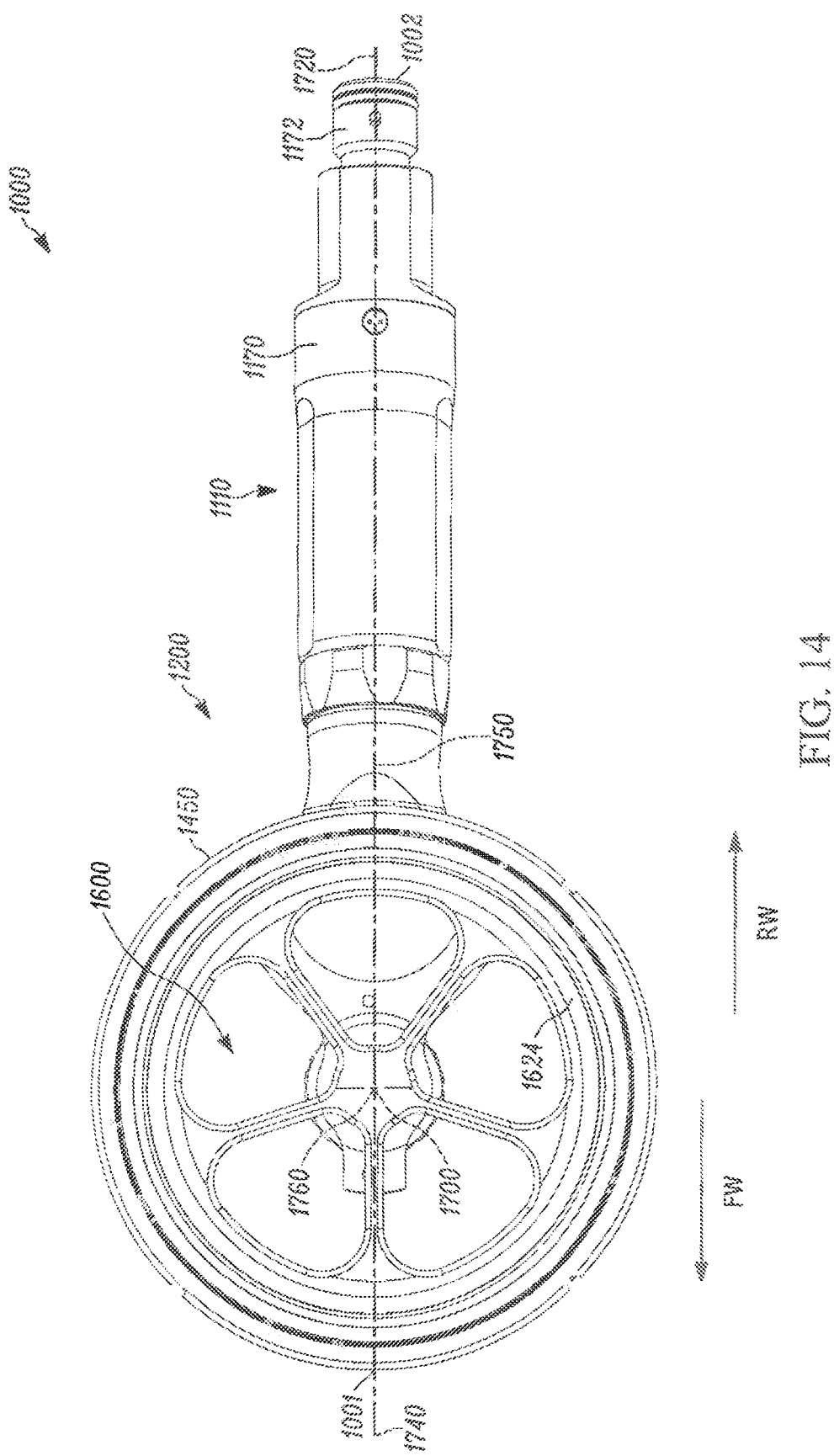
FIG. 14 is a schematic bottom plan view of the power operated dermatome of FIG. 8.
Figure 15:
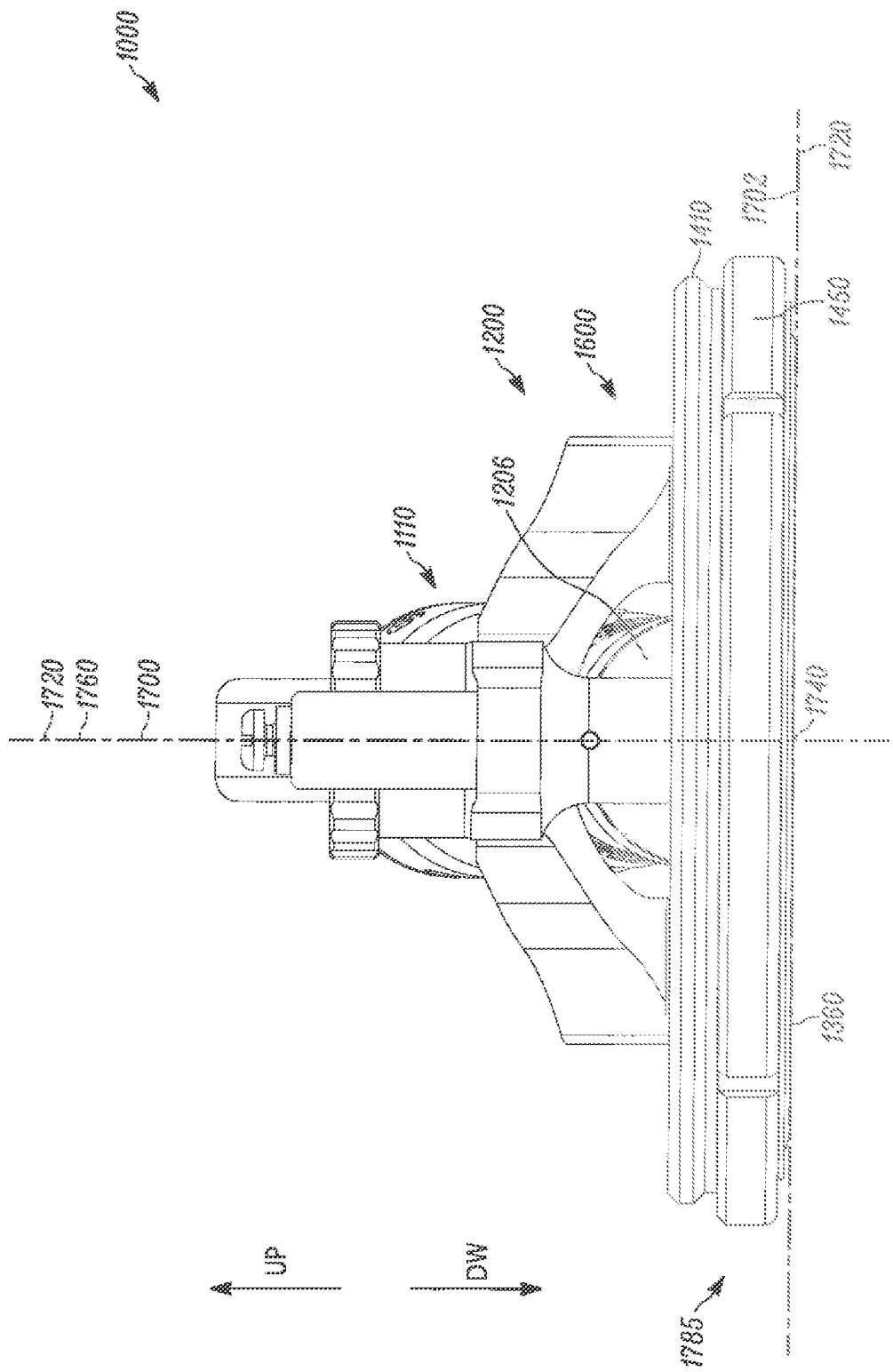
FIG. 15 is a schematic front plan view of the power operated dermatome of FIG. 8.
Figure 16:
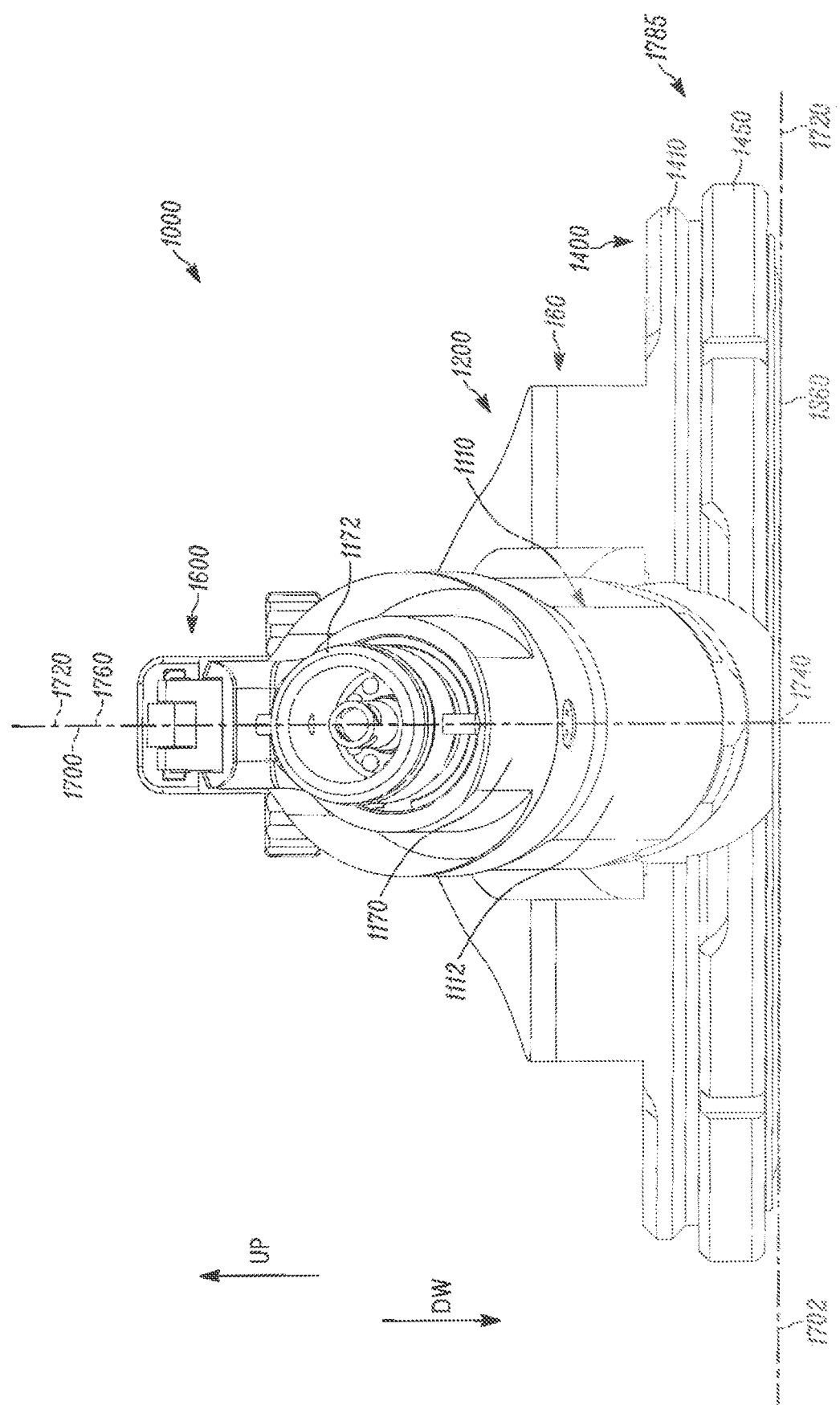
FIG. 16 is a schematic rear plan view of the power operated dermatome of FIG. 9.
Figure 17:
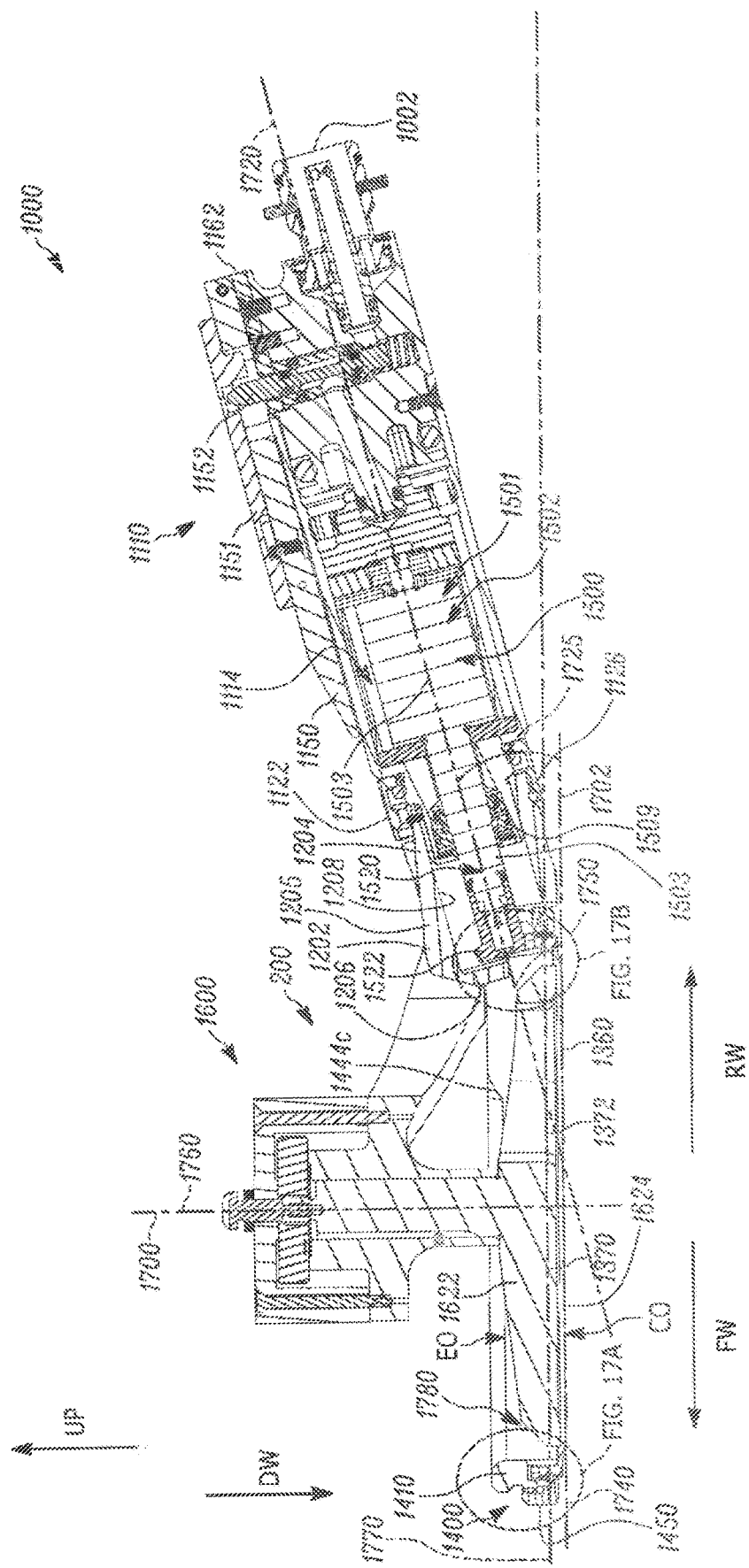
FIG. 17 is a schematic longitudinal section view of the power operated dermatome of FIG. 8 as seen from a plane indicated by the line 17-17 in FIG. 13.
Figure 17B:
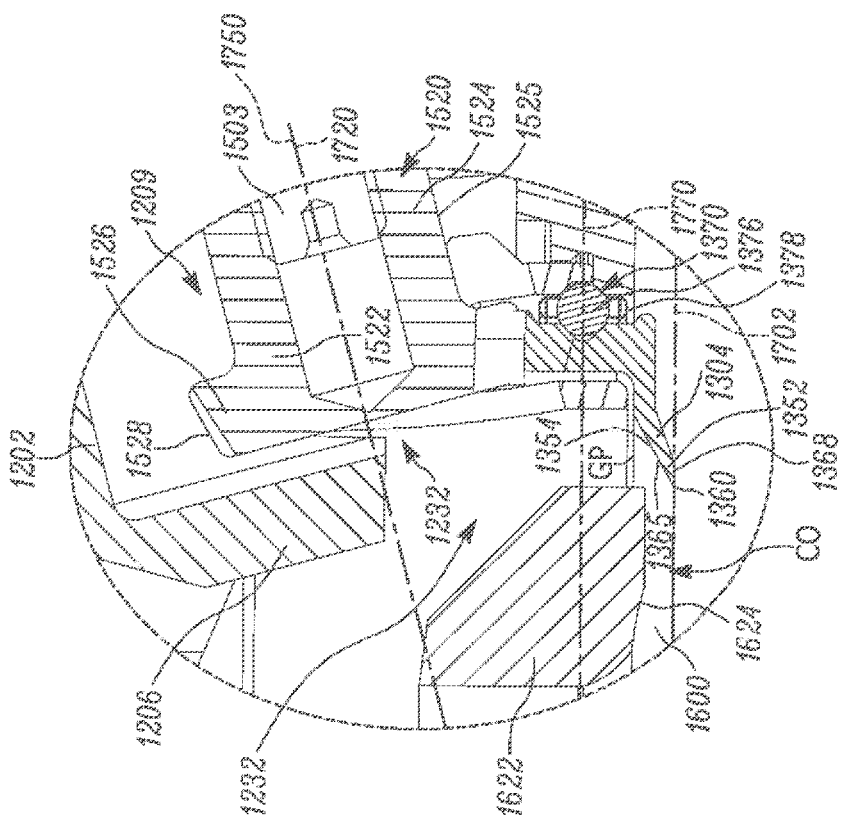
FIG. 17B is a schematic enlarged longitudinal section view of a portion of the power operated dermatome of FIG. 8 as seen within the dashed line labeled FIG. 17B in FIG. 17.
Figure 17A:
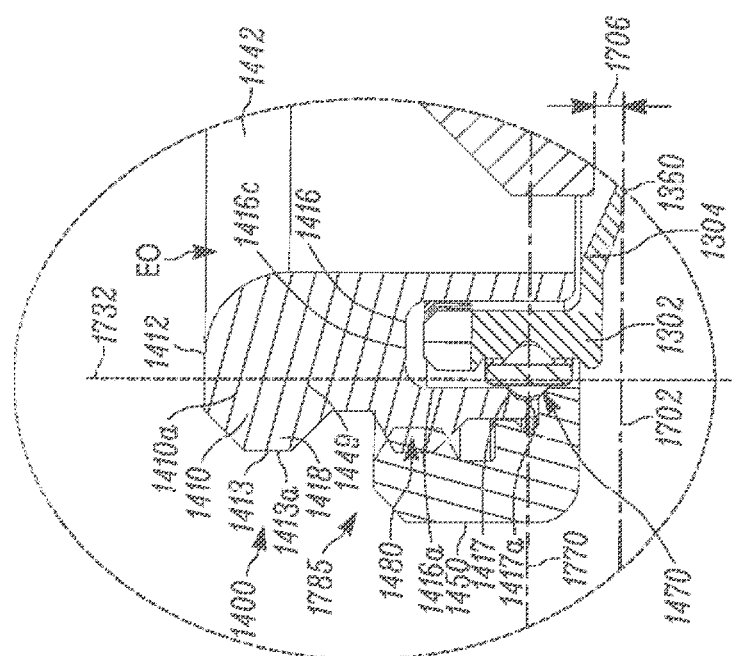
FIG. 17A is a schematic enlarged longitudinal section view of a portion of the power operated dermatome of FIG. 8 as seen within the dashed line labeled FIG. 17A in FIG. 17.
Figure 18:
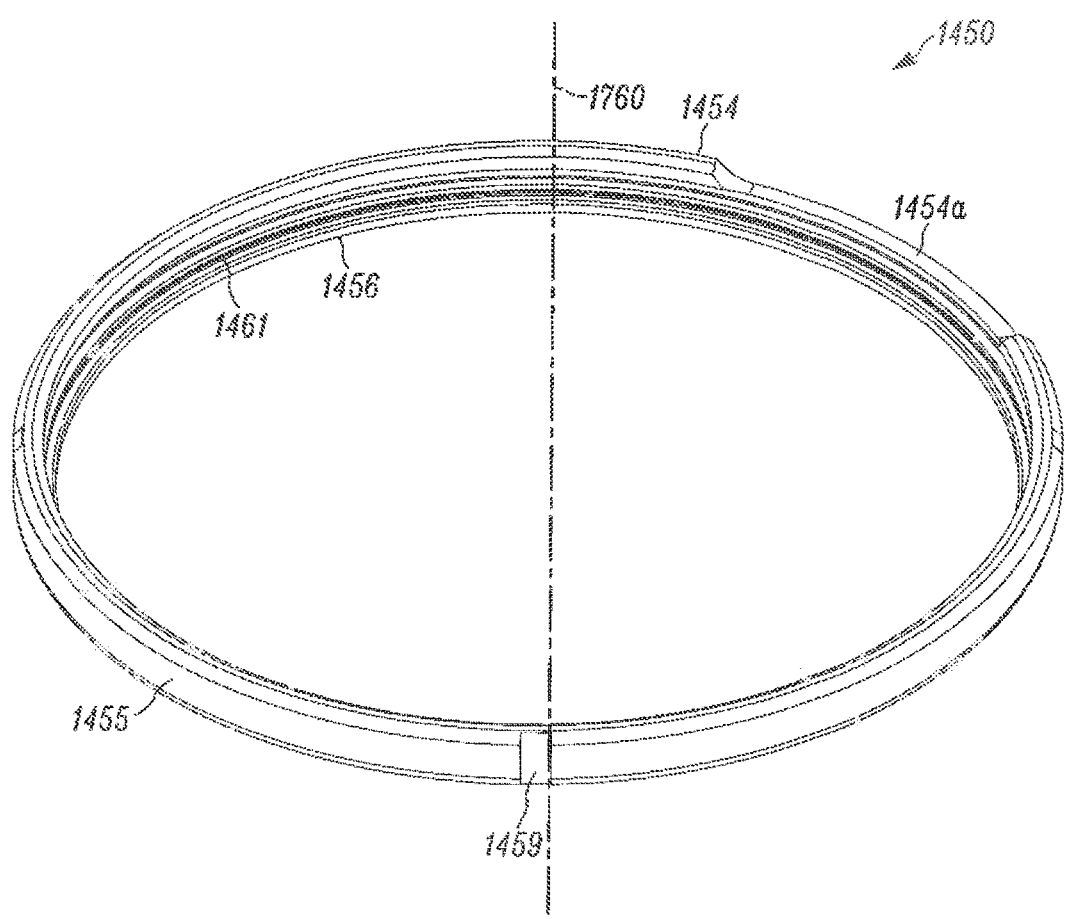
FIG. 18 is a schematic perspective view of the lock ring of the blade housing assembly of the head assembly of the power operated dermatome of FIG. 8.
Figure 19:
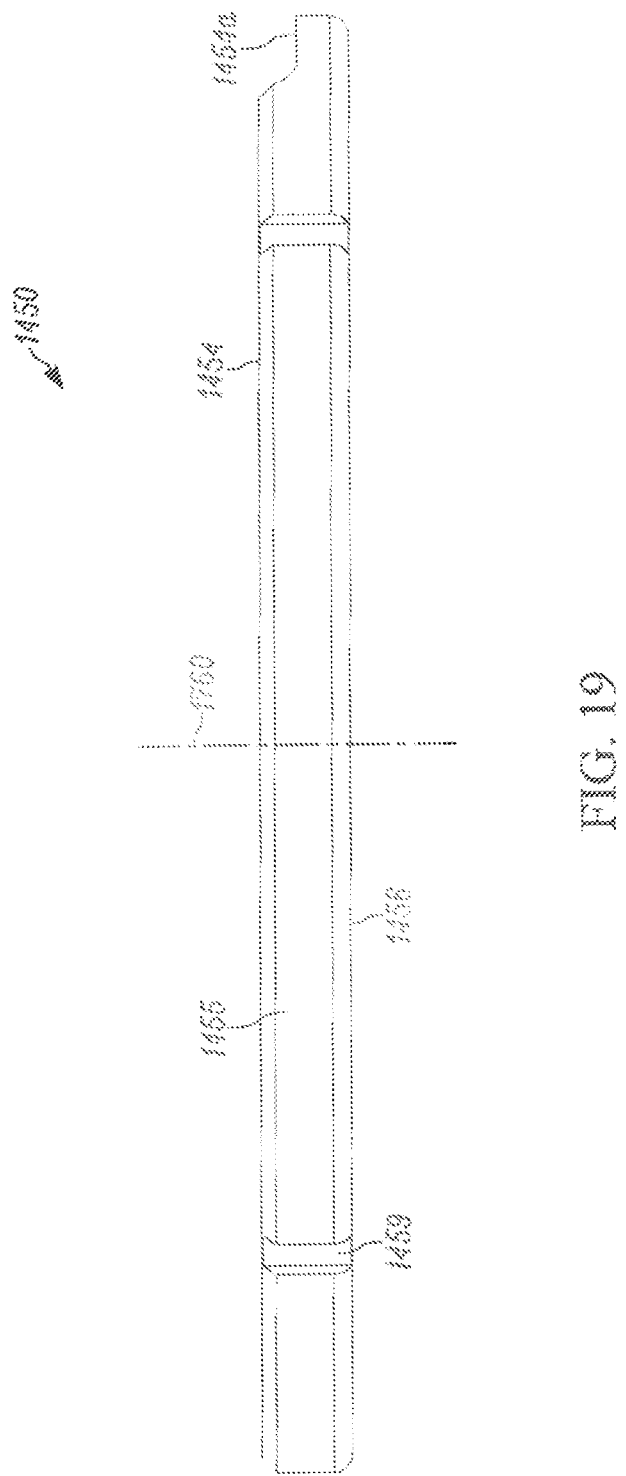
FIG. 19 is a schematic side elevation view of the lock ring of FIG. 18.
Figure 20:
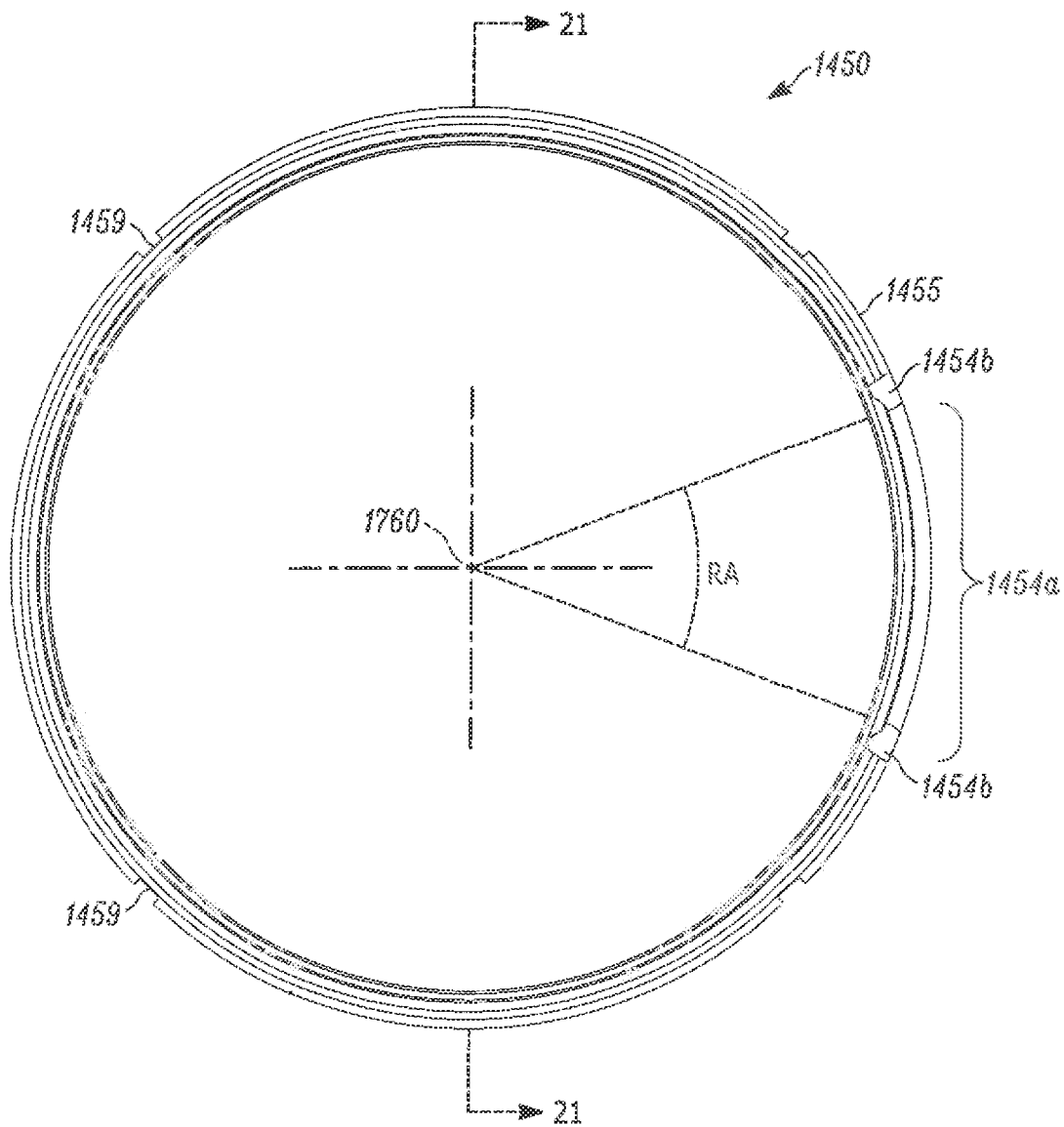
FIG. 20 is a schematic top plan view of the lock ring of FIG. 18.
Figure 21:
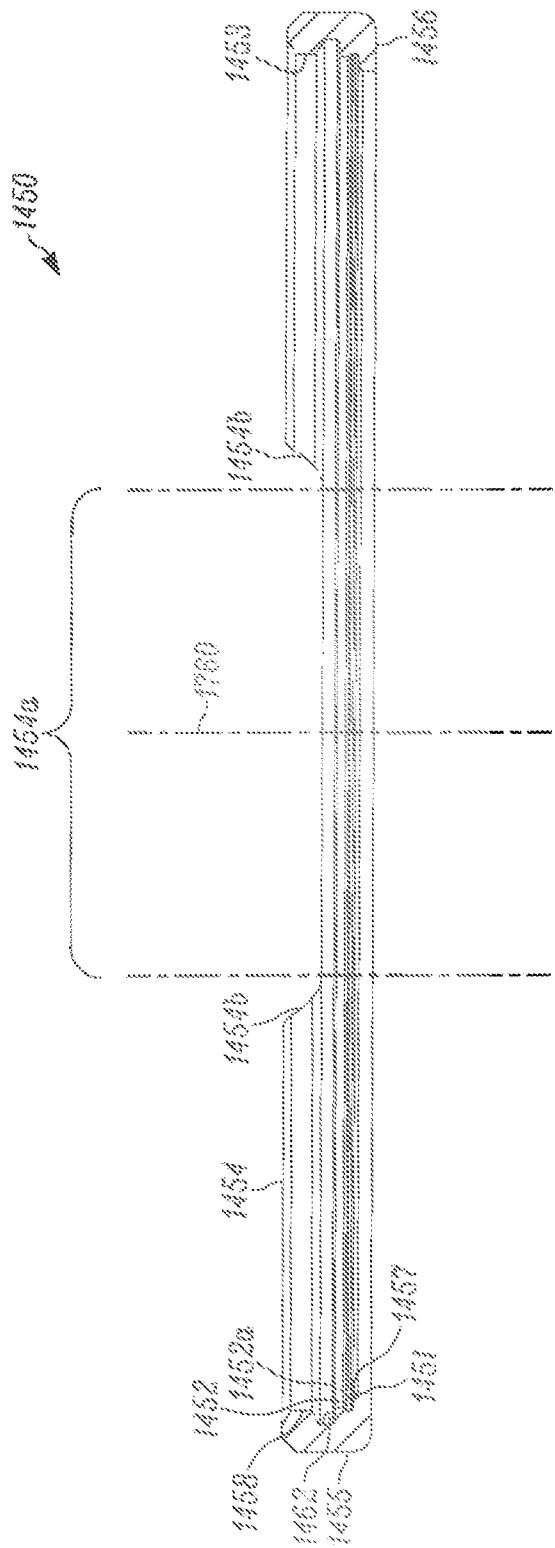
FIG. 21 is a schematic vertical section of the lock ring of FIG. 18, as seen from a plane indicated by the line 21-21 in FIG. 20.
Figure 22:
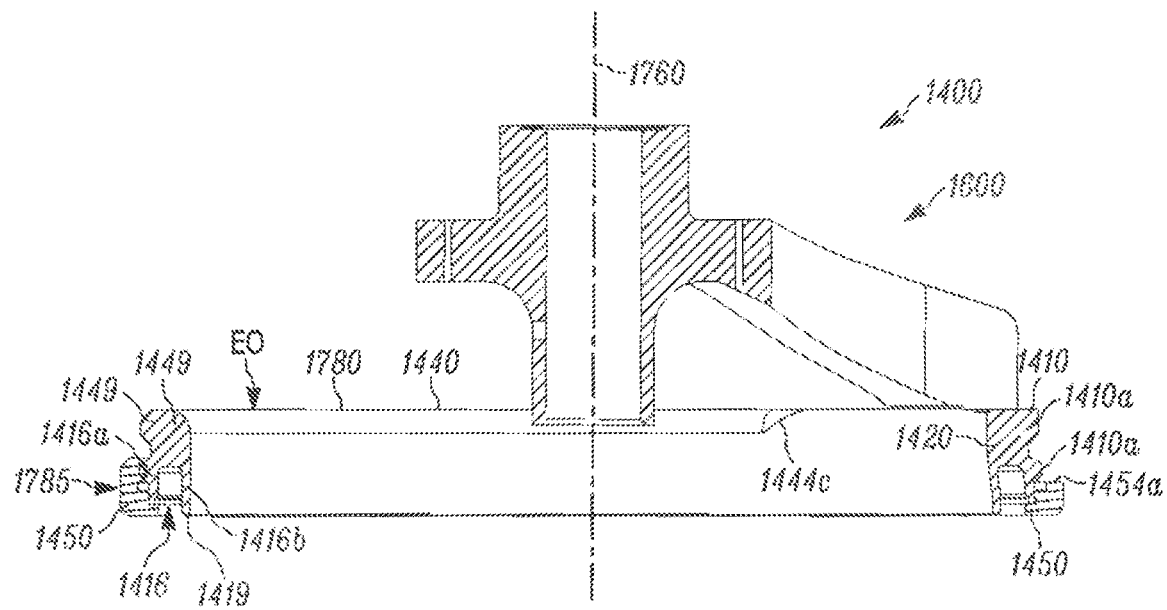
FIG. 22 is a schematic longitudinal section view of the blade housing assembly of the head assembly of the power operated dermatome of FIG. 8 including the annular blade housing and the annular lock ring in assembled condition, viewed along a longitudinal axis of the handle assembly.
Figure 23:
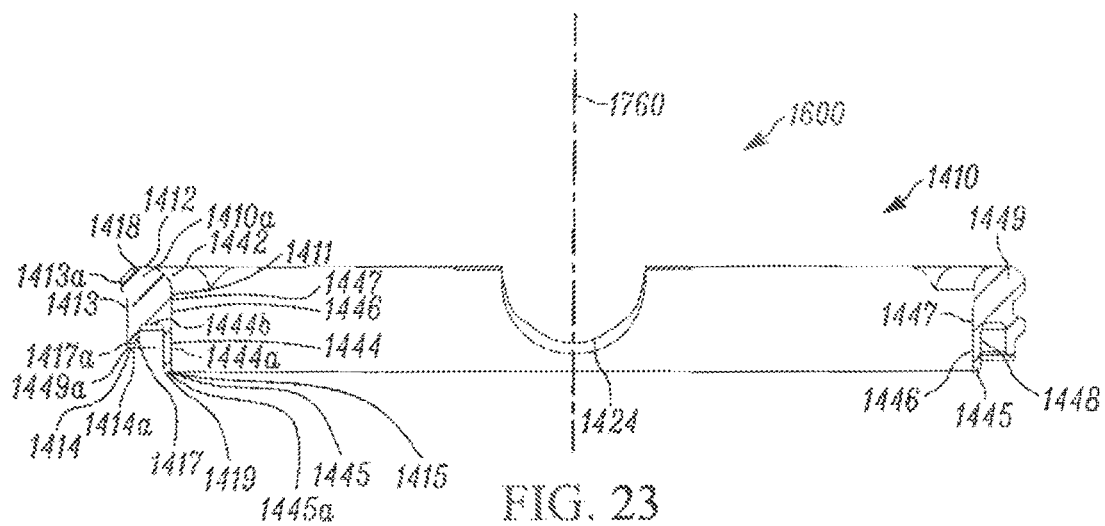
FIG. 23 is a schematic vertical section view of the blade housing of the blade housing assembly of FIG. 23, with portions removed for clarity and viewed orthogonally to the longitudinal axis of the handle assembly.
Figure 24:
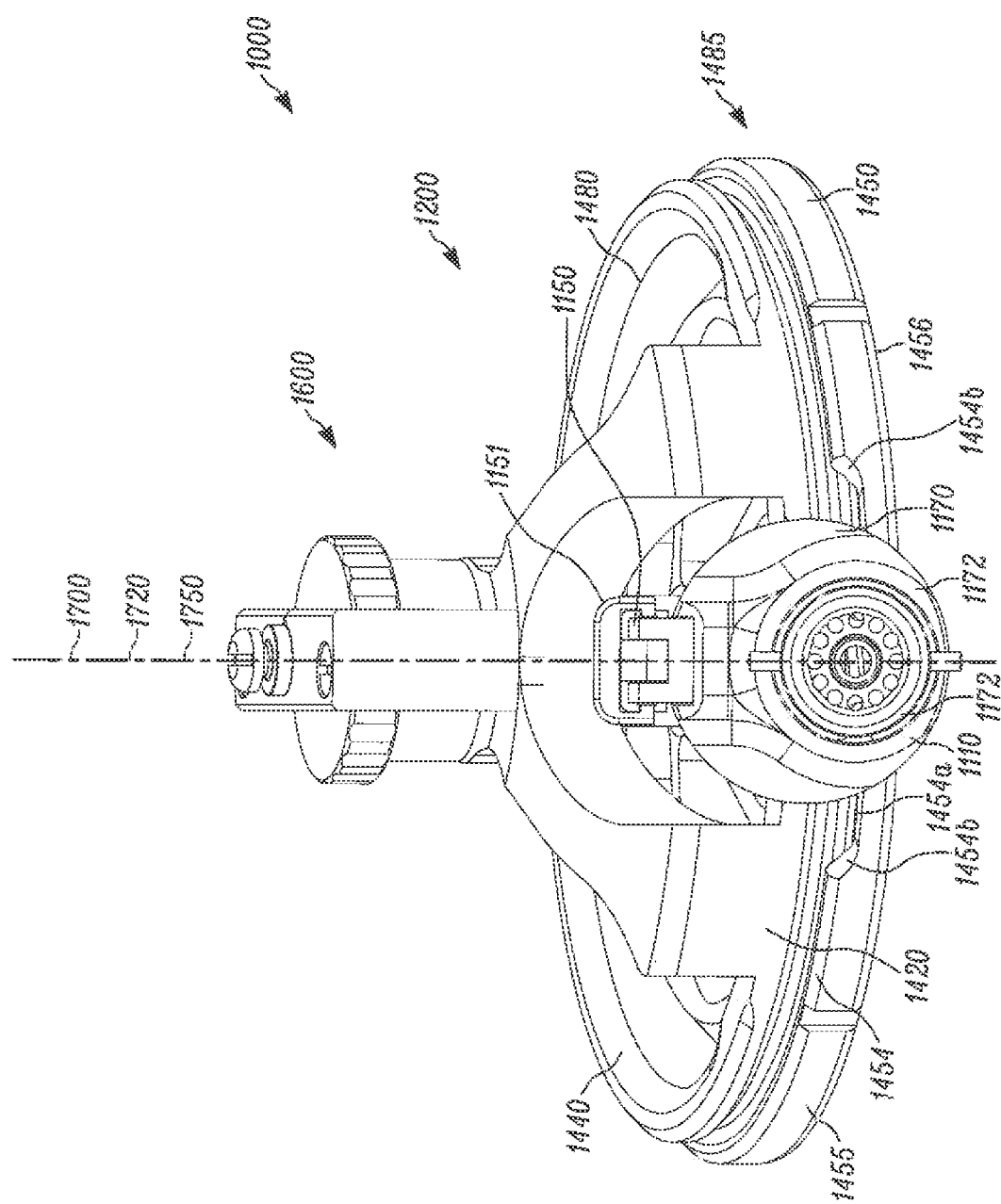
FIG. 24 is a schematic rear perspective view of the power operated dermatome of FIG. 8.
Figure 27:
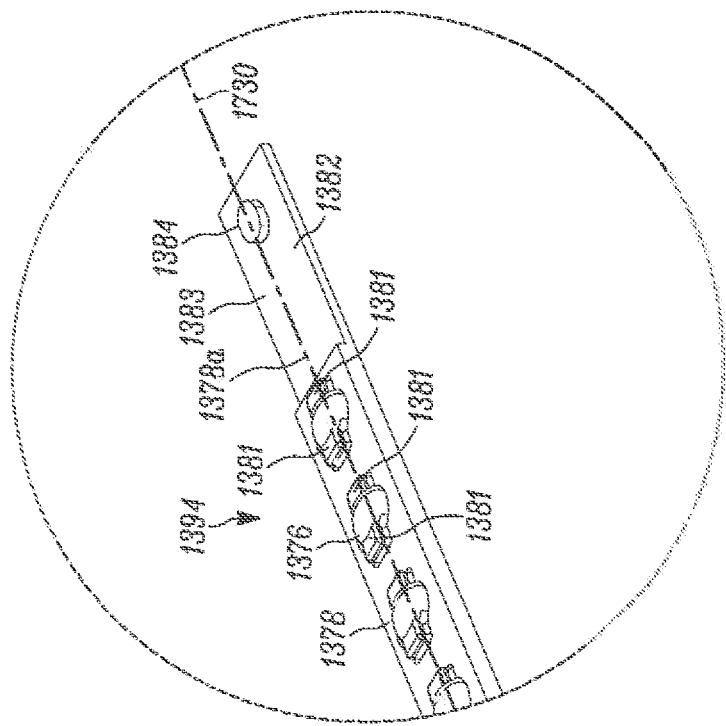
FIG. 27 is a schematic enlarged perspective view of an end portion the rolling bearing strip of FIG. 25 as seen within the dashed line labeled FIG. 27 in FIG. 25.
Figure 26:
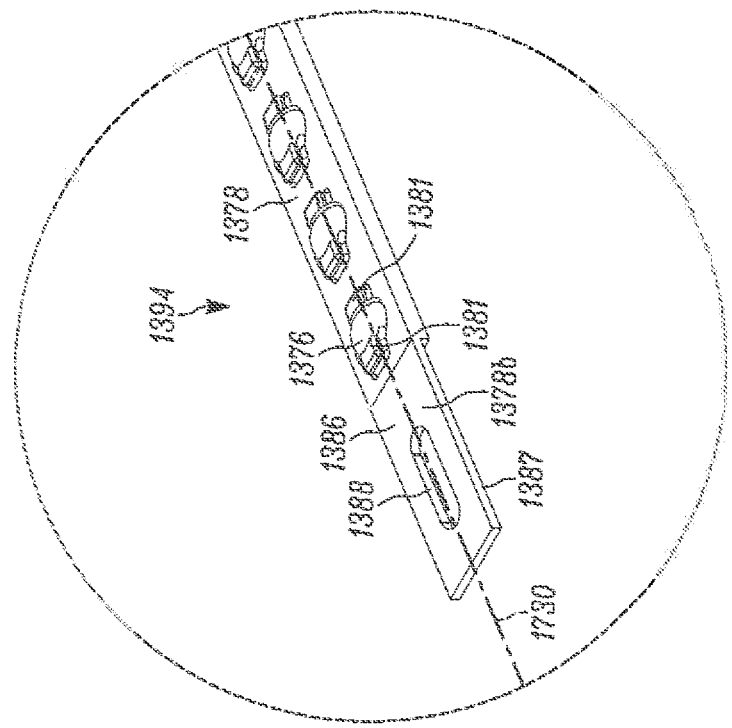
FIG. 26 is a schematic enlarged perspective view of an end portion the rolling bearing strip of FIG. 25 as seen within the dashed line labeled FIG. 26 in FIG. 25.
Figure 28:
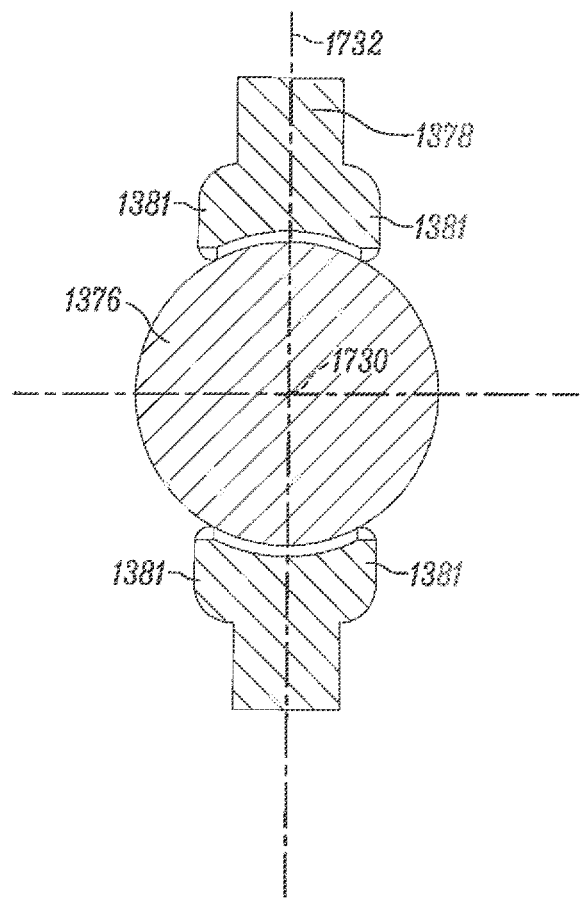
FIG. 28 is a schematic vertical section view of the rolling bearing strip of FIG. 25.
Figure 29:
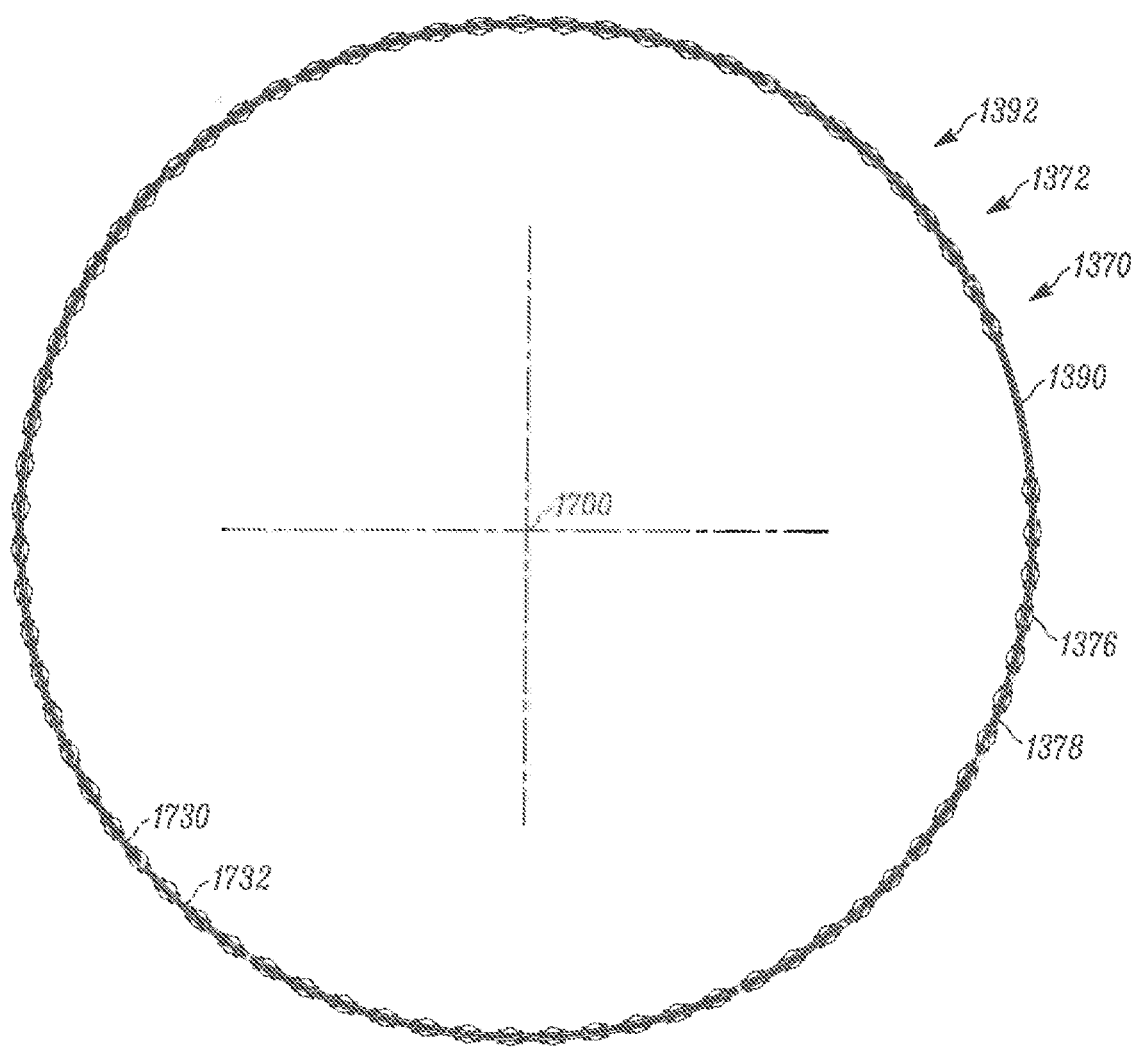
FIG. 29 is a schematic top plan view of the rolling bearing strip of FIG. 25 in an annular condition subsequent to interlocking ends of the separator cage being fused together.
Figure 30:
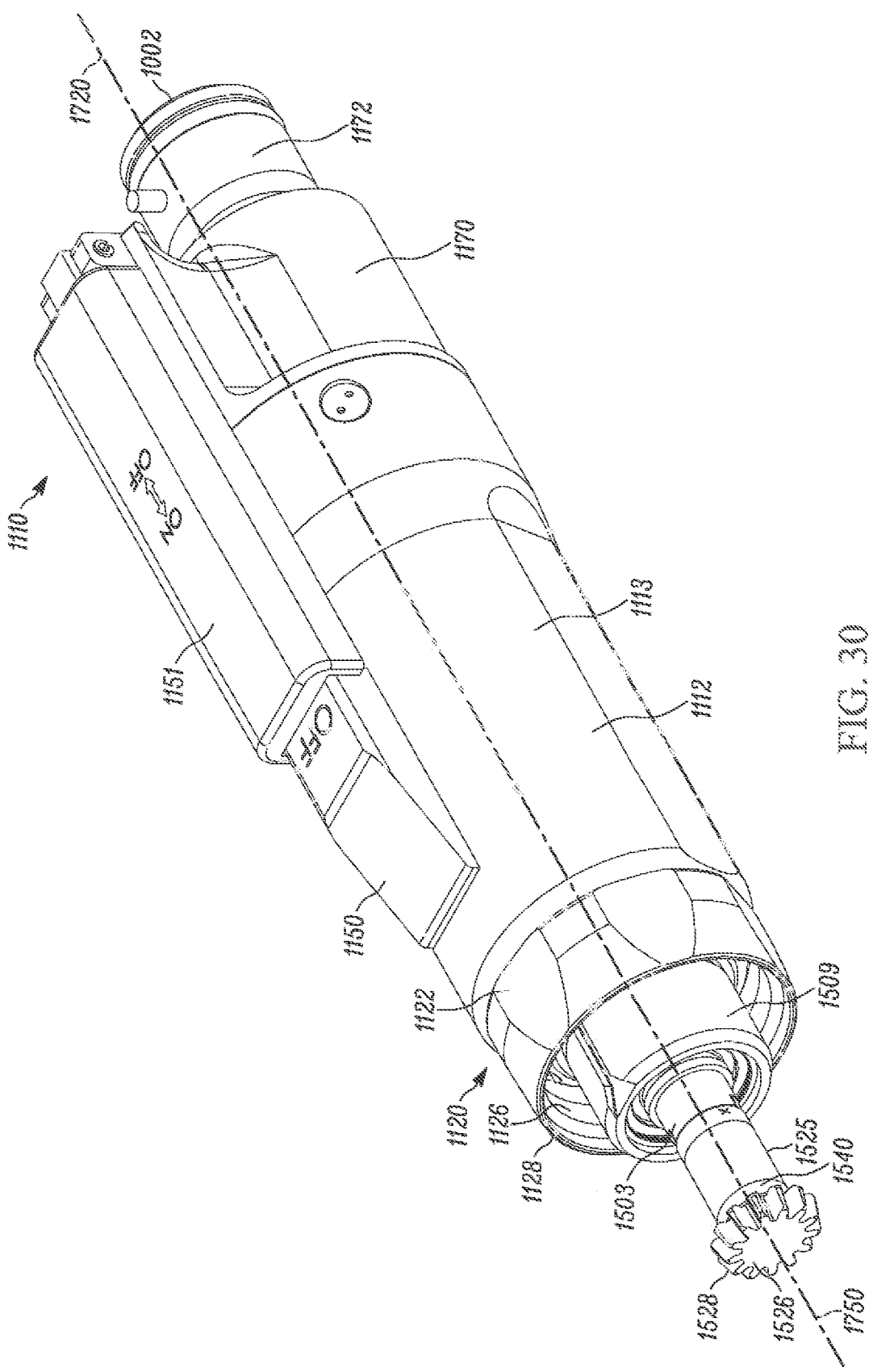
FIG. 30 is a schematic front perspective view of the handle assembly of the power operated dermatome of FIG. 8.
Figure 31:
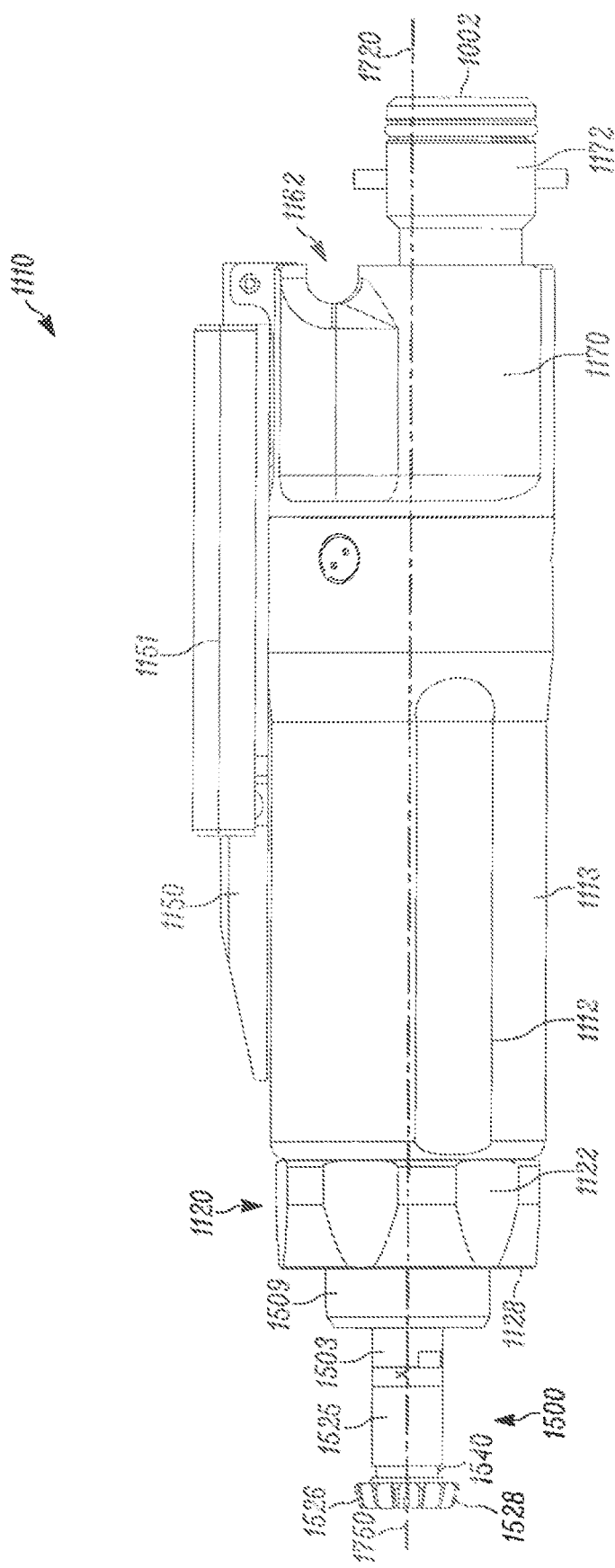
FIG. 31 is a schematic side elevation view of the handle assembly of FIG. 31.
Figure 34:
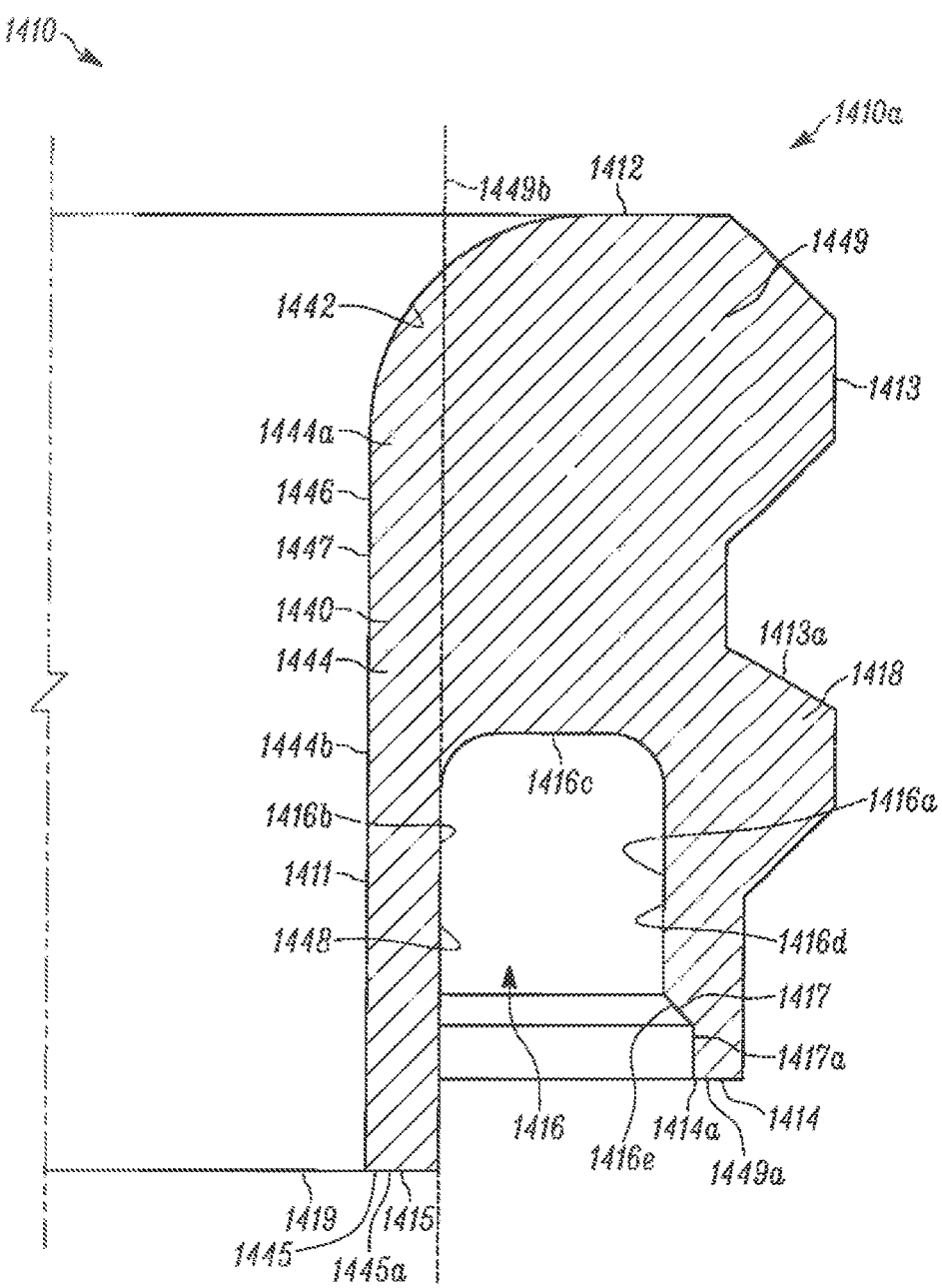
FIG. 34 is a schematic enlarged section view of a portion of the blade housing of the blade housing assembly of FIG. 23 in a forward, circumferentially extending skin deflector portion of the blade housing.

The rear interface or mounting portion 1420 of the blade housing 1410 includes an arcuate gear interface opening 1424 that provides clearance for the pinion gear gear head 1526. The annular blade housing 1410 includes the annular body 1410a which is generally cylindrical in shape and includes the rear interface or mounting portion 1420 and the forward skin deflector portion 1440 which is designed to provide a non-rotating route or path of travel PT for excised material cut by the cutting edge 1360 of the rotary knife blade 1300. In one exemplary embodiment, in the skin deflector portion 1440, the annular body 1410a of the blade housing 1410 includes the annular body 1410a including a blade receiving portion or blade receiving body 1449 and a blade shield 1444, extending radially inwardly from the blade receiving body 1449. The blade shield 1444 comprises a generally cylindrical body 1444a. The shield 1444 includes a lower end 1445 corresponding to the lower end 1419 of the blade housing 1410, an inner wall 1446 and an outer wall 1448. The inner wall 1446 of the shield 1444, which corresponds to and defines a portion of the blade housing inner wall 1411, defines a non-rotating, tissue directing surface 1444b of the shield 1444 that the excised skin layer ETL passes along or traverses the excised skin layer ETL moves from the cutting opening CO to the exit opening EO. The tissue directing surface 1444b of the shield 1444 includes a vertically or axially extending vertical tissue guide portion or surface 1447 that, when viewed in three dimensions, is concentric about and parallel to the blade housing axial or vertical center line 1760 and an arcuate or rounded tissue guide surface 1442 that transitions between the vertical tissue guide surface 1447 of the inner wall 1146 of the shield 1444 and the horizontally extending upper end 1412 of the blade housing 1410. The outer wall 1448 of the shield 1444 extends vertically and shares the second vertical inner wall 1416b of the annular blade channel 1416 of the blade receiving body 1449. Stated another way, the outer wall 1448 of the shield 1444 and the second vertical inner wall 1416b of the annular blade channel 1416 of the blade receiving body 1449 of the annular body 1410a of the blade housing 1410 share the second vertical inner wall 1416b. The outer wall 1448 of the shield 1444 extends axially upwardly from the vertical wall 1416b extending along a vertical cylindrical plane 1449b, which is schematically depicted in FIG. 34 by the vertical dashed line 1449b which is coincident with the second vertical inner wall 1416b of the annular blade channel 1416. That is, the generally cylindrical body 1444a of the shield 1444 extends vertically from the lower end 1419 of the blade housing 1410 to the upper end 1412 of the blade housing 1420 and shares a boundary with the blade receiving body 1449 along the vertical cylindrical plane 1449b. As best seen in FIG. 13, a circumferential extent of the shield 1444 of the forward skin deflector portion 1440 of the blade housing 1410 includes a forward portion of the blade housing 1410 and generally extends between a first circumferential end 1144c and a second circumferential end 1444d. The circumferential ends 1444c, 1444d are marked by a termination of the arcuate tissue guide surface 1442 of the shield inner wall 1446, which is a part of the blade housing inner wall 1411. The blade receiving body 1449 of the annular body 1410a of the blade housing 1410 includes the inverted u-shaped annular blade receiving channel 1416 as well as regions of the blade housing annular body 1410a that are radially outwardly of the cylindrical shield 1444 and regions of the annular body 1410a that are axially above the inverted u-shaped upper or bridging surface 1416c extending between or bridging the radially spaced apart inner walls 1416a, 1416b of the annular blade channel 1416. The second vertical inner wall 1416b is closer radially to the blade housing axial center line 1760 and extends axially downwardly to a greater extent than the first vertical inner wall 1416a. The first vertical inner wall 1416a includes the blade housing frustoconical bearing surface 1417. The blade receiving body 1449 and the shield 1444 share the second vertical inner wall 1416b, which marks a generally vertical boundary 1449b (FIG. 34) between the blade receiving body 1449 and the shield 1444. The blade receiving body 1449 includes the first vertical inner wall 1416a of the annular blade channel 1416 and also includes regions of the annular body extending radially outward from the second vertical inner wall 1416b. The annular blade channel 1416 of the blade receiving body 1449 extends axially upwardly from a lower surface 1449a of the blade receiving body 1449. The lower surface 1449a of the blade receiving body 1449 corresponds generally to the outer lower end 1414 of the lower end 1419 of the blade housing 1410 and a very small portion of the inner lower end 1415 of the lower end 1419 of the blade housing 1410 corresponding to a lower end portion of the vertical inner wall 1416*b* of the annular blade channel 1416. A lower surface 1445*a* of the shield 1444 corresponding to the lower end 1445 of the shield 1444, as defined by the inner lower end 1415 of the lower end 1419 of the blade housing 1410 is axially lower than a portion of the lower surface 1449*a* of the blade receiving body 1449 corresponding to the outer lower end 1414 of the lower end 1419 of the annular blade housing 1410.

Figure 33:
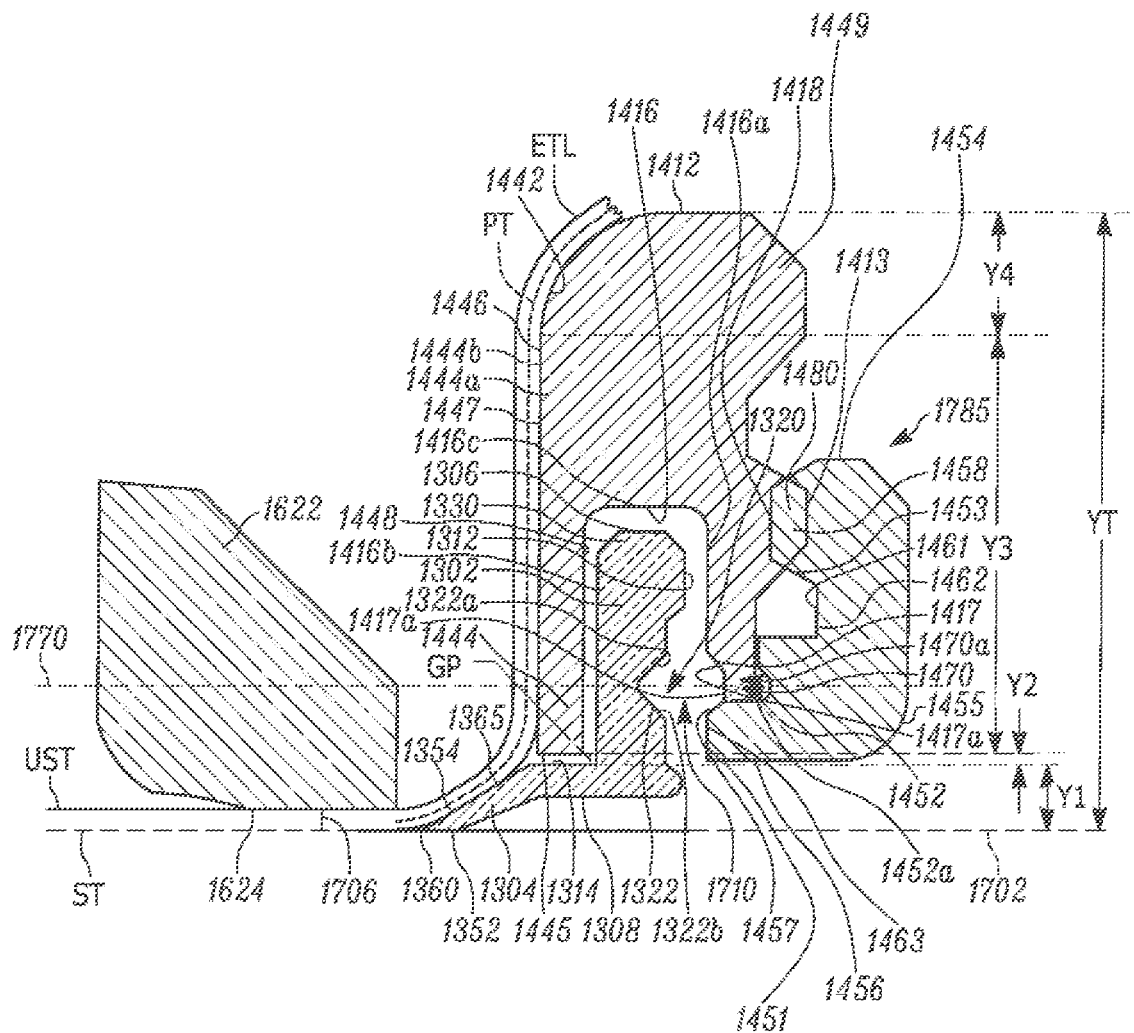
FIG. 33 is a schematic enlarged section view of a portion of the head assembly of the power operated dermatome of FIG. 8 schematically illustrating a tissue excising procedure wherein a layer of tissue is excised and is depicted as traversing along a path of travel from a cutting opening to an exit opening of the head assembly.

Advantageously, an axial extent (labeled Y3 in FIG. 33) of the vertical guide surface 1447 is large compared to an overall axial extent (labeled YT in FIG. 33) of the path of travel PT of an excised tissue layer ETL cut by the blade cutting edge 1360 and moving from the cutting opening of the blade 1300 to the exit opening EO defined by the upper end 1412 of the blade housing 1410. That is, because both the cutting opening CO and the exit opening EO are centered about the blade central axis of rotation 1700 and the blade housing axial center line 1740 and have similar diameters, the shortest distance between the cutting opening CO and the exit opening EO would be a straight vertical line or, viewed in three dimensions, a vertically oriented cylindrical surface. Having the path of travel PT for the excised tissue layer ETL being as short a distance as possible when moving from the cutting opening CO to the exit opening EO is advantageous since the longer the distance traveled, the greater the friction that has to be overcome as the excised tissue layer ETL passes over a tissue directing surface 1365 of the rotary knife blade 1300 defined by the inner wall 1354 of the blade portion 1304 and proceeds to move along or traverse the tissue directing surface 1444*b* of the blade housing 1410. As a length of the path of travel PT of the excised tissue layer ETL increases and as the friction that must be overcome accordingly increases, the undesirable tendency for the excised tissue layer ETL to not flow smoothly or to bunch up or fold over itself as the excised tissue layer ETL moves along the path of travel PT also increases. Accordingly, the vertical guide surface 1447 of the blade housing tissue directing surface 1444*b* advantageously provides a straight, non-rotating, vertical line path of travel PT for the excised tissue layer ETL. As previously discussed, the rounded guide surface 1442 is provides to mitigate ripping or tearing of the excised tissue layer ETL as it exits the blade housing 1410, thus, a relatively axially short rounded guide surface 1442 is provided. Referring to FIG. 33, in one exemplary embodiment, the axial distances from the cutting opening CO to the exit opening EO are as follows: cutting blade axial distance Y1 corresponding to the tissue directing surface 1365 of the blade 1300 is approximately 0.063 in.; an axial gap GP axial distance Y2 providing clearance between the blade portion 1304 of the rotary knife blade 1300 and the lower end 1445 of the shield 1444 is approximately 0.009 in.; the vertical axial distance Y3 surface defined by the vertical tissue directing surface 1447 of the inner wall 1446 of the shield is approximately 0.428 in.; and the arcuate distance Y4 defined by the rounded guide surface 1442 is approximately 0.125 in. The overall axial distance YT from the cutting opening CO to the exit opening EU is approximately 0.625 in. Thus, in one exemplary embodiment, the vertical axial distance Y3 defined by the vertical tissue directing surface 1447 represents approximately 68% (0.428/0.625) of the overall or total axial distance YT, that is, the vertical axial distance Y3 defined by the vertical tissue directing surface 1447 advantageously represents greater than 50% of the overall or total axial distance YT between the cutting opening CO and the exit opening EO.

Additionally and advantageously, the tissue directing surface 1444*b* of the shield 1444 is not rotating, that is, it is stationary with respect to the rotating blade 1300. During certain tissue cutting or tissue excising operations with a power operated dermatome, excised skin tissue contacting an inner wall of the blade portion of the rotary knife blade may tend to rotate with the rotating knife blade, albeit at a much slower rotational velocity. That is, during certain tissue excising operations, the excised skin tissue may tend to slide along the inner wall of the knife blade in the direction of blade rotation. Rotation of the excised skin tissue, even at a low rotational speed, is undesirable because the excised tissue could potentially wrap around a depth gauge plate and/or migrate into the pinion gear/knife blade driven gear interface region. The stationary shield 1444 of the power operated dermatome 1000 advantageously mitigates the problem of rotation of the excised skin tissue by providing the stationary tissue-directing surface 1444*b* of the shield 1444 for receiving the excised tissue layer ETL a very short distance after the tissue layer is cut by the cutting edge 1360 of the rotary knife blade 1300. As depicted schematically in FIG. 33, an upper layer of tissue, for example, skin tissue ST is to be excised by the dermatome 1000. The dermatome 1000 is positioned and moved horizontally along the upper surface UST of the skin tissue ST. An axial position of a planar lower surface 1624 of a depth gauge 1622 of the depth gauges assembly 1600 determines a depth of cut 1706 of the skin tissue ST. As the planar lower surface 1624 of the depth gauge 1622 slides across the upper surface UST of the skin tissue ST, the cutting edge 1360 of the rotating rotary knife blade 1300 cut the skin tissue ST forming an excised tissue layer ETL. The excised tissue layer ETL follows a path of travel PT from the cutting opening CO where the excised tissue layer ETL is formed by the cutting edge 1360 to the exit opening BO where the excised tissue layer ETL leaves the interior region 1780 defined by the combination of the rotary knife blade 1300 and annular blade housing 1410. Moving along the path of travel PT, the excised skin layer slides up and across the frustoconical tissue directing surface 1365 defined by the inner wall 1354 of the blade section 1304 of the rotary knife blade 1300. In this portion of the path of travel PT, the excised skin tissue layer ETL is subjected to the rotational forces caused by the rotation of the blade 1300. However, after a short distance along the path of travel PT, the excised skin tissue layer ETL traverses the axial gap GP between the blade 1300 and the lower end 1445 of the shield 1444 of the blade housing 1410 and moves onto the non-rotating, generally vertical tissue directing surface 1444*b* of the blade shield 1444 as the layer ETL moves upwardly toward the exit opening EO. Specifically, the excised skin layer ETL first moves onto and upwardly along the vertical tissue guide surface 1447 of the inner wall 1446 of the shield 1444, which constitutes a lower portion of the tissue directing surface 1444*b* of the shield 1444, where a majority of the axial distance YT between the cutting and exit openings CO, EO is advantageously traversed in a straight upward or vertical direction UP (that is, in an upward direction UP parallel to the blade central axis of rotation 1700 and the blade housing axial center line 1760 for a vertical portion of the path of travel PT of the excised skin layer ETL. At an upper end of the vertical tissue guide surface 1447, the excised skin tissue ETL transitions onto an upper portion of the tissue directing surface 1444*b* of the shield 1444, namely, onto the arcuate or curved tissue guide surface 1442 of the blade housing shield inner wall 1446. The arcuate tissue guide surface 1442 routes the excised skin layer ETL vertically upwardly and radially outwardly and advantageously mitigates the chance of the excised skin tissue ETL being torn or cut by the upper end of the shield 1444 as the operator of the dermatome pulls the excised skin tissue ETL upwardly and outwardly away from the exit opening EO to avoid undesirable bunching or folding of the excised skin layer ETL as the dermatome moves along a cutting path to obtain an excised skin layer of a desired length. Tearing or cutting of the excised skin layer ETL might occur, for example, if there was a sharp corner at an upper end of the shield, i.e., a sharp corner at an intersection of the inner wall 1446 of the shield and the upper end of the blade housing 1412, which would serve as the upper end of the shield 1444, as the operator pulled the excised skin layer ETL upwardly and outwardly from the exit opening EO during an excision cutting path.

A middle portion 1413a of the outer wall 1413 of the annular blade housing 1410 includes the threaded portion 1418 that, in one exemplary embodiment, includes a single thread that threads onto a corresponding single thread of a threaded portion 1458 formed on an upper inner surface 1453 of the blade lock ring 1450. The threaded portion 1418 comprises a portion of an outer surface of the blade receiving body 1449 corresponding to the blade housing outer wall 1413. The circumferential extent of the single thread is approximately 1½ revolutions around the outer wall 1413. The threaded portion 1458 of the lock ring 1450 similarly has a single thread with a circumferential extent of 1½ revolutions around the upper inner surface 1453 of an inner wall 1461 of the lock ring 1450. The provision of such a 1½ revolution thread in the threaded portions 1418, 1458 means that an operator can remove the lock ring 1450 from the blade housing 1410 with a approximately a 1½ turn (approximately 540°) relative rotation of the lock ring 1450 with respect to the blade housing 1410. A stop mechanism is provided to prevent the operator from over tightening the lock ring 1450. Specifically, in one exemplary embodiment, a flat surface or stop 1414a of the outer lower end 1414 engages a corresponding flat surface or stop 1452a formed on a horizontally extending shoulder 1452 of a lower inner surface 1451 of an inner surface 1461 of the lock ring 1450 to prevent over tightening of the blade lock ring 1450.

The annular blade lock ring 1450 is generally cylindrical in shape and, like the blade housing 1410, is centered about and concentric with the blade housing axial center line 1740. The lock ring 1450 includes a generally planar upper end 1454 and an axially spaced apart generally planar lower end 1456. The lock ring includes an inner surface or inner wall 1461 and a radially spaced apart outer surface or outer wall 1455. The inner wall 1461 includes an upper inner surface 1453 and a lower inner surface 1451. The upper inner surface 1453 of the inner wall 1461 includes a threaded region or portion 1458 near the upper end 1454 and a recessed or relief portion 1462 axially below the threaded portion 1458. The lower inner surface 1451 of the inner wall 1461 includes a vertical portion 1463 that is adjacent the lower end 1456 and represents the radially innermost portion of the inner surface 1461, that is, the portion of the inner surface 1461 that is closest radially to the blade housing axial center line 1760. The lower inner surface 1451 of the inner wall 1461 also includes a horizontally extending shoulder 1452. The frustoconical bearing surface or bearing face 1457 of the lock ring 1450 extends between the vertical portion 1463 and the horizontal shoulder 1462 of the inner wall 1461. Viewed in three dimensions, the frustoconical bearing surface 1457 is annular and is a frustum of a right angled cone and converges proceeding in the downward direction DW, that is, in a direction proceeding toward the lower end 1456 of the lock ring 1450. In one exemplary embodiment, the bearing surface 1457 is angled at approximately a 45° angle with respect to the blade housing axial center line 1760. The lock ring bearing surface 1457 is axially aligned with but spaced apart from the corresponding bearing surface 1417 of the blade housing 1410. The lock ring bearing surface 1457 is radially aligned with the opposing frustoconical bearing face 1322b of the bearing surface 1322 of the blade bearing race 1322. Taken together, the axially aligned bearing surfaces 1417, 1457 of the blade housing 1410, 1450 form a combination v-shaped bearing race 1470 that is radially aligned with and is substantially the mirror image of the blade v-shaped bearing race 1320. An annular passageway 1710 is formed between the combination v-shaped bearing race 1470 of the blade housing 1410 and the lock ring 1450 and the v-shaped bearing race 1320 of the rotary knife blade 1300. The annular rolling bearing strip 1372 of the rolling bearing structure 1370 traverses through the annular passageway 1710. The outer surface 1455 includes four peripherally spaced apart vertically oriented slots or cavities 1459 in the outer surface 1455 of the blade lock ring 1450. To install or affix the rotary knife blade 1300 to the blade housing assembly 1400, with the blade lock ring 1450 removed, the head assembly 1200 is turned upside down and the rotary knife blade 1300 is placed in the upside down blade housing 1410. The plurality of ball bearings 1376 of the annular rolling bearing strip 1372 assembled and affixed to the rotary knife blade 1300 rest on the bearing race 1417 of the blade housing 1410 thereby the rotary knife blade 1300 is supported by the blade housing 1410. The lock ring 1450 is then positioned with respect to the blade housing 1410 such that the mating threaded portions 1418, 1458 of the blade housing 1410 and the lock ring 1450 are in proximity for threading and then the lock ring 1450 is threaded onto the blade housing 1450 to complete the installation. When the blade lock ring 1450 is removed from the blade housing 1410, turning the head assembly 1200 upside down causes the rotary knife blade 1300 to fall out of the blade housing 1410 thereby removing the blade 1300 from the blade housing assembly 1400.

As previously noted, the threaded portion 1458 of the lock ring 1450 includes a single thread with a circumferential extent of 1½ revolutions around an upper inner surface 1453 of an inner wall 1461 of the lock ring 1450. The provision of such a 1½ revolution thread in the threaded portions 1418, 1458 of the blade housing 1410 and blade lock ring 1450 means that an operator can remove the lock ring 1450 from the blade housing 1410 with a approximately a 1½ turn (approximately 540°) relative rotation of the lock ring 1450 with respect to the blade housing 1410. Also as explained previously, the upper end or upper surface 1454 of the lock ring 1450 includes the axially recessed region 1454a that extends circumferentially about the a portion of the annular upper end 1454. When the lock ring 1450 is fully threaded connected to the blade housing 1410 such that the stop 1414a of the outer lower end 1414 of the blade housing 1410 contacts and bears against the horizontal shoulder 1462, the recessed region 1454a of the upper surface 1454 of the lock ring 1450 is radially aligned with the arcuate gear interface opening 1424 of the mounting portion 1420 of the blade housing 1410. Advantageously, the recessed region 1454a of the blade lock ring upper end 1454 provides sufficient clearance for the pinion gear gear head 1526 so that when the attachment assembly 1120 is sufficiently loosened so that the handle assembly 1110 and the head assembly 1200 are decoupled and moved apart, the gear head 1526 does not undesirably contact the upper end 1454 of the blade lock ring 1450 with potential damage to the gear head 1526. In one exemplary embodiment, when viewed from the blade housing axial center line 1460, the recessed region 1454*a* subtends a recess angle RA of approximately 50° and an axial extent or depth of the recessed region 1454*a*, as compared to the remainder of the upper end 1454 is approximately 0.130 in. The recess angle RA subtending 50° of the recessed region 1454*a* advantageously provides for sufficient circumferential extent of the recessed region to account for manufacturing tolerance variations that may result in the single threads of the threaded portions 1418, 1458 of the blade housing 1410 and blade lock ring 1450 requiring either at slightly more or slightly less than the nominal one rotation to reach the stop contact point where the blade housing stop 1414*a* contacts the lock ring shoulder 1462. While the axial depth of the recessed region 1454*a* is sufficient for clearance purposes, as explained above, it also extends into or breaches the threaded portion 1458. Thus, the recess region could not simply be increased to extend around the entirety of the planar upper end 1454 of the lock ring 1450. Thus, the selected recess angle RA provides for sufficient clearance to account for manufacturing tolerance issues, while minimizing the circumferential extent of the breach or interruption of the threaded portion 1458. Axially extending transition regions 1454*b* extend from opposite ends of the recessed region 1454*a* to the general extent of the non-recessed remainder of the planar upper end 1454 of the lock ring 1450.

Rotary Knife Blade 1300

The annular rotary knife blade 1300 (FIGS. 9, 11 and 17) includes a body section or body portion 1302, a blade section or blade portion 1304, as previously described, with respect to the rotary knife blade 300 of the first exemplary embodiment. The body portion 1302 includes the outer wall 1312. Extending radially inwardly into a vertical extent of the outer wall 1312 is the v-shaped bearing race 1320. The v-shaped bearing race 1320 defines a v-shaped bearing surface 1322 that includes frustoconical upper and lower blade bearing surfaces or faces 1322*a*, 1322*b*, the upper and lower bearing faces 1322*a*, 1322*b* are axially aligned. Viewed in three dimensions, the frustoconical upper and lower bearing surfaces 1322*a*, 1322*b* are annular and comprise frustums of respective right angled cones. The upper bearing surface 1322*a* converges proceeding in the upward direction UP, that is, converges in a direction proceeding toward an upper end 1306 of the blade body portion 1302, while the lower bearing surface 1322*b* converges proceeding in the downward direction DW, that is, converges in a direction proceeding toward the lower end 1308 of the blade body 1302. In one exemplary embodiment, the upper and lower bearing surfaces 1422*a*, 1422*b* are angled at approximately a 45° angle with respect to the blade central axis of rotation 1700.

The blade portion 1304 includes the cutting edge 1360 at the lower end 1352 of the blade portion 1304 which corresponding to the lower end 1368 of the blade 1300. The cutting edge 1360 defines the cutting opening CO of the blade 1300. In one exemplary embodiment, the cutting opening CO is approximately 4.00 in. Although, it should be understood that the size of the cutting opening and other dimensions and configurations of the rotary knife blade 1300, as well as other components of the power operated dermatome 1000, may be modified as necessary depending specific requirements of a particular cutting/trimming/excision application. The inner wall 1354 of the blade portion 1304 compromises the tissue directing surface 1365 of the rotary knife blade 1300.

Continuous Rolling Bearing Structure 1370

Advantageously, a continuous rolling bearing structure 1370 is provided to rotatably support the rotary knife blade 1300 with respect to the blade housing assembly 1400. In one exemplary embodiment, the continuous rolling bearing structure 1370 is a continuous annular bearing strip 1372 that is sized and configured to fit into the concave bearing race 1320 extending radially inwardly in an outer wall 1312 of the body portion 1302 of the rotary knife blade 1300. When assembled or installed, the continuous rolling bearing structure 1379 may be viewed as a permanent part of the rotary knife blade 1300 that traverses in a circular path of travel within the bearing race, a path of travel that is centered about the central axis of rotation 1700 of the blade 1300. In one exemplary embodiment, the continuous rolling bearing structure 1379 comprises the annular rolling bearing strip 1372 partially disposed within the bearing race 1320 and wherein the plurality of ball bearings 1376 bear against frustoconical upper and lower blade bearing faces 1322*a*, 1322*b* of a blade bearing surface 1322 defined by the blade bearing race 1320. In one exemplary embodiment, the frustoconical upper bearing face 1322*a*, viewed in three dimensions, is a frustum of a right angled cone, converging in a direction proceeding toward a lower end 1368 of the rotary knife blade 1300, while the frustoconical lower bearing face 1322*a*, viewed in three dimensions, is a frustum of a right angled cone, converging in a direction proceeding toward an upper end 1367 of the rotary knife blade 1300.

Advantageously, as best seen in FIGS. 25-28, the annular bearing strip 1372 is fabricated as an elongated, flexible separator cage 1378 having a series of spaced apart pockets 1381. Each pocket 1381 rotatably supports a ball bearing of a plurality of ball bearings 1376. At opposite end portions 1378*a*, 1378*b* of the separator cage 1378 are first and second interlocking ends 1382, 1386. Prior to assembly to the bearing race 1320 of the blade 1300 and prior to fusing the first and second interlocking ends 1382, 1386 to form a fused connection 1390 of the first and second end portions 1378*a*, 1378*b* and thereby form a continuous annular band 1392 of the separator cage 1378, the separator cage 1378 comprises an elongated, linear segment 1394 with disconnected end portions 1378*a*, 1378*b* that extends along a longitudinal extending center line 1730 of the separator cage 1378 and rotatably supports the plurality of spaced apart ball bearings 1376.

The annular bearing race 1320 extends radially inwardly into an outer wall 1312 of the body portion 1302. The annular rolling bearing strip 1372 of the continuous rolling bearing structure 1370 includes the elongated, flexible separator cage 1378 supporting a plurality of spaced apart ball bearings 1376 in pockets 1381 formed along the longitudinal extent of the cage 1378. The separator cage 1378 is characterized by a center line 1730 which extends longitudinally through a center of the separator cage 1378 and a vertical longitudinal plane 1732 that is coincident with the longitudinal center line and extends vertically through and vertically bisects the separator cage 1378, when the separator cage 1378 is viewed in section orthogonally to a longitudinal extent of the separator cage 1378. At one end, the separator cage 1378 includes the first interlocking end 1382 having a planar surface 1383 extending along a longitudinally extending center line 1730 of the separator cage 1378. A projection 1384 extends orthogonally from the planar surface 1383 and extends orthogonally with respect to the center line 1730 and the vertical longitudinal plane 1732. At the opposite end, the separator cage 1378 includes a second interlocking end 1386 having a planar surface 1387 in facing arrangement with the planar surface 1383. The second interlocking end 1386 also includes an opening 1388 extending orthogonally with respect to the center line 1730 of the separator cage 1378 and the vertical longitudinal plane 1732. The opposing planar surfaces 1383, 1387 are coincident with the vertical longitudinal plane 1732. A longitudinal extent of the opening 1388 as viewed along the center Hike 1730 is greater than a longitudinal extent of the projection 1384 as viewed along the center line 1730 to advantageously provide for a measure of adjustability of a diameter or circumference of the separator cage 1378 as the separator cage is installed on the bearing race 1320 of the rotary knife blade 1300. That is, because of manufacturing tolerance issues, it is difficult to produce separator cages 1378 with exact lengths. Accordingly, adjustment of the length of the separator cage 1378 is needed for installation for proper fit on a particular rotary knife blade 1300 (the length of the separator cage 1378 corresponds to the circumference of the separator cage 1378, as installed as the annular rolling bearing strip 1372 on a particular rotary knife blade 1300). Accordingly, the circumferential adjustability of the separator cage 1378 provides a degree of dimension flexibility when the separator cage 1378 is installed in the bearing race 1320. The configuration of opposing planar surfaces 1383, 1387 of the first and second interlocking ends 1382, 1386 being positioned in facing relationship prior to fusing of the end portions 1378a, 1378b advantageously provides for a fused connection 1390 between the first and second interlocking ends 1383, 1387 wherein a horizontal width of the fused connection 1390 is within the outer diameters of the plurality of spaced apart ball bearings 1376.

Once the continuous rolling bearing strip 1372 of the continuous rolling bearing structure 1370 is installed in place within the annular bearing race 1320 of the blade body 1302, the plurality of ball bearings 1376 of the annular rolling bearing strip 1372 bear against and rollingly engage the corresponding frustoconical bearing surfaces 1322, 1417, 1457 of the blade 1300, the blade housing 1410 and the lock ring 1450, respectively, to provide a rolling bearing structure for the blade 1300 and thereby support the blade 1300 for rotation about its central axis of rotation 1700. When the power operated dermatome 1000 is fully assembled, a plane though center points of each of the respective plurality of ball bearings 1376 of the annular rolling bearing strip 1372 define a rotational plane 1770 of the rotary knife blade 1300. The rotational plane 1770 is substantially parallel to the cutting plane 1702 of the blade 1300 and, like the cutting plane 1702, is orthogonal to the blade central axis of rotation 1700. Also, like the cutting plane 1702, the rotational plane 1770 is intersected or pierced by the handle assembly longitudinal axis 1720. The rotational plane 1770 is parallel to the head assembly central horizontal axis 1740. As the rotary knife blade 1300 is driven for rotation about its central axis 1700, the following occur: a) the plurality of ball bearings 1376 rotate within their respective pockets 1381 and provide bearing support for the blade 1300 by bearing against the bearing surfaces 1417, 1457 of the blade housing 1410 and lock ring 1450; and b) the annular rolling bearing strip 1372 moves or traverses along a circular path of travel within an annular passageway 1710 defined by opposing frustoconical bearing surfaces 1322, 1417, 1457 of blade 1300, blade housing 1410 and lock ring 1450. It should be noted that the separator cage 1378 does not provide bearing support to the blade 1300 and is not intended to make bearing contact with any of the opposing bearing surfaces 1322, 1417, 1457. As the annular passageway 1710 is centered about the blade central axis of rotation 1700, the annular rolling bearing strip 1372 also traverses or has the circular path of travel centered about the blade central axis of rotation 1700. Upon installation, the continuous rolling bearing structure 1370 defines a portion of an outer peripheral surface 1369 of the rotary knife blade 1300 and defines a convex bearing surface 1380 of the rotary knife blade 1300.

Figure 32:
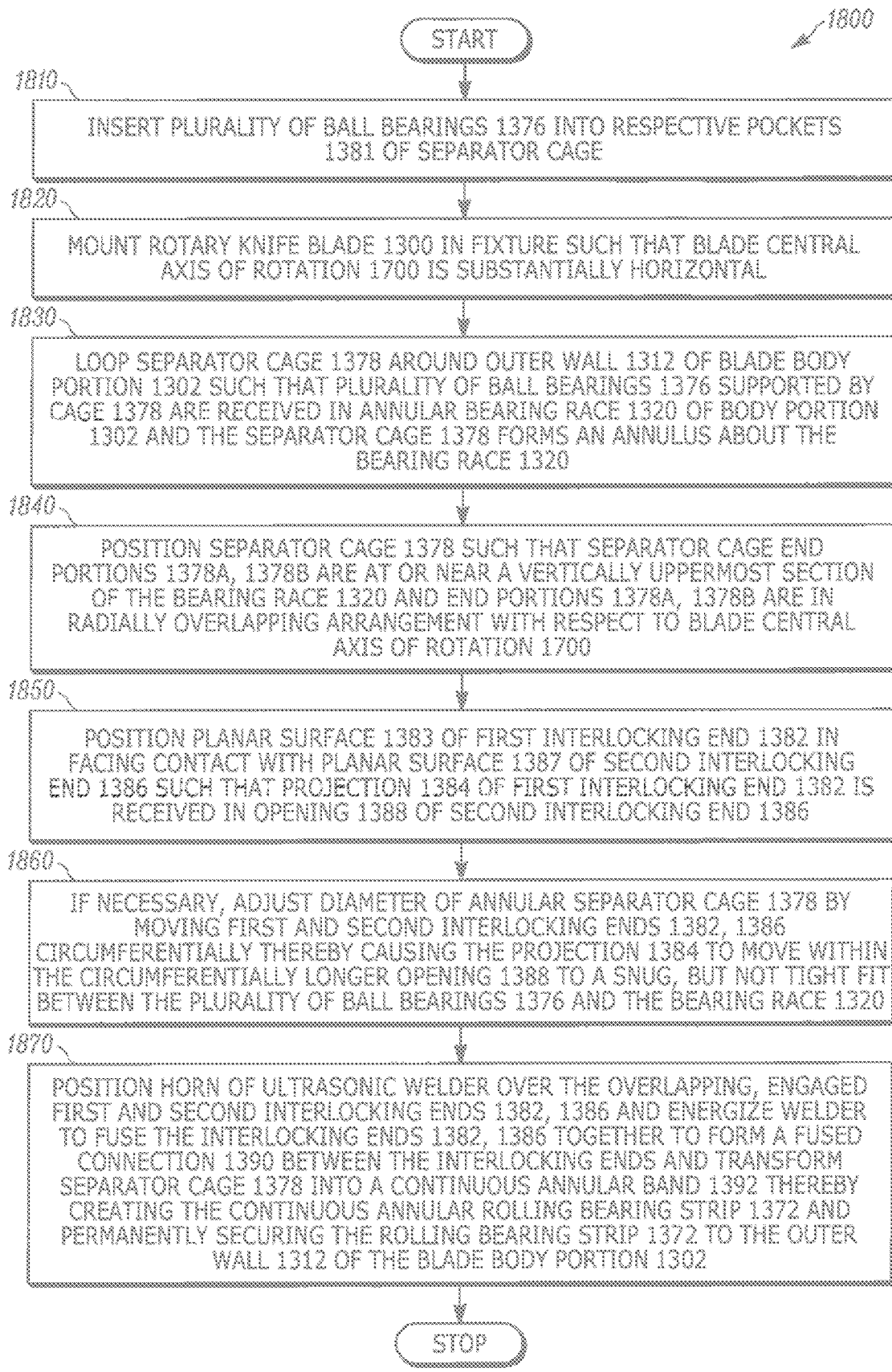
FIG. 32 is a flow chart depicting selected steps in an assembly method of the rolling bearing strip to the rotary knife blade in the power operated dermatome of FIG. 8.

In one exemplary embodiment, a method of fabrication and assembly of the annular rolling bearing strip 1372 onto the rotary knife blade is illustrated schematically at 1800 in a flow chart in FIG. 32. The steps to fabricate and position the continuous rolling bearing structure 1370 within the annular bearing race 1320 of the blade 1300 including the following steps. 1) At step 1810, insert the plurality of ball bearing 1376 into respective pockets 1381 of the separator cage 1378. 2) At step 1820, mount the rotary knife blade 1300 in a holding fixture such that the blade central axis of rotation 1700 is horizontal, that is, the blade is positioned on its side with a portion of the peripheral outer wall or outer surface 1369 of the blade is facing vertically upward. 3) At step 1830, loop the separator cage 1378 around the bearing race 1320 to form an annulus with the separator cage 1378 such that approximately a one half diameter of each of the ball bearings of the plurality of ball bearings 1376 separator cage interfits into and are received within the bearing race 1320. 4) At step 1840, position the separator cage such that the separator end portions 1378a, 1378b are at or near a vertically uppermost section of the bearing race 1320 and the end portions are in radially overlapping arrangement with respect to the blade central axis of rotation 1700. 5) At step 1850, position the planar surface 1383 of the first interlocking end in facing contact with the planar surface 1387 of the second interlocking end 1386 such that the projection 1384 of the first interlocking end 1382 is received in the opening 1388 of the second interlocking end 1386 to lock the ends together. 6) At step 1860, if necessary, adjust the diameter of the now annular separator cage 1378 by moving the first and second interlocking ends 1382, 1386 circumferentially thereby causing the projection 1384 to move within the circumferentially longer opening 1388 to achieve a snug, but not tight fit between the plurality of ball bearings 1376 and the bearing race 1320. That is, the plurality of ball bearings 1376 snuggly, but not tightly, bear against the upper and lower frustoconical upper bearing faces 1322a, 1322b of the bearing race 1320. As noted above, the additional longitudinal extent of the opening 1388 compared to the longitudinal extent of the projection 1384 advantageously provides for adjustment of the annular diameter of the separator cage 1378, as installed in the blade bearing race 1320, due to variation in diameter of the blade bearing race 1320, the longitudinal length of the separator cage 1378, the diameter of the plurality of ball bearings 1376, etc. 7) At step 1870, position a horn of an ultrasonic welder such that the horn is in contact with the first and second interlocking ends 1382, 1384 of the separator cage 1378 and energized the ultrasonic welder for a sufficient period to fuse or weld the interlocking ends 1382, 1384 together to form the fused connection 1390 between the interlocking ends. With the fused connection 1390 between the interlocking ends 1382, 1384 of the separator cage 1378, the separator cage 1378 is no longer a linear segment but rather a continuous annular band 1392.

The fused connection 1390 of the end portions of the separator cage 1378 forms or fabricates the continuous annular bearing strip 1372 and, at the same time, the continuous annular bearing strip 1372 is been permanently assembled, installed or affixed to the outer wall 1312 of the rotary knife blade body portion 1302. Advantageously, the ultrasonic welding process welds or bonds the overlapping end portions 1378a, 1378a with any significant increase in the size or distortion of the shape of the overlapping end portions. That is, the fused or welded connection 1390 is streamlined as viewed along the vertical center plane 1732 of the separator cage 1378, being not significantly greater in cross sectional area, width or height, as compared with the unwelded or unfused overlapping end portions 1378a, 1378b. The interlocking ends 1382, 1384 advantageously facilitate the assembly and ultrasonic welding process. Specifically, the interlocking of the projection 1384 of the first interlocking end 1382 into the opening 1384 of the second interlocking end 1384 keep the overlapping end portions 1378a, 1378b of the separator cage 1378 from moving, sliding or falling away from each other as the horn of the ultrasonic welder is moved into contact with the overlapping end portions 1378a, 1378b of the separator cage 1378.

During fabrication of the rolling bearing strip 1372, the ultrasonic welding process is used to fuse or weld the first and second end portions 1378a, 1379b, specifically, the first and interlocking ends 1382, 1386 together to form the permanent fused or welded connection 1390 that transforms the separator cage 1378 into the continuous annular band 1392 and thus creates the annular rolling bearing strip 1372. The annular rolling bearing strip 1372 is the continuous rolling bearing structure 1370 that supports the rotary knife blade 1300 for rotation about its central axis of rotation 1700 with respect to the blade housing 1410 and the lock ring 1450. Since the rolling bearing strip 1392 is permanently, but rotatably, affixed to bearing race 1320 of the blade body portion 1302, it may be considered as a part of the rotary knife blade 1300 since during assembly of the blade 1300 and the blade housing 1410, the blade 1300, with the attached rolling bearing strip 1392, is inserted into a bottom end of the blade housing 1410 and secured in place by the lock ring 1450 being threaded onto the blade housing 1410. That is, the interlocking ends 1382, 1386, fused together by the ultrasonic welding process are transformed or fabricated into the permanent fused or welded connection 1390 and the separator cage 1378 assumes the form of the continuous annular band 1392 and, at the same time, the rolling bearing strip 1372 is permanently installed on the rotary knife blade outer wall 1312. Because the rolling bearing strip 1372 is permanently secured to the knife blade 1300 it can be viewed as forming a convex bearing surface 1380 of the rotary knife blade 1300 and forming a portion of the outer peripheral surface 1369 of the rotary knife blade 1300. Once the continuous rolling bearing strip 1372 of the continuous rolling bearing structure 1370 is in place within the annular bearing race 1320 of the blade body 1302, the plurality of ball bearings 1376 of the annular rolling bearing strip 1372 bear against and rollingly engage the corresponding frustoconical bearing surfaces 1322, 1417, 1457 of the blade 1300, the blade housing 1410 and the lock ring 1450, respectively, to provide a rolling bearing structure for the blade 1300 and thereby support the blade 1300 for rotation about its central axis of rotation 1700. As the rotary knife blade 1300 is driven for rotation about its central axis 1700, two things occur: a) the plurality of ball bearings 1376 rotate within their respective pockets 1381 and provide bearing support for the blade 1300 by bearing against the bearing surfaces 1417, 1457 of the blade housing 1410 and lock ring 1450; and b) the annular rolling bearing strip 1372 moves or traverses along a circular path of travel within an annular passageway 1710 defined by opposing frustoconical bearing surfaces 1322, 1417, 1457 of blade 1300, blade housing 1410 and lock ring 1450. It should be noted that the separator cage 1378 does not provide bearing support to the blade 1300 and is not intended to make bearing contact with any of the opposing bearing surfaces 1322, 1417, 1457. As the annular passageway 1710 is centered about the blade central axis of rotation 1700, the annular rolling bearing strip 1372 also traverses or has the circular path of travel centered about the blade central axis of rotation 1700. In one exemplary embodiment, a diameter of each of the plurality of ball bearings 1376 is 2 mm, the plurality of ball bearings 1376 and the separator cage is fabricated of nylon or a material with similar characteristics and flexibility. As one of skill in the art will recognize, the necessity to provide operating or running clearance between the continuous rolling bearing structure 1370 and the corresponding frustoconical bearing surfaces 1322, 1417, 1457 of blade 1300, blade housing 1410 and lock ring 1450 so that the blade 1300 spins relatively freely with respect to the blade housing 1410 means that the blade 1300, under certain operating and loading conditions, may move or tilt to a very limited degree with respect to the blade housing 1410. Thus, under certain operating and loading conditions, the central axis of rotation 1700 of the rotary knife blade 1300 may be tilted or angled slightly with respect to an axially extending center line 1760 of the blade housing 1410. Further, it should be appreciate that because of operating or running clearance requirements, not all bearing surfaces 1322, 1417, 1457 of blade 1300, blade housing 1410 and lock ring 1450 will be in constant bearing contact with the plurality of ball bearings 1376 of the rolling bearing strip 1372 around the 360° circumference of the respective bearing surfaces. Additionally, as noted above, the planar, vertically extending relief surface 1417a, that is, the vertex of the v-shaped bearing surface 1470a, may also serve as a vertical bearing surface having intermittent bearing contact with the plurality of ball bearings 1376. Additionally, as one of skill in the art will recognize, other methods of bonding or fusing the interlocking ends 1382, 1386 to provide for a permanent, streamline fused connection 1390, such as, by way of example and not by limitation, heat staking and the like.

In one exemplary embodiment, the handle assembly 1110 may be fabricated of plastic or other material or materials known to have comparable properties and may be formed by molding and/or machining. The attachment assembly 1120, the frame body 1202, and the depth gauge assembly 1600 may be fabricated of aluminum or stainless steel or other material or materials known to have comparable properties and may be formed/shaped by casting and/or machining. The rotary knife blade 1300 and the blade housing assembly 1400 may be fabricated of a hardenable grade of alloy steel or a hardenable grade of stainless steel, or other material or materials known to have comparable properties and may be formed/shaped by machining, forming, casting, forging, extrusion, metal injection molding, additive manufacturing and/or electrical discharge machining or another suitable process or combination of processes.

Axially above or axially spaced above, as used herein, means positioned above as viewed with respect to an axis, for example, the central axis of rotation 1700 of the rotary knife blade 1300, even if the two elements are not in axial alignment with respect to the axis. Similarly, the terms axially below or axially spaced below, as used herein, means positioned below as viewed with respect to an axis, for example, the central axis of rotation 1700 of the rotary knife blade 1300, even if the two elements are not in axial alignment with respect to the axis. Axially extending, as used here, means one element extends from and is positioned above or below a second element with respect to an axis, even if the two elements are not in axial alignment with respect to the axis. Similarly, the terms radially offset from, radially outward of, radially inward of, as used herein, means one element is positioned offset from a second element, as viewed along a radius line extending radially from an axis, for example, the central axis of rotation 1700 of the rotary knife blade 1300, even if the elements are not in radial alignment along a radius line because one element is axially above or below the other.

As used herein, terms of orientation and/or direction such as front, rear, forward, rearward, distal, proximal, distally, proximally, upper, lower, inward, outward, inwardly, outwardly, upwardly, downwardly, horizontal, horizontally, vertical, vertically, axial, radial, longitudinal, axially, radially, longitudinally, etc., are provided for convenience purposes and relate generally to the orientation shown in the Figures and/or discussed in the Detailed Description. Such orientation/direction terms are not intended to limit the scope of the present invention/disclosure, this application, and/or the invention or inventions described therein, and/or any of the claims appended hereto. Further, as used herein, the terms comprise, comprises, and comprising are taken to specify the presence of stated features, elements, integers, steps or components, but do not preclude the presence or addition of one or more other features, elements, integers, steps or components.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and illustrative examples shown and described. Accordingly, departures may be made from such details without departing from the spirit or scope of the applicants' general inventive concept.

What is claimed is:

1. A blade housing assembly for rotatably supporting an annular rotary knife blade for rotation in a power operated rotary excision tool, the blade housing assembly comprising:
    an annular blade housing including an upper end and an axially spaced apart lower end and an inner wall and a radially spaced apart outer wall, the annular blade housing centered about an axially extending center line, the blade housing including a circumferentially extending skin deflector portion including a blade receiving body and a shield extending radially inwardly from the blade receiving body, the blade receiving body including a blade receiving channel extending axially upwardly from a lower surface of the blade receiving body and radially spaced from the inner and outer walls of the annular blade housing, the blade receiving channel includes a first wall, a radially spaced apart second wall closer to the axially extending center line of the blade housing, and a bridging surface between the first and second walls, the first wall includes a bearing surface extending transverse to the axially extending center line of the blade housing, the shield including an inner wall defining a tissue directing surface, the tissue directing surface including a first tissue guide surface extending upwardly from a lower end of the shield, the first tissue guide surface extending substantially parallel to the axially extending center line of the annular blade housing.

2. The blade housing assembly of claim 1 wherein the annular blade housing further includes a threaded portion formed on the outer surface of the annular blade housing and wherein the blade housing assembly further includes an annular blade lock ring including an upper end and an axially spaced apart lower end and an inner wall and a radially spaced apart outer wall, the inner wall of the annular blade lock ring including a threaded portion threadedly engaged with the threaded portion of the annular blade housing to releasably secure the annular blade lock ring to the annular blade housing, the inner wall further including a bearing surface.

3. The blade housing assembly of claim 2 wherein the bearing surface of the annular blade lock ring is disposed on the inner wall between a horizontally extending shoulder of the inner wall and a lower portion of the inner wall adjacent the lower end of the blade lock ring.

4. The blade housing assembly of claim 2 wherein the blade lock ring is centered about the axially extending center line of the annular blade housing.

5. The blade housing assembly of claim 2 wherein the bearing surface of the blade receiving body of the annular blade housing and the bearing surface of the annular blade lock ring form a substantially v-shaped bearing race, a vertex of the bearing race extending in a direction radially away from the axially extending center line of the annular blade housing.

6. The blade housing assembly of claim 1 wherein the first wall of the blade receiving channel of the blade receiving body includes a first generally planar portion extending substantially parallel to the axially extending center line of the blade housing and a second offset portion, the second offset portion defining the bearing surface, the bearing surface being axially spaced from a lower surface of the blade receiving body by a radially outwardly stepped relief surface.

7. The blade housing assembly of claim 1 wherein the tissue directing surface of the shield of the further includes a second arcuate tissue guide surface extending from the first tissue guide surface to an upper end of the blade housing.

8. The blade housing assembly of claim 1 wherein the first wall and the second wall of the blade channel of the blade receiving body both extend vertically substantially parallel to the axially extending center line of the annular blade housing.

9. The blade housing assembly of claim 1 wherein the tissue directing surface of the shield of the blade housing includes a second arcuate tissue guide surface extending between the first tissue guide surface and the upper end of the annular blade housing, an upper end of the second arcuate tissue guide adjacent the upper end of the annular blade housing being further from the axially extending center line of the annular blade housing than a lower end of the second arcuate tissue guide.

10. A blade housing assembly for rotatably supporting an annular rotary knife blade for rotation in a power operated rotary excision tool, the blade housing assembly comprising:
    an annular blade housing including an upper end and an axially spaced apart lower end and an inner wall and a radially spaced apart outer wall and including a shield extending radially inwardly from a blade receiving body, the annular blade housing centered about an axially extending center line, the blade receiving body including a blade channel extending axially upwardly from a lower surface of the blade receiving body, the blade channel including a first wall, a radially spaced apart second wall closer to the axially extending center line, and a bridging portion between the first and second walls, a bearing surface formed on the first wall, the shield including an inner wall defining a tissue directing surface, the tissue directing surface including a first tissue guide surface extending upwardly from a lower end of the shield, the first tissue guide surface extending substantially parallel to the axially extending center line of the annular blade housing.

11. The blade housing assembly of claim 10 wherein the annular blade housing further includes a threaded portion formed on the outer surface of the annular blade housing and wherein the blade housing assembly further includes an annular blade lock ring including an upper end and an axially spaced apart lower end and an inner wall and a radially spaced apart outer wall, the inner wall of the annular blade lock ring including a threaded portion threadedly engaged with the threaded portion of the annular blade housing to releasably secure the annular blade lock ring to the annular blade housing, the inner wall further including a bearing surface.

12. The blade housing assembly of claim 11 wherein the annular blade lock ring includes an upper end and an axially spaced apart lower end and an inner wall and a radially spaced apart outer wall, the inner wall including a threaded portion threadedly engaged with the threaded portion of the blade receiving body of the annular blade housing to releasably secure the annular blade lock ring to the annular blade housing.

13. The blade housing assembly of claim 11 wherein the inner wall of the blade lock ring further includes a bearing surface, the bearing surface of the first wall of the blade receiving channel of the blade receiving body of the annular blade housing and the bearing surface of the annular blade lock ring form a substantially v-shaped bearing race, a vertex of the bearing race extending in a direction radially away from the axially extending center line of the annular blade housing.

14. The blade housing assembly of claim 10 where bearing surface defined by the second offset portion of the blade receiving channel of the blade receiving body of the annular blade housing is a planar, frustoconical bearing surface, converging in a direction proceeding toward the upper end of the annular blade housing.

15. The blade housing assembly of claim 10 wherein the tissue directing surface of the shield of the blade housing includes a second arcuate tissue guide surface extending between the first tissue guide surface and the upper end of the annular blade housing, an upper end of the second arcuate tissue guide adjacent the upper end of the annular blade housing being further from the axially extending center line of the annular blade housing than a lower end of the second arcuate tissue guide.

16. A power operated dermatome comprising:
an annular rotary knife blade supported for rotation about a central axis of rotation by a blade housing assembly; and
the blade housing assembly including:
an annular blade housing including an upper end and an axially spaced apart lower end and an inner wall and a radially spaced apart outer wall, the annular blade housing centered about an axially extending center line, the blade housing including a circumferentially extending skin deflector portion including a blade receiving body and a shield extending radially inwardly from the blade receiving body, the blade receiving body including a blade receiving channel extending axially upwardly from a lower surface of the blade receiving body and radially spaced from the inner and outer walls of the annular blade housing, the blade receiving channel includes a first wall, a radially spaced apart second wall closer to the axially extending center line of the blade housing, and a bridging surface between the first and second walls, the first wall includes a first generally planar portion extending substantially parallel to the axially extending center line of the blade housing and a second offset portion, the second offset portion defining a bearing surface extending transverse to the axially extending center line of the blade housing, the shield including an inner wall defining a tissue directing surface, the tissue directing surface including a first tissue guide surface extending upwardly from a lower end of the shield, the first tissue guide surface extending substantially parallel to the axially extending center line of the annular blade housing.

17. The power operated dermatome of claim 16 wherein the first wall of the blade receiving channel of the blade receiving body includes a first generally planar portion extending substantially parallel to the axially extending center line of the blade housing and a second offset portion, the second offset portion defining the bearing surface, the bearing surface being a planar, frustoconical bearing surface, converging in a direction proceeding toward the upper end of the annular blade housing.

18. The power operated dermatome of claim 16 wherein the blade housing assembly further includes an annular blade lock ring releasably secured to the annular blade housing.

19. The power operated dermatome of claim 18 wherein the blade receiving body of the blade housing further includes a threaded portion formed on an outer surface of the blade receiving body and the annular blade lock ring includes an upper end and an axially spaced apart lower end and an inner wall and a radially spaced apart outer wall, the inner wall including a threaded portion threadedly engaged with the threaded portion of the blade receiving body of the annular blade housing to releasably secure the annular blade lock ring to the annular blade housing.

20. The power operated dermatome of claim 16 wherein the inner wall of the blade lock ring of the blade housing assembly further includes a bearing surface, the bearing surface of the first wall of the blade receiving channel of the blade receiving body of the annular blade housing and the bearing surface of the annular blade lock ring form a substantially v-shaped bearing race, a vertex of the bearing race extending in a direction radially away from the axially extending center line of the annular blade housing.

21. The power operated dermatome of claim 16 wherein the tissue directing surface of the shield of the blade housing includes a second arcuate tissue guide surface extending between the first tissue guide surface and the upper end of the annular blade housing, an upper end of the second arcuate tissue guide adjacent the upper end of the annular blade housing being further from the axially extending center line of the annular blade housing than a lower end of the second arcuate tissue guide.

* * * * *